United States Patent [19]

Saikawa et al.

[11] 4,112,090

[45] Sep. 5, 1978

[54] NOVEL PENICILLINS AND CEPHALOSPORINS AND PROCESS FOR PRODUCING THE SAME

[75] Inventors: Isamu Saikawa; Shuntaro Takano, both of Toyama; Chosaku Yoshida, Takaoka; Okuta Takashima, Toyama; Kaishu Momonoi, Shinminato; Seietsu Kuroda, Toyama; Miwako Komatsu, Toyama; Takashi Yasuda, Toyama; Yutaka Kodama, Toyama, all of Japan

[73] Assignee: Toyama Chemical Co., Ltd., Tokyo, Japan

[21] Appl. No.: 654,060

[22] Filed: Jan. 30, 1976

Related U.S. Application Data

[63] Continuation-in-part of Ser. No. 571,479, Apr. 24, 1975, Pat. No. 4,087,424.

[30] Foreign Application Priority Data

| May 9, 1974 | [JP] | Japan | 49-50663 |
| May 13, 1974 | [JP] | Japan | 49-52254 |
| May 31, 1974 | [JP] | Japan | 49-60787 |
| Aug. 13, 1974 | [JP] | Japan | 49-91996 |
| Sep. 26, 1974 | [JP] | Japan | 49-109954 |
| Dec. 13, 1974 | [JP] | Japan | 49-142499 |

[51] Int. Cl.$^2$ .................. A61K 31/43; C07D 499/70; C07D 499/66; C07D 499/68

[52] U.S. Cl. .................. 424/251; 424/250; 424/271; 260/239.1

[58] Field of Search .................. 260/239.1; 424/250, 424/251, 271

[56] References Cited

U.S. PATENT DOCUMENTS

| 3,939,150 | 2/1976 | Murakami et al. | 260/239.1 |
| 3,959,258 | 5/1976 | Konig et al. | 260/239.1 |
| 3,983,105 | 9/1976 | Konig et al. | 260/239.1 |

*Primary Examiner*—Gerald A. Schwartz
*Attorney, Agent, or Firm*—Oblon, Fisher, Spivak, McClelland & Maier

[57] ABSTRACT

Novel penicillins and cephalosporins and non-toxic salts thereof, which contain a mono- or di-oxo- or thioxo-piperazino(thio)carbonylamino group have been prepared. These compounds are valuable antibacterial compounds for use in mammals including man. A process for the preparation of the compounds has also been discovered.

40 Claims, No Drawings

NOVEL PENICILLINS AND CEPHALOSPORINS AND PROCESS FOR PRODUCING THE SAME

CROSS-REFERENCES TO RELATED APPLICATIONS

This application is a continuation-in-part of Application Ser. No. 571,479 filed Apr. 24, 1975, now U.S. Pat. No. 4,087,424.

BACKGROUND OF THE INVENTION

1. Field of the Invention

This invention relates to novel penicillins and cephalosporins and to a process for producing the same.

The compounds of the present invention have various characteristics including antibacterial activity of a broad spectrum against Gram-positive and Gram-negative bacteria, and effective antibacterial activity particularly against *Pseudomonas aeruginosa, Klebsiella pneumoniae* and *Proteus* species. Furthermore, the compounds of the present invention possess high resistance to β-lactamase produced from bacteria, and effective antibacterial activity even against clinical isolates of bacteria which are significant at present from a clinical standpoint. Accordingly, the compounds of the present invention are quite effective as therapeutic drugs for human and animal infectious diseases derived from the above-mentioned pathogenic microorganisms.

Description of the Prior Art

It has heretofore been known that 6-acylamino penicillanic acids and 7-acylaminocephalosporanic acids having an amino group at the α-position of the acyl group show strong antibacterial activity not only against Gram-positive bacteria but also against Gram-negative bacteria. However, such known compounds suffer from the disadvantage that they show substantially no effective antibacterial activity against not only *Pseudomonas aeruginosa, Klebsiella pneumoniae* and *Proteus* species, which are known to cause clinically serious infectious diseases, but also resistant bacteria which are frequently isolated at present from many clinical hospitals. Moreover, they tend to be hydrolyzed with β-lactamase produced from many drug-resistant bacteria.

SUMMARY OF THE INVENTION

With an aim to obtain penicillins and cephalosporins having none of the disadvantages mentioned above, the present inventors conducted extensive studies and found that novel compounds of formula (I) which appears hereinafter possess such properties. The compounds are prepared by bonding the moiety,

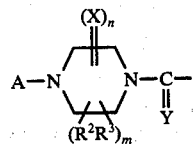

wherein A, X, Y, $R^2$, $R^3$, n and m are as defined hereinafter, to the amino group in the acyl group of pencillins and cephalosporins. Not only do such compounds sufficiently satisfy the above-mentioned aim, but they also have extremely valuable therapeutic effects.

It is an object of this invention to provide novel penicillins and cephalosporins containing a mono- or di-oxo- or thioxo-piperazino(thio)carbonylamino group.

It is another object of this invention to provide novel penicillins and cephalosporins having a broad antibacterial spectrum.

It is a further object of this invention to provide novel pencillins and cephalosporins having high resistance to β-lactamase produced from bacteria.

It is a still further object of the invention to provide novel penicillins and cephalosporins having effective antibacterial activity against clinical isolates of bacteria.

It is yet another object of this invention to provide a process for producing the novel pencillins and cephalosporins.

It is yet a further object of this invention to provide a pharmaceutical composition containing the novel pencillins or cephalosporins as active ingredient.

Other objects and advantages of this invention will become apparent from the following description.

The compounds of the present invention are pencillins and cephalosporins represented by the general formula (I),

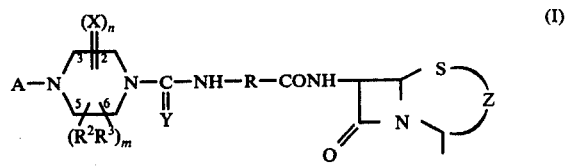

wherein R represents an amino acid residue; $R^1$ represents a hydrogen atom, a blocking group or a salt-forming cation; n represents 1 or 2; each of the n X's, which may be identical or different from one another, represents individually an oxygen or sulfur atom, and the n X's are attached in any combination to the 2-, 3- and/or 5-positions of the piperazine ring; m represents 4-n; each pair of $R^2$ and $R^3$ are linked to the same carbon atom, and m pairs of $R^2$ and $R^3$, which may be the same or different, represent individually a hydrogen atom, a halogen atom, a carboxyl group, or a substituted or unsubstituted alkyl, cycloalkyl, aryl, acyl, aralkyl, alkoxycarbonylalkyl, acyloxyalkyl, alkoxy, alkoxycarbonyl, cycloalkyloxycarbonyl, aralkoxycarbonyl, aryloxycarbonyl, amino or carbamoyl group; any pair of $R^2$ and $R^3$ together with a common carbon atom may form a cycloalkyl ring; A represents a hydrogen atom, a hydroxy group, a nitro group, a cyano group, or an unsubstituted or substituted alkyl, alkenyl, alkynyl, alkadienyl, cycloalkyl, cycloalkenyl, cycloalkadienyl, aryl, acyl, aralkyl, acyloxyalkyl, alkoxy, cycloalkyloxy, aryloxy, alkoxycarbonyl, cycloalkyloxycarbonyl, aryloxycarbonyl, aralkoxycarbonyl, alkylsulfonyl, cycloalkylsulfonyl, arylsulfonyl, carbamoyl, thiocarbamoyl, acylcarbamoyl, acylthiocarbamoyl, alkylsulfonylcarbamoyl, arylsulfonylcarbamoyl, alkylsulfonylthiocarbamoyl, arylsulfonylthiocarbamoyl, sulfamoyl, alkoxycarbonylthioalkyl, alkoxythiocarbonylthioalkyl, amino or heterocyclic group; Y represents an oxygen or sulfur atom; and >Z represents

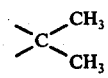

or

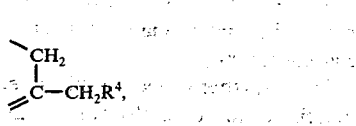

where $R^4$ represents a hydrogen atom, a halogen atom, a hydroxy group, a cyano group, an azido group, a quaternary ammonium group, or an organic group linked through O, N or S.

DETAILED DESCRIPTION OF THE PREFERRED EMBODIMENTS

In the above-mentioned general formula (I), R represents an amino acid residue. Examples of such amino acid residue include residues of amino acids derived from various aliphatic, araliphatic, aromatic, alicyclic and heterocyclic compounds, which amino acids may contain an amino group at a position such as the α-, β- or γ-position to the carboxyl group. Preferred as R is an α-amino acid residue represented by the formula

wherein $R^5$ is an alkyl group such as methyl, ethyl, propyl, butyl, pentyl, hexyl, heptyl, octyl or the like; a cycloalkyl group such as cyclopentyl, cyclohexyl, cycloheptyl or the like; a cycloalkenyl group such as cyclopentenyl, cyclohexenyl, or the like; a cycloalkadienyl group such as cyclopentadienyl, cyclohexadienyl or the like; an aryl group such as phenyl, naphthyl or the like; an aralkyl group such as benzyl, phenetyl or the like; an aryloxy group such as phenoxy, naphthoxy or the like; an alkylthioalkyl group such as methylthiomethyl, ethylthiomethyl, methylthioethyl, ethylthioethyl or the like; or a heterocyclic group such as furyl, thienyl, oxazolyl, thiazolyl, isoxazolyl, isothiazolyl, imidazolyl, pyrazolyl, pyridyl, pyrazyl, pyrimidyl, pyridazyl, quinolyl, isoquinolyl, quinazolyl, indolyl, indazolyl, 1,3,4-oxadiazolyl, 1,2,4-oxadiazolyl, 1,3,4-thiadiazolyl, 1,2,4-thiadiazolyl or the like; each group represented by said $R^5$ may be substituted by various groups, for example, halogen, hydroxy, nitro, alkyl, alkoxy, alkylthio, acyl, alkylsulfonylamino or the like; $R^6$ represents a hydrogen atom; and $R^5$ and $R^6$ together with a common carbon atom may form a cycloalkyl ring such as cyclohexyl, cycloheptyl or the like; a cycloalkenyl ring such as cyclopentenyl, cyclohexenyl, or the like; or a cycloalkadienyl ring such as cyclopentadienyl, cyclohexadienyl, or the like.

In the general formula (I), $R^1$ is a hydrogen atom, a blocking group or a salt-forming cation. The blocking group may be any of those which have heretofore been used in the field of penicillin or cephalosporin type compounds. Suitable blocking groups include (1) ester-forming groups capable of being removed by catalytic reduction, chemical reduction or hydrolysis under mild conditions, e.g., arylsulfonylalkyl groups such as toluene-sulfonylethyl, etc.; substituted or unsubstituted aralkyl groups such as benzyl, 4-nitrobenzyl, diphenylmethyl, trityl, 3,5-di(tert.-butyl)-4-hydroxybenzyl, etc.; substituted or unsubstituted alkyl groups such as tert.-butyl, trichloroethyl, etc.; the phenacyl group; alkoxyalkyl groups such as methoxymethyl, etc.; and unsubstituted or alkyl-substituted cyclic aminoalkyl groups such as piperidinoethyl, 4-methylpiperidinoethyl, morpholinoethyl, pyrrolidinoethyl, etc.; (2) ester-forming groups capable of being easily removed by enzymes in a living body, e.g. acyloxyalkyl groups such as pivaloyloxymethyl, etc.; the phthalide group; and the indanyl group; and (3) silicon-containing groups, phosphorus-containing groups and tin-containing groups which are capable of being easily removed by treating with $H_2O$ or an alcohol, such as

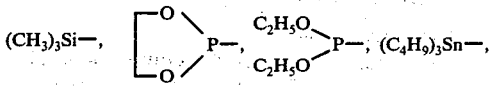

or the like. The examples of the blocking groups mentioned in (1), (2) and (3) above are merely typical, and other examples are disclosed in U.S. Pat. Nos. 3,499,909; 3,573,296 and 3,641,018 and DOS 2,301,014; 2,253,287 and 2,337,105 and may be used in this invention. Suitable salt-forming cations include cations which have heretofore been known in the field of penicillin or cephalosporin type compounds, and preferred are those capable of forming non-toxic salts. Such salts include alkali metal salts such as sodium salts, potassium salts, etc.; alkaline earth metal salts such as calcium salts, magnesium salts, etc.; ammonium salts; and salts with nitrogen-containing organic bases such as procaine, dibenzylamine, N-benzyl-β-phenethylamine, 1-ephenamine, N,N-dibenzylethylenediamine, etc. In addition to the above cations, there may be used cations capable of forming salts with other nitrogen-containing organic bases, such as trimethylamine, triethylamine, tributylamine, pyridine, dimethylaniline, N-methylpiperidine, N-methylmorpholine, diethylamine, dicyclohexylamine, etc. Furthermore, the suitable cations include quaternary ammonium groups formed at the 3-position of a cephem ring, such as pyridinium, quinolinium, isoquinolinium, pyrimidinium, and the like. In this case, a betaine structure is formed in the molecule.

In the general formula (I), m pairs of $R^2$ and $R^3$, which may be the same or different, represent individually, a hydrogen atom; a halogen atom such as fluorine, chlorine, bromine, etc.; a carboxyl group; an alkyl group such as methyl, ethyl, propyl, butyl, pentyl, hexyl, heptyl, octyl, etc.; a cycloalkyl group such as cyclopentyl, cyclohexyl, cycloheptyl, etc.; an aryl group such as phenyl, naphthyl, etc.; an acyl group such as acetyl, propionyl, butyryl, benzoyl, etc.; an aralkyl group such as benzyl, phenethyl, etc.; an alkoxycarbonylalkyl group such as methoxycarbonylmethyl, ethoxycarbonylmethyl, etc.; an acyloxyalkyl group such as acetyloxymethyl, propionyloxymethyl, pivaloyloxymethyl, benzoyloxymethyl, etc.; an alkoxy group such as methoxy, ethoxy, propoxy, butoxy, etc.; an alkoxycarbonyl group such as methoxycarbonyl, ethoxycarbonyl, propoxycarbonyl, etc.; a cycloalkyloxycarbonyl group such as cyclopentyloxycarbonyl, cyclohexyloxycarbonyl, cycloheptyloxycarbonyl, etc.; an aralkoxycarbonyl group such as benzoyloxycarbonyl, phenethoxycarbonyl, etc.; an aryloxycarbonyl group such as phenoxycarbonyl, naphthoxycarbonyl, etc.; an amino group such as amino, N-alkylamino (e.g. N-methylamino, N-ethylamino, N-propylamino, N-butylamino, etc.), N,N-dialkylamino (e.g. N,N-dimethylamino, N,N-diethylamino, N,N-dibutylamino, etc.), N-acylamino (e.g. N-acetylamino, N-propionylamino, N-butyrylamino, N-benzoylamino, etc.), and cyclic amino (e.g. pyrrolidino, piperidino, morpholino, etc.); and a carbamoyl group such as carbamoyl, N-methylaminocarbonyl, N-ethylaminocarbonyl, N,N-dimethylaminocarbonyl, N,N-diethylaminocarbonyl, etc. Furthermore, $R^2$ and $R^3$ together with a common carbon atom may form a cycloalkyl ring such as a cyclopentyl, cyclohexyl or cycloheptyl group. Each of the groups mentioned above for said $R^2$ and $R^3$ may be substituted by various substituents, for example, halogen atoms, or alkyl, alkoxy, alkylthio, acyl or nitro groups.

In the general formula (I), A represents a hydrogen atom; a hydroxy group; a nitro group; a cyano group; an alkyl group such as methyl, ethyl, propyl, isopropyl, butyl, pentyl, hexyl, heptyl, octyl, dodecyl, or the like; an alkenyl group such as vinyl, propenyl, butenyl, or the like; an alkynyl group such as propargyl, or the like; an alkadienyl group such as 1,3-butadienyl, 1,3-pentadienyl, or the like; a cycloalkyl group such as cyclopentyl, cyclohexyl, cycloheptyl, or the like; a cycloalkenyl group such as cyclopentenyl, cyclohexenyl, or the like; a cycloalkadienyl group such as cyclopentadienyl, cyclohexadienyl, or the like; an aryl group such as phenyl, naphthyl, or the like; an acyl group such as formyl, acetyl, propionyl, isovaleryl, caproyl, enanthoyl, capryloyl, palmitoyl, stearoyl, acryloyl, cyclohexanecarbonyl, benzoyl, phenylglycyl, furoyl, thenoyl, or the like; an aralkyl group such as benzyl, phenethyl, or the like; an acyloxyalkyl group such as acetyloxyethyl, pivaloyloxymethyl, benzoyloxymethyl, or the like; an alkoxy group such as methoxy, ethoxy, propoxy, butoxy, or the like; a cycloalkyloxy group such as cyclopentyloxy, cyclohexyloxy, cycloheptyloxy, or the like; an aryloxy group such as phenoxy, naphthoxy, or the like; an alkoxycarbonyl group such as methoxycarbonyl, ethoxycarbonyl, propoxycarbonyl, butoxycarbonyl, or the like; a cycloalkyloxycarbonyl group such as cyclopentyloxycarbonyl, cyclohexyloxycarbonyl, cycloheptyloxycarbonyl, or the like; an aryloxycarbonyl group such as phenoxycarbonyl, (1- or 2-)naphthoxycarbonyl, or the like; an aralkoxycarbonyl group such as benzyloxycarbonyl, phenethoxycarbonyl, or the like; an alkysulfonyl group such as methanesulfonyl, ethanesulfonyl, propanesulfonyl, butanesulfonyl, or the like; a cycloalkylsulfonyl group such as cyclopentanesulfonyl, cyclohexanesulfonyl, or the like; an arylsulfonyl group such as benzenesulfonyl, (1- or 2-)naphthalenesulfonyl, or the like; a carbamoyl group such as carbamoyl, N-alkylaminocarbonyl (e.g. N-methylaminocarbonyl, N-ethylaminocarbonyl, N-propylaminocarbonyl, N-butylaminocarbonyl, or the like), N-arylaminocarbonyl (e.g. N-phenylaminocarbonyl, or the like), N,N-dialkylaminocarbonyl (e.g. N,N-dimethylaminocarbonyl, N,N-diethylaminocarbonyl, or the like), cyclic amino carbonyl (e.g. pyrrolidinocarbonyl, piperidinocarbonyl, morpholinocarbonyl, or the like); a thiocarbamoyl group such as thiocarbamoyl, N-alkylaminothiocarbonyl (e.g. N-methylaminothiocarbonyl, N-ethylaminothiocarbonyl, N-propylaminothiocarbonyl, or the like), N-arylaminothiocarbonyl (e.g. N-phenylaminothiocarbonyl, or the like), N,N-dialkylaminothiocarbonyl (e.g. N,N-dimethylaminothiocarbonyl, N,N-diethylaminothiocarbonyl, or the like), or cyclic aminothiocarbonyl (e.g. pyrrolidinothiocarbonyl, piperidinothiocarbonyl, morpholinothiocarbonyl, or the like); an acylcarbamoyl group such as N-acetylcarbamoyl, N-propionylcarbamoyl, N-butyrylcarbamoyl, N-benzoylcarbamoyl, N-furoylcarbamoyl, N-thenoylcarbamoyl, or the like; an acylthiocarbamoyl group such as N-acetylthiocarbamoyl, N-propionylthiocarbamoyl, N-butyrylthiocarbamoyl, N-benzoylthiocarbamoyl, N-naphthoylthiocarbamoyl, N-furoylthiocarbamoyl, N-thenoylthiocarbamoyl, or the like); an alkylsulfonylcarbamoyl group such as methanesulfonylaminocarbonyl, ethanesulfonylaminocarbonyl, butanesulfonylaminocarbonyl, or the like; an arylsulfonylcarbamoyl group such as benzenesulfonylaminocarbonyl, (1- or 2-)naphthalenesulfonylaminocarbonyl, or the like; an alkylsulfonylthiocarbamoyl group such as methanesulfonylaminothiocarbonyl, ethanesulfonylaminothiocarbonyl, butanesulfonylaminothiocarbonyl, or the like; an arylsulfonylthiocarbamoyl group such as benzenesulfonylaminothiocarbonyl, naphthalenesulfonylaminothiocarbonyl, or the like; a sulfamoyl group such as sulfamoyl, N-methylsulfamoyl, N-ethylsulfamoyl, N-propylsulfamoyl, N-butylsulfamoyl, N,N-dimethylsulfamoyl, N,N-diethylsulfamoyl, N,N-dipropylsulfamoyl, N,N-dibutylsulfamoyl, N-phenylsulfamoyl, N-benzylsulfamoyl, N-cyclopentylsulfamoyl, N-cyclohexylsulfamoyl, or the like; an alkoxycarbonylthioalkyl group such as methoxycarbonylthiomethyl, ethoxycarbonylthiomethyl, propoxycarbonylthiomethyl, butoxycarbonylthiomethyl, methoxycarbonylthioethyl, or the like; an alkoxythiocarbonylthioalkyl group such as methoxythiocarbonylthiomethyl, ethoxythiocarbonylthiomethyl, propoxythiocarbonylthiomethyl, butoxythiocarbonylthiomethyl, methoxythiocarbonylthioethyl, or the like; an amino group such as amino, N-alkylamino (e.g. N-methylamino, N-ethylamino, N-propylamino, N-butylamino, or the like), N,N-dialkylamino (e.g. N,N-dimethylamino, N,N-diethylamino, N,N-dibutylamino, or the like), N-acylamino (e.g. N-acetylamino, N-propionylamino, N-butyrylamino, N-benzoylamino, or the like), or cyclic amino (e.g. pyrrolidino, piperidino, morpholino, or the like); or a heterocyclic group such as thiazolyl, pyridyl, pyridazyl, pyrazyl, thiadiazolyl, triazolyl, tetrazolyl, quinolyl, or the like. Each of the groups mentioned above for A in formula (I) may be substituted by any of such substituents as, for example, halogen atoms, hydroxyl groups, alkyl groups, alkoxy groups, alkythio groups, nitro groups, cyano groups, amino groups (e.g. dialkylamino, cyclic amino, etc.), carboxyl groups, acyl groups, etc.

Suitable quaternary ammonium groups for $R^4$ include pyridinium, quinolinium, isoquinolinium and pyrimidinium. Furthermore, suitable organic groups which are linked through O, N or S for $R^4$ include alkoxy groups such as methoxy, ethoxy, propoxy, etc.; aryloxy groups such as phenoxy, naphthoxy, etc.; aralkoxy groups such as benzoyloxy, phenethoxy, etc.; acyloxy groups such as acetyloxy, propionyloxy, butyryloxy, benzoyloxy, naphthoyloxy, cyclopentanecarbonyloxy, cyclohexanecarbonyloxy, furoyloxy, thenoyloxy, etc.; carbamoyloxy groups such as carbamoyloxy, N-methylaminocarbonyloxy, N,N-dimethylaminocarboxyloxy, N-acetylaminocarbonyloxy, phenylaminocarbonyloxy, benzylaminocarbonyloxy, cyclohexylaminocarbonyloxy, etc.; guanidino groups such as guanidino, N-methylguanidino, etc.; amino groups such as amino, N-alkylamino (e.g. N-methylamino, N-ethylamino, N-propylamino, N-butylamino, N-cyclohexylamino, N-phenylamino, etc.) N,N-dialkylamino (e.g. N,N-dimethylamino, N,N-diethylamino, N,N-dibutylamino, etc.), and cyclic amino (e.g. pyrrolidino, piperidino, morpholino, etc.); alkylthio groups such as methylthio, ethylthio, propylthio, etc.; arylthio groups such as phenylthio, (1- or 2-)-naphthylthio, etc.; aralkylthio groups such as benzylthio, phenethylthio, etc.; acylthio groups such as acetylthio, propionylthio, butyrylthio, benzoylthio, (1- or 2-)naphthoylthio, cyclopentanecarbonylthio, cyclohexanecarbonylthio, furoylthio, thenoylthio, isothiazolecarbonylthio, isoxazolecarbonylthio, thiadiazolecarbonylthio, triazolecarbonylthio, etc.; thiocarbamoylthio groups such as thiocarbamoylthio, N-methyl-thiocarbamoylthio, N,N-diethylthiocarbamoylthio, 1-piperidino-thiocarbonylthio, 1-morpholino-thiocarbonylthio, 4-methyl-1-piperazinothiocarbonylthio, etc.; alkoxythiocarbonylthio groups such as methoxythiocarbonylthio, ethoxythiocarbonylthio, propoxythiocarbonylthio, butoxythiocarbonylthio, etc.; aryloxythiocarbonylthio groups such as phenoxythiocarbonylthio, etc.; cycloalkyloxythiocarbonylthio groups such as cyclohexyloxythiocarbonylthio, etc.; amidinothio groups such as amidinothio, N-methylamidinothio, N,N'-dimethylamidinothio, etc.; and heterocycle thio groups such as oxazolylthio, thiazolylthio, isoxazolylthio, isothiazolylthio, imidazolylthio, pyrazolylthio, pyridylthio, pyrazinylthio, pyrimidinylthio, pyridazinylthio, quinolylthio, isoquinolylthio, quinazolylthio, indolylthio, indazolylthio, oxadiazolylthio, thiadiazolylthio, triazolylthio, tetrazolylthio, triazinylthio, benzimidazolylthio, benzoxazolylthio, benzothiazolylthio, triazolopyridylthio, purinylthio, pyridine-1-oxide-2-ylthio, pyridazine-1-oxide-6-ylthio, etc. Each of the groups mentioned above for $R^4$ may be substituted by any of such substituents as, for example, halogen atoms, alkyl groups, alkoxy groups, alkylthio groups, nitro groups, cyano groups, acylamino groups, acyl groups, carboxyl groups, carbamoyl groups, etc.

The above-mentioned compounds of formula (I) of the present invention have optical isomers, and all of the D-isomers, L-isomers and racemic compounds thereof are included in the scope of the present invention.

In the present invention preferred compounds of the general formula (I) are as follows:

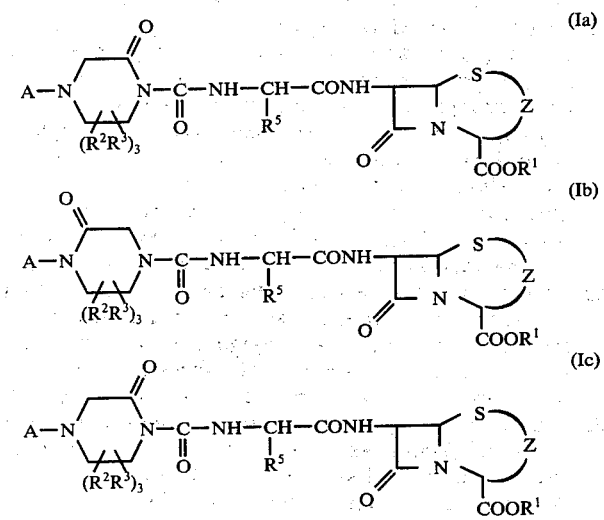

-continued

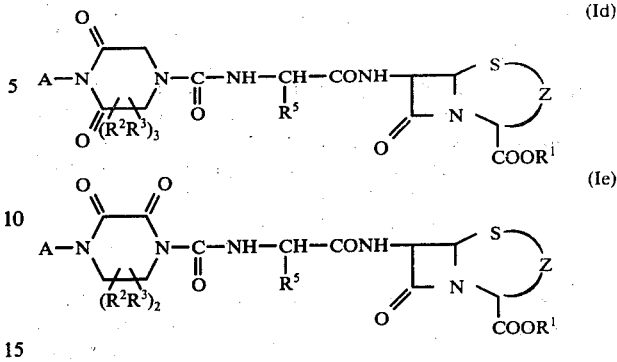

wherein $R^1$, $R^2$, $R^3$, A, $R^5$ and >Z are as defined above.

The compounds of formula (I) of the present invention are produced according to any one of the processes (1), (2) and (3) described below.

Process (1):

This process comprises reacting a compound represented by the general formula (II),

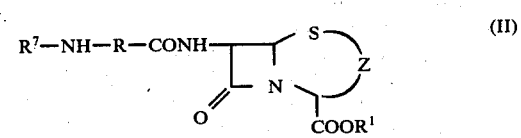

with a reactive derivative of the

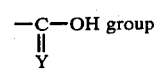

(hereinafter referred to as a "(thio)carboxyl group") of a compound represented by the general formula (III),

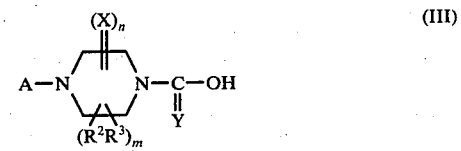

Process (2):

This process comprises reacting a compound represented by the general formula (IV),

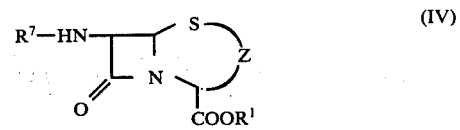

with a compound represented by the general formula (V),

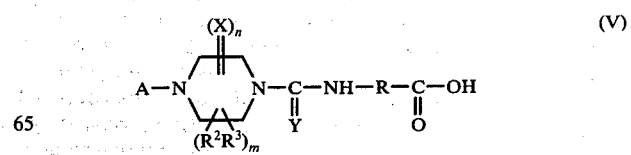

or with a reactive derivative of the

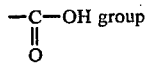—C—OH group (hereinafter referred to as a "carboxyl group") of the compound of formula (V).

Process (3):

This process comprises reacting a compound represented by the general formula (VI),

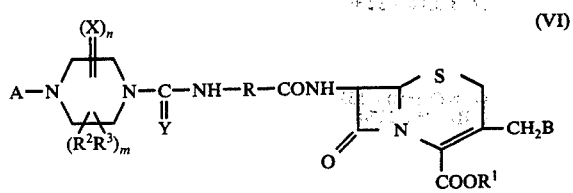

with a compound represented by the general formula (VII),

R$^8$M     (VII)

or with a tertiary amine.

In the above-mentioned formulas (II) to (VI), R, R$^1$, R$^2$, R$^3$, R$^4$, X, m, n, A, Y and >Z are as defined above; and R$^7$ represents a hydrogen atom, a silicon-containing group or a phosphorus-containing group. Suitable silicon-containing and phosphorus-containing groups are the same as those mentioned above for R$^1$.

In the aforesaid formula (VI), B represents a substituent capable of being easily replaced by a nucleophilic reagent, and includes, for example, halogen atoms such as chlorine, bromine, etc.; lower alkanoyloxy groups such as formyloxy, acetoxy, propionyloxy, butyryloxy, pivaloyoxy, etc.; arylcarbonyloxy groups such as benzoyloxy, naphthoyloxy, etc.; arylcarbonylthio groups such as benzoylthio, naphthoylthio, etc.; carbamoyloxy groups; heteroaromatic amino N-oxide thio groups having a thio group on the carbon atom adjacent to the N-oxide group in the molecule, such as pyridine-1-oxide-2-ylthio, pyridazine-1-oxide-6-ylthio, etc. Each of the groups mentioned above for B may be substituted by any of such substituents as, for example, halogen atoms, nitro groups alkyl groups, alkoxy groups, alkylthio groups, acyl groups, etc.

In formula (VII), R$^8$ represents a cyano group, an azido group or an organic group linked through O, N or S. The organic group is the same as mentioned above for R$^4$.

In the formula (VII), M represents a hydrogen atom, an alkali metal or an alkaline earth metal. Suitable tertiary amines used in the process (3) include pyridine, quinoline, isoquinoline, pyrimidine, etc. These tertiary amines may be substituted by various substituents such as halogen, lower alkyl, carbamoyl and the like.

Any of the D-isomer, L-isomer or racemic compound may be used as compound II.

As the reactive derivative of the (thio)carboxyl group of the compound of formula (III), there is used a reactive derivative of a carboxylic acid which is ordinarily employed for the synthesis of acid amide compounds. Examples of the reactive derivative are acid halides, acid azides, acid cyanides, mixed acid anhydrides, active esters, active amides, etc. Particularly preferable examples thereof are acid halides such as acid chlorides, acid bromides, etc., and active esters such as cyanomethyl ester, trichloromethyl ester, etc.

The reactive derivative of the (thio)carboxyl group of the compound of formula (III) can be easily obtained by reacting, for example, an oxopiperazine or thioxopiperazine of formula (VIII), synthesized according to the process of the literature references described below, with phosgene, thiophosgene, trichloromethyl ester of chloroformic acid, or the like,

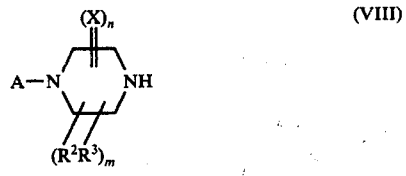

wherein A, X, R$^2$, R$^3$, m and n are as defined previously.

Literature references:

V. G. Granik, Khim-Farm. Zh., I(4), 16–19 (1967) (Russ);

Samuel R. Aspinall, J. An. Chem. Soc., 62, 1202-4 (1940);

Kuniyoshi MASUZAWA, Pharm. Bull. (Japan), 38 2078-2081 (1966);

Arthur P. Phillips, Ger. 1135472, Aug. 30 (1962);

J. L. Riebsomer, J. Org. Chem., 15 68–73 (1950);

Jongkees, Rec. trav. Chim., 27 305;

Patric T. Izzo, J. Am. Chem. Soc., 81 4668-4670 (1959); and

B. H. Chase & A. M. Downes, J. Chem. Soc., 3874–3877 (1953).

Examples of the compound of formula (VIII) and the (thio)carboxyl group reactive derivative of the compound of formula (III) are as set forth in Table 1 and Table 2, respectively, but, of course, these are not limitative.

Table 1

| Compound | m.p. (recrystallization solvent) | IR (cm$^{-1}$) |
|---|---|---|
| HN⟨⟩NH (with C=O) | 136° C (⟨O⟩) | νC=O 1640 νNH 3450 – 3250 |

Table 1-continued $$\text{AN}\underset{(R^2\ R^3)_m}{\overset{(X)_n}{\diagup\hspace{-1em}\diagdown}}\text{NH} \quad (VIII)$$

| Compound | m.p. (recrystallization solvent) | IR (cm$^{-1}$) |
|---|---|---|
| 3-methyl-2-oxopiperazine (HN-CO-C(CH$_3$)-CH$_2$-NH-CH$_2$) | b.p. 143° C/1 mmHg oily material | $\nu$C=O 1650<br>$\nu$NH 3300 – 3200 |
| 5-methyl-2-oxopiperazine | b.p. 122 – 125° C/2 mmHg<br>140 – 141° C (IPA) | $\nu$C=O 1650 – 1630<br>$\nu$NH 3260, 3170 |
| 3,5-dimethyl-2-oxopiperazine | 85 – 86° C (IPA - IPE) | $\nu$C=O 1660 – 1620 |
| 3-(ethoxycarbonylmethyl)-2-oxopiperazine (CH$_2$CO$_2$C$_2$H$_5$ substituent) | 105 – 106° C (AcOEt) | $\nu$C=O 1710, 1640<br>$\nu$NH 3380, 3190 |
| 4-acetyl-2-oxopiperazine, CH$_3$CON- | 112 – 113° C (benzene) | $\nu$C=O 1645, 1625<br>$\nu$NH 3380, 3190 |
| 4-chloroacetyl-2-oxopiperazine, ClCH$_2$CON- | 129 – 130° C (IPA) | $\nu$C=O 1650, 1630<br>$\nu$NH 3270 |
| 4-dichloroacetyl-2-oxopiperazine, Cl$_2$CHCON- | 134 – 135° C (IPA) | $\nu$C=O 1660 – 1630<br>$\nu$NH 3280 |
| CH$_3$(CH$_2$)$_{13}$CH$_2$CON- | 96 – 97° C (CCl$_4$) | $\nu$C=O 1670, 1640<br>$\nu$NH 3200 |
| CH$_3$(CH$_2$)$_5$CH$_2$CON- | 80 – 81° C (IPE) | $\nu$C=O 1660, 1620<br>$\nu$NH 3250 |
| CH$_3$(CH$_2$)$_4$CH$_2$CON- | 83 – 84° C (IPE) | $\nu$C=O 1660, 1620<br>$\nu$NH 3250 |
| CH$_3$(CH$_2$)$_3$CH$_2$CON- | 99 – 100° C (CCl$_4$) | $\nu$C=O 1660, 1620<br>$\nu$NH 3250 |
| cyclohexyl-CON- | 203 – 205° C (IPA) | $\nu$C=O 1670, 1620<br>$\nu$NH 3250 |
| cyclohexyl-CH$_2$-CON- | 91 – 93° C (IPA) | $\nu$C=O 1640, 1600<br>$\nu$NH 3250 |

Table 1-continued $$\underset{(R^2\ R^3)_m}{\overset{(X)_n}{AN\diagup NH}}\quad (VIII)$$

| Compound | m.p. (recrystallization solvent) | IR (cm$^{-1}$) |
|---|---|---|
| 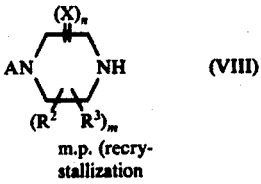 | 146 – 148° C (IPA) | νC=O 1650, 1620<br>νNH 3200 |
| 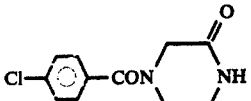 | 118 – 120° C (IPA) | νC=O 1660, 1620<br>νNH 3200 |
| 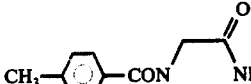 | 182 – 185° C (IPA) | νC=O 1670, 1600<br>νNH 3200 |
|  | Oily material | νC=O 1650, 1620<br>νNH 3200 |
| 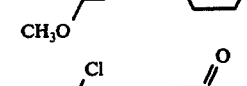 | 124 – 126° C (⌬) | νC=O 1650, 1630<br>νNH 3225 |
| 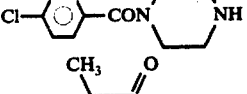 | 167 – 168° C (EtOH) | νC=O 1680<br>νNH 3200<br>νSO$_2$N< 1310, 1140 |
| 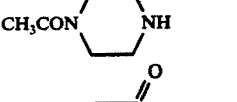 | 176 – 179° C (⌬) | νC=O 1680, 1650, 1620<br>νNH 3300 |
| 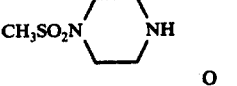 | 85 – 88° C (AcOEt) | νC=O 1660, 1640<br>νNH 3300, 3200 |
|  | 81 – 82° C (dioxane) | νC=O 1690 – 1650<br>νNH 3200, 3050 |
|  | 189 – 190° C (IPA) | νC=O 1650, 1620<br>νNH 3250 |
| 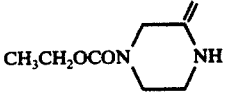 | 136 – 138° C (Acetone) | νC=O 1660<br>νNH 3200 |
| 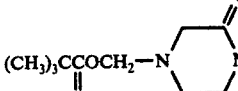 | Oily material | νC=O 1650 – 1630<br>νNH 3270 |
| 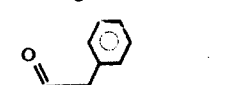 | Oily material | νNH 3250<br>νC=O 1650 – 1630 |

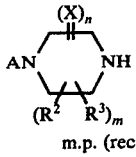

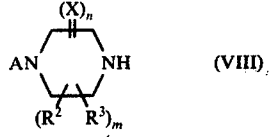

Table 1-continued $$\text{AN} \underset{(R^2\ R^3)_m}{\overset{(X)_n}{\diamond}} \text{NH} \quad \text{(VIII)}$$

| Compound | m.p. (recrystallization solvent) | IR (cm$^{-1}$) |
|---|---|---|
| CH$_3$CO—N(C=O)₂—NH | 184 – 185° C (EtOH) | $\nu$C=O 1690 – 1650<br>$\nu$NH 3190, 3050 |
| C$_6$H$_5$—CO—N(C=O)₂—NH | 177 – 178° C (EtOH) | $\nu$C=O 1680 – 1650<br>$\nu$NH 3190, 3050 |
| CH$_3$—N(C=O)₂—NH | 142 – 143° C (IPA) | $\nu$C=O 1680 – 1620<br>$\nu$NH 3200 |
| C$_6$H$_5$—CH$_2$—N(C=O)₂—NH | 209° C (IPA) | $\nu$C=O 1660 – 1630<br>$\nu$NH 3230 |
| CH$_3$—N(C=O)(C=O)—NH | 158° C (IPA) | $\nu$C=O 1695, 1660<br>$\nu$NH 3220 |
| CH$_3$COOCH$_2$CH$_2$—N(C=O)(C=O)—NH | Oily material | $\nu$C=O 1730 – 1650<br>$\nu$NH 3300 – 3200 |
| CH$_3$CH$_2$—N(C=O)(C=O)—NH | 124° C (dioxane) | $\nu$C=O 1680, 1650<br>$\nu$NH 3250 |
| CH$_3$CH$_2$CH$_2$—N(C=O)(C=O)—NH | 98 – 100° C (dioxane) | $\nu$C=O 1680, 1650<br>$\nu$NH 3200, 3100 |
| CH$_3$(CH$_2$)$_2$CH$_2$—N(C=O)(C=O)—NH | 111 – 113° C (CCl$_4$) | $\nu$C=O 1695, 1670<br>$\nu$NH 3240, 3150 |
| (CH$_3$)$_2$CH—N(C=O)(C=O)—NH | 166 – 167° C (dioxane) | $\nu$C=O 1650<br>$\nu$NH 3300 – 3200 |
| CH$_3$(CH$_2$)$_3$CH$_2$—N(C=O)(C=O)—NH | 104 – 106° C (IPE) | $\nu$C=O 1700, 1660<br>$\nu$NH 3200, 3100 |
| CH$_3$(CH$_2$)$_4$CH$_2$—N(C=O)(C=O)—NH | 111 – 115° C (IPE) | $\nu$C=O 1700, 1660<br>$\nu$NH 3200, 3100 |

Table 1-continued

Structure (VIII):

AN, NH piperazine with $(X)_n$ and $(R^2, R^3)_m$ substituents

| Compound | m.p. (recrystallization solvent) | IR (cm$^{-1}$) |
|---|---|---|
| CH$_3$(CH$_2$)$_5$CH$_2$–N-piperazine-2,3-dione | 112 – 115° C (IPE) | νC=O 1700, 1660 <br> νNH 3200, 3100 |
| CH$_3$(CH$_2$)$_6$CH$_2$–N-piperazine-2,3-dione | 116 – 120° C (IPE) | νC=O 1700, 1660 <br> νNH 3225, 3100 |
| CH$_2$=CHCH$_2$–N-piperazine-2,3-dione | 136 – 137° C (Acetone) | νC=O 1680, 1655 <br> νNH 3200, 3100 |
| Phenyl–N-piperazine-2,3-dione | 202 – 204° C (IPA) | νC=O 1690, 1645 <br> νNH 3260 |
| ClCH$_2$CH$_2$–N-piperazine-2,3-dione | 128 – 129° C (EtOH) | νC=O 1700 – 1650 <br> νNH 3200– 3100 |
| CH$_3$CH$_2$–N-piperazine-2,3-dione (5-CH$_3$) | 127 – 128° C (AcOEt) | νC=O 1660 <br> νNH 3200, 3080 |
| CH$_3$–N-piperazine-2,3-dione (5-CH$_3$) | 146 – 147° C (dioxane) | νC=O 1660 <br> νNH 3200, 3100 |
| Spiro-cyclohexane piperazine-2,5-dione | 183 – 185° C (EtOH) | νC=O 1720, 1660 <br> νNH 3320, 3175, 3050 |
| Benzyl-N-spiro-cyclohexane piperazinedione | 96 – 99° C (IPA-n-Hexane) | νC=O 1720, 1660 <br> νNH 3330 |
| Cl$_3$CCH$_2$OCO–N-spiro-cyclohexane piperazinedione | 143 – 146° C (IPA) | νC=O 1765, 1720, 1680 <br> νNH 3350 |
| piperazine-2,5-dione | 210 – 212° C (MeOH) | νC=O 1680 <br> νNH 3380, 3290, 3070 |

Table 1-continued

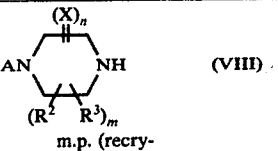 (VIII)

| Compound | m.p. (recrystallization solvent) | IR (cm$^{-1}$) |
|---|---|---|
| 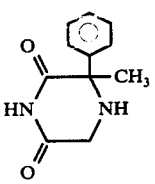 | 132 – 133° C (EtOH) | $\nu$C=O 1715, 1685<br>$\nu$NH 3275, 3170 |
| 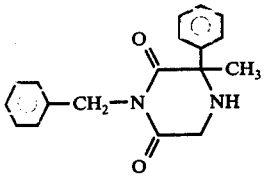 | 98 – 100° C (IPA) | $\nu$C=O 1715, 1665<br>$\nu$NH 3360 |

Note:
IPA=(CH$_3$)$_2$CHOH
IPE=(CH$_3$)$_2$CHOCH(CH$_3$)$_2$
AcOEt=CH$_3$COOCH$_2$CH$_3$
EtOH=CH$_3$CH$_2$OH Table 2

Reactive derivatives of 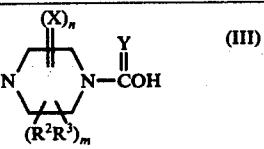 (III)

| Compound | Physical property | I.R. (cm$^{-1}$) |
|---|---|---|
| 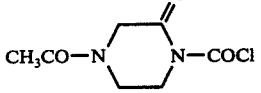 | Oily material | $\nu$C=O 1790, 1710, 1640 |
| 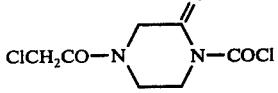 | " | $\nu$C=O 1790, 1730 – 1650 |
| 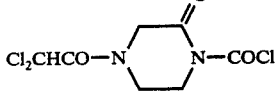 | " | $\nu$C=O 1790, 1730 – 1650 |
| 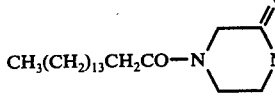 | " | $\nu$C=O 1740, 1660, 1640 |
| 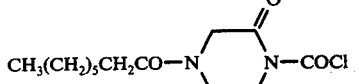 | " | $\nu$C=O 1740, 1680 – 1640 |
| 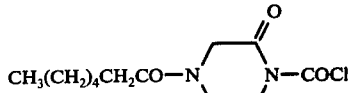 | " | $\nu$C=O 1740, 1680 – 1640 |
| 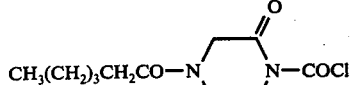 | " | $\nu$C=O 1790, 1710, 1640 |
|  | | |

Table 2-continued

Reactive derivatives of formula (III):

$$A-N\overset{(X)_n}{\underset{(R^2R^3)_m}{\bigcirc}}N-\overset{Y}{\underset{\|}{C}}OH$$

| Compound | Physical property | I.R. (cm$^{-1}$) | |
|---|---|---|---|
| Cyclohexyl-CO-N(ring with =O)N-COCl | " | νC=O | 1790, 1730, 1640 |
| Phenyl-CO-N(ring with =O)N-COCl | " | νC=O | 1740, 1660, 1630 |
| 4-Cl-C$_6$H$_4$-CO-N(ring with =O)N-COCl | " | νC=O | 1740, 1640 |
| 4-CH$_3$-C$_6$H$_4$-CO-N(ring with =O)N-COCl | " | νC=O | 1730, 1650 |
| 3,4,5-(CH$_3$O)$_3$-C$_6$H$_2$-CO-N(ring with =O)N-COCl | " | νC=O | 1740, 1640 |
| 2,4-Cl$_2$-C$_6$H$_3$-CO-N(ring with =O)N-COCl | " | νC=O | 1720, 1640 |
| CH$_3$CO-N(ring with CH$_3$, =O)N-COCl | " | νC=O | 1790, 1710, 1640 |
| CH$_3$SO$_2$-N(ring with =O)N-COCl | " | νC=O νSO$_2$ | 1790, 1700 1320, 1140 |
| CH$_3$CONHCO-N(ring with =O)N-COCl | " | νC=O | 1790, 1720 – 1660 |
| C$_6$H$_5$-NHCO-N(ring with =O)N-COCl | " | νC=O | 1740, 1720, 1650 |
| CH$_3$CH$_2$OCO-N(ring with =O)N-COCl | " | νC=O | 1750, 1720, 1640 |
| (CH$_3$)$_3$CCOOCH$_2$-N(ring with =O)N-COCl | " | νC=O | 1740 – 1720, 1670 |
| CH$_3$(CH$_2$)$_4$CH$_2$-N(ring with =O)N-COCl | " | νC=O | 1790, 1720 |

Table 2-continued

| Compound | Physical property | | I.R. (cm⁻¹) |
|---|---|---|---|
| CH₃(CH₂)₂CH₂—N(piperazinone)—COCl | | νC=O | 1790, 1720 |
| CH₃(CH₂)₂CH₂—N(piperazinone, CH₃)—COCl | " | νC=O | 1790, 1720 |
| CH₃(CH₂)₆CH₂—N(piperazinone)—COCl | " | νC=O | 1790, 1720 |
| HN(piperazinone)—COCl | m.p. 115 – 116° C (decomp.) (from benzene) | νC=O | 1720, 1660 |
| HN(piperazinone, CH₃, CH₃)—COCl | Crystal | νC=O | 1730, 1670 |
| HN(piperazinone, CH₃)—COCl | Crystal | νC=O | 1720, 1660 |
| HN(piperazinone, CH₂COOCH₂CH₃)—COCl | m.p. 59 – 60° C (from IPE) | νC=O | 1710 – 1730, 1660 |
| HN(piperazinone, CH₃)—COCl | m.p. 98 – 100° C (from benzene) | νC=O | 1725, 1650 |
| CH₃CO—N(piperazinone, CH₃)—COCl | Oily material | νC=O | 1720, 1690 |
| Ph-NHCO—N(piperazinone)—COCl | " | νC=O | 1790, 1740 – 1700 |
| CH₃—N(piperazinone)—COCl | " | νC=O | 1710, 1630 |
| CH₃(CH₂)₂CH₂—N(piperazinone)—COCl | " | νC=O | 1730, 1650 |
| CH₃CH₂—N(piperazinone)—COCl | " | νC=O | 1730, 1650 |

Table 2-continued

Reactive derivatives of (III)

| Compound | Physical property | I.R. (cm$^{-1}$) |
|---|---|---|
| (CH$_3$)$_2$CH—N[3-oxopiperazine]N—COCl | " | $\nu$C=O 1720, 1640 |
| CH$_3$(CH$_2$)$_3$CH$_2$—N[3-oxopiperazine]N—COCl | " | $\nu$C=O 1730, 1640 |
| (CH$_3$)$_2$CHCH$_2$CH$_2$—N[3-oxopiperazine]N—COCl | " | $\nu$C=O 1720, 1640 |
| CH$_3$(CH$_2$)$_4$CH$_2$—N[3-oxopiperazine]N—COCl | " | $\nu$C=O 1730, 1640 |
| CH$_3$(CH$_2$)$_5$CH$_2$—N[3-oxopiperazine]N—COCl | " | $\nu$C=O 1730, 1640 |
| CH$_3$(CH$_2$)$_6$CH$_2$—N[3-oxopiperazine]N—COCl | " | $\nu$C=O 1720, 1640 |
| CH$_3$(CH$_2$)$_{10}$CH$_2$—N[3-oxopiperazine]N—COCl | " | $\nu$C=O 1720, 1640 |
| cyclopentyl-N[3-oxopiperazine]N—COCl | " | $\nu$C=O 1730, 1640 |
| CH$_3$(CH$_2$)$_2$CH$_2$—N[3-oxo-2-methylpiperazine]N—COCl | " | $\nu$C=O 1730, 1640 |
| CH$_3$(CH$_2$)$_2$CH$_2$—N[5-oxo-3-methylpiperazine]N—COCl | " | $\nu$C=O 1720, 1640 |
| CH$_3$(CH$_2$)$_2$CH$_2$—N[3-oxo-6-methylpiperazine]N—COCl | " | $\nu$C=O 1730, 1650 |
| 3-phenyl-2-oxopiperazine-1-COCl | m.p. 105 – 107° C | $\nu$C=O 1730, 1650 |

Table 2-continued

Reactive derivatives of $\text{A}-\text{N}\underset{(R^2R^3)_m}{\overset{(X)_n}{\rightleftarrows}}\text{N}-\overset{Y}{\underset{}{\text{COH}}}$ (III)

| Compound | Physical property | I.R. (cm$^{-1}$) | |
|---|---|---|---|
| PhCH$_2$-N(C=O)N-COCl (piperazinone) | Oily material | $\nu$C=O | 1720, 1645 |
| H$_2$NCO-N(C=O, CH$_3$)N-COCl | " | $\nu$C=O | 1700 – 1740 |
| HOCH$_2$CH$_2$-N(C=O)N-COCl | " | $\nu$C=O | 1730, 1660 – 1630 |
| CH$_2$=CHCH$_2$-N(C=O)N-COCl | " | $\nu$C=O | 1720, 1640 |
| CH$_2$=CHCH(CH$_3$)-N(C=O)N-COCl | " | $\nu$C=O | 1730, 1650 |
| CH$_2$=C(CH$_3$)CH$_2$-N(C=O)N-COCl | " | $\nu$C=O | 1730, 1650 |
| CH$_3$CH=CHCH$_2$-N(C=O)N-COCl (trans-) | " | $\nu$C=O | 1730, 1650 |
| Morpholino-CH$_2$-N(C=O)N-COCl | m.p. 150° C (decomp.) | $\nu$C=O | 1670, 1720 |
| CH$_3$CO-N(C=O)N(C=O)-COCl (2,5-dioxopiperazine) | Oily material | $\nu$C=O | 1790, 1720 – 1670 |
| PhCO-N(C=O)N(C=O)-COCl | " | $\nu$C=O | 1790, 1710, 1670 |
| CH$_3$-N(C=O)N(C=O)-COCl | " | $\nu$C=O | 1790, 1710 – 1660 |
| PhCH$_2$-N(C=O)N(C=O)-COCl | " | $\nu$C=O | 1790, 1710 – 1660 |

Table 2-continued

Reactive derivatives of (III)

$$A-N\underset{(R^2R^3)_m}{\overset{(X)_n}{\underset{\|}{\bigcirc}}}N-\overset{Y}{\underset{\|}{C}}OH$$

| Compound | Physical property | I.R. (cm$^{-1}$) | |
|---|---|---|---|
| CH$_3$—N(piperazine-2,3-dione)—COCl | m.p. 94 – 95° C (decomp.) (from CH$_2$Cl$_2$—Et$_2$O) | νC=O | 1790, 1680 |
| CH$_3$COOCH$_2$CH$_2$—N(piperazine-2,3-dione)—COCl | Oily material | νC=O | 1790, 1720, 1670 |
| CH$_3$CH$_2$—N(piperazine-2,3-dione)—COCl | m.p. 95 – 96° C (decomp.) (from AcOBu) | νC=O | 1780, 1660 |
| CH$_3$CH$_2$CH$_2$—N(piperazine-2,3-dione)—COCl | Oily material | νC=O | 1780, 1710 – 1640 |
| CH$_3$(CH$_2$)$_2$CH$_2$—N(piperazine-2,3-dione)—COCl | " | νC=O | 1780, 1660 |
| (CH$_3$)$_2$CH—N(piperazine-2,3-dione)—COCl | m.p. 130 – 131° C (decomp.) | νC=O | 1780, 1660 |
| CH$_3$(CH$_2$)$_3$CH$_2$—N(piperazine-2,3-dione)—COCl | Oily material | νC=O | 1790, 1720 – 1665 |
| CH$_3$(CH$_2$)$_4$CH$_2$—N(piperazine-2,3-dione)—COCl | " | νC=O | 1780, 1720 – 1640 |
| CH$_3$(CH$_2$)$_5$CH$_2$—N(piperazine-2,3-dione)—COCl | " | νC=O | 1780, 1720 – 1640 |
| CH$_3$(CH$_2$)$_6$CH$_2$—N(piperazine-2,3-dione)—COCl | " | νC=O | 1780, 1720 – 1640 |
| CH$_2$=CHCH$_2$—N(piperazine-2,3-dione)—COCl | Crystal | νC=O | 1775, 1660 – 1620 |
| C$_6$H$_5$—N(piperazine-2,3-dione)—COCl | Crystal | νC=O | 1785, 1720 – 1650 |
| ClCH$_2$CH$_2$—N(piperazine-2,3-dione)—COCl | Oily material | νC=O | 1790, 1720, 1680 |
| CH$_3$CH$_2$—N(piperazine-2,3-dione, 5-CH$_3$)—COCl | m.p. 65 – 70° C (decomp.) | νC=O | 1785, 1680 |

Table 2-continued

Reactive derivatives of (III)

$$A-N\underset{(R^2R^3)_m}{\overset{(X)_n}{\diamond}}N-\underset{\overset{\|}{Y}}{C}OH$$

| Compound | Physical property | I.R. (cm$^{-1}$) | |
|---|---|---|---|
| CH$_3$CH$_2$-N(piperazinedione)-CCSCl | m.p. 100 – 101° C (decomp.) | νC=O | 17225, 1675 |
| (spiro cyclohexane piperazinedione with HN and N-COCl) | m.p. 180 – 181° C | νC=O | 1740, 1695 |
| (benzyl-CH$_2$-N spiro cyclohexane piperazinedione N-COCl) | m.p. 160 – 165° C | νC=O | 1740, 1670 |
| Cl$_3$CCH$_2$OCO-N (spiro cyclohexane piperazinedione) N-COCl | Oily material | νC=O | 1800, 1750, 1710 |
| HN (piperazinedione) N-COCl | m.p. 185 – 187° C (decomp.) | νC=O | 1730, 1690 |
| HN (phenyl, CH$_3$ substituted piperazinedione) N-COCl | Oily material | νC=O | 1750, 1710 – 1685 |
| (benzyl)-CH$_2$-N (phenyl, CH$_3$ substituted piperazinedione) N-COCl | " | νC=O | 1735, 1725, 1710, 1675 |

Note:
Et$_2$O = CH$_3$CH$_2$OCH$_2$CH$_3$
AcOBu = CH$_3$COO(CH$_2$)$_3$CH$_3$

The compound represented by the general formula (V) can be easily obtained by reacting, for example, a salt with an alkali metal, an alkaline earth metal or a nitrogen-containing organic base of an amino acid (VII) (any of the D-isomer, L-isomer and racemic compound) represented by the general formula (VII)

$$H_2N-R-COOH \quad (VII)$$

wherein R is as defined previously, with a reactive derivative in the (thio)carboxyl group of a compound represented by the general formula (III) in a solvent inert to the reaction in the presence of an acid-binding agent. Preferred examples of the compound of formula (V) are D-isomers, L-isomers and racemic compounds of the following compounds, though, of course, the examples are not limitative:

α-(4-Acetyl-2-oxo-1-piperazinocarbonylamino)-phenylacetic acid
α-(4-Chloroacetyl-2-oxo-1-piperazinocarbonylamino)-phenylacetic acid
α-(4-Dichloroacetyl-2-oxo-1-piperazinocarbonylamino)phenylacetic acid
α-(4-Palmitoyl-2-oxo-1-piperazinocarbonylamino)-phenylacetic acid
α-(4-Caproyl-2-oxo-1-piperazinocarbonylamino)-phenylacetic acid
α-(4-Capryloyl-2-oxo-1-piperazinocarbonylamino)-phenylacetic acid
α-(4-Enanthoyl-2-oxo-1-piperazinocarbonylamino)-phenylacetic acid
α-(4-Cyclohexanecarbonyl-2-oxo-1-piperazinocarbonylamino)phenylacetic acid
α-(4-Benzoyl-2-oxo-1-piperazinocarbonylamino)-phenylacetic acid
α-(4-p-Chlorobenzoyl-2-oxo-1-piperazinocarbonylamino)phenylacetic acid
α-(4-p-Methoxybenzoyl-2-oxo-1-piperazinocarbonylamino)phenylacetic acid
α-[4-(3,4,5-Trimethoxybenzoyl)-2-oxo-1-piperazinocarbonylamino]phenylacetic acid
α-[4-(2,4-Dichlorobenzoyl)-2-oxo-1-piperazinocarbonylamino]phenylacetic acid
α-(4-Acetyl-3-methyl-2-oxo-1-piperazinocarbonylamino)phenylacetic acid
α-(4-Methanesulfonyl-2-oxo-1-piperazinocarbonylamino)phenylacetic acid
α-(4-Acetylaminocarbonyl-2-oxo-1-piperazinocarbonylamino)phenylacetic acid
α-(4-Phenylaminocarbonyl-2-oxo-1-piperazinocarbonylamino)phenylacetic acid
α-(4-Ethoxycarbonyl-2-oxo-1-piperazinocarbonylamino)phenylacetic acid
α-(4-Pivaloyloxymethyl-2-oxo-1-piperazinocarbonylamino)phenylacetic acid
α-(4-n-Hexyl-2-oxo-1-piperazinocarbonylamino)-phenylacetic acid
α-(4-n-Butyl-2-oxo-1-piperazinocarbonylamino)-phenylacetic acid
α-(4-n-Butyl-6-methyl-2-oxo-1-piperazinocarbonylamino)phenylacetic acid
α-(4-n-Octyl-2-oxo-1-piperazinocarbonylamino)-phenylacetic acid
α-(3-Oxo-1-piperazinocarbonylamino)phenylacetic acid
α-(2,5-Dimethyl-3-oxo-1-piperazinocarbonylamino)-phenylacetic acid
α-(5-Methyl-3-oxo-1-piperazinocarbonylamino)-phenylacetic acid
α-(2-Ethoxycarbonylmethyl-3-oxo-1-piperazinocarbonylamino)phenylacetic acid
α-(2-Methyl-3-oxo-1-piperazinocarbonylamino)-phenylacetic acid
α-(4-Acetyl-2-methyl-3-oxo-1-piperazinocarbonylamino)phenylacetic acid
α-(4-Phenylaminocarbonyl-3-oxo-1-piperazinocarbonylamino)phenylacetic acid
α-(4-Methyl-3-oxo-1-piperazinocarbonylamino)-phenylacetic acid
α-(4-n-Butyl-3-oxo-1-piperazinocarbonylamino)-phenylacetic acid
α-(4-Ethyl-3-oxo-1-piperazinocarbonylamino)-phenylacetic acid
α-(4-Isopropyl-3-oxo-1-piperazinocarbonylamino)-phenylacetic acid
α-(4-n-Pentyl-3-oxo-1-piperazinocarbonylamino)-phenylacetic acid
α-(4-iso-Pentyl-3-oxo-1-piperazinocarbonylamino)-phenylacetic acid
α-(4-n-Hexyl-3-oxo-1-piperazinocarbonylamino)-phenylacetic acid
α-(4-n-Heptyl-3-oxo-1-piperazinocarbonylamino)-phenylacetic acid
α-(4-n-Octyl-3-oxo-1-piperazinocarbonylamino)-phenylacetic acid
α-(4-n-Dodecyl-3-oxo-1-piperazinocarbonylamino)-phenylacetic acid
α-(4-Cyclopentyl-3-oxo-1-piperazinocarbonylamino)-phenylacetic acid
α-(2-Methyl-4-n-butyl-3-oxo-1-piperazinocarbonylamino)phenylacetic acid
α-(4-n-Butyl-5-methyl-3-oxo-1-piperazinocarbonylamino)phenylacetic acid
α-(4-n-Butyl-6-methyl-3-oxo-1-piperazinocarbonylamino)phenylacetic acid
α-(2-Phenyl-3-oxo-1-piperazinocarbonylamino)-phenylacetic acid
α-(4-Benzyl-3-oxo-1-piperazinocarbonylamino)-phenylacetic acid
α-(4-Carbamoyl-2-methyl-3-oxo-1-piperazinocarbonylamino)phenylacetic acid
α-(4-β-Hydroxyethyl-3-oxo-1-piperazinocarbonylamino)phenylacetic acid
α-(4-Allyl-3-oxo-1-piperazinocarbonylamino)-phenylacetic acid
α-(4-α-Methylallyl-3-oxo-1-piperazinocarbonylamino)phenylacetic acid
α-(4-β-Methylallyl-3-oxo-1-piperazinocarbonylamino)-phenylacetic acid
α-[4-(Trans-2-butenyl)-3-oxo-1-piperazinocarbonylamino]phenylacetic acid
α-(4-Morpholinomethyl-3-oxo-1-piperazinocarbonylamino)phenylacetic acid
α-(4-Ethyl-3-oxo-1-piperazinocarbonylamino)propionic acid
α-(4-Acetyl-2,5-dioxo-1-piperazinocarbonylamino)-phenylacetic acid
α-(4-Benzoyl-2,5-dioxo-1-piperazinocarbonylamino)-phenylacetic acid
α-(4-Methyl-2,5-dioxo-1-piperazinocarbonylamino)-phenylacetic acid
α-(4-Benzyl-2,5-dioxo-1-piperazinocarbonylamino)-phenylacetic acid
α-(4-Methyl-2,3-dioxo-1-piperazinocarbonylamino)-phenylacetic acid
α-(4-Acetoxyethyl-2,3-dioxo-1-piperazinocarbonylamino)phenylacetic acid
α-(4-Ethyl-2,3-dioxo-1-piperazinocarbonylamino)-phenylacetic acid
α-(4-n-Propyl-2,3-dioxo-1-piperazinocarbonylamino)phenylacetic acid
α-(4-n-Butyl-2,3-dioxo-1-piperazinocarbonylamino)-phenylacetic acid
α-(4-Isopropyl-2,3-dioxo-1-piperazinocarbonylamino)phenylacetic acid
α-(4-n-Pentyl-2,3-dioxo-1-piperazinocarbonylamino)-phenylacetic acid
α-(4-n-Hexyl-2,3-dioxo-1-piperazinocarbonylamino)-phenylacetic acid α-(4-n-Heptyl-2,3-dioxo-1-piperazinocarbonylamino)phenylacetic acid
α-(4-n-Octyl-2,3-dioxo-1-piperazinocarbonylamino)phenylacetic acid
α-(4-Allyl-2,3-dioxo-1-piperazinocarbonylamino)phenylacetic acid
α-(4-Phenyl-2,3-dioxo-1-piperazinocarbonylamino)phenylacetic acid
α-(4-β-Chloroethyl-2,3-dioxo-1-piperazinocarbonylamino)phenylacetic acid
α-(4-Pyrrolidinoethyl-2,3-dioxo-1-piperazinocarbonylamino)phenylacetic acid
α-(4-Methyl-2,3-dioxo-1-piperazinocarbonylamino)-p-hydroxyphenylacetic acid
α-(4-Ethyl-2,3-dioxo-1-piperazinocarbonylamino)-p-hydroxyphenylacetic acid
α-(6-Methyl-4-ethyl-2,3-dioxo-1-piperazinocarbonylamino)phenylacetic acid
α-(4,6-Dimethyl-2,3-dioxo-1-piperazinocarbonylamino)phenylacetic acid
α-(4-Ethyl-2,3-dioxo-1-piperazinothiocarbonylamino)phenylacetic acid
α-(4-Methyl-2,3-dioxo-1-piperazinocarbonylamino)-1,4-cyclohexadienylacetic acid
α-(4-Ethyl-2,3-dioxo-1-piperazinocarbonylamino)-1,4-cyclohexadienylacetic acid
α-(4-n-Propyl-2,3-dioxo-1-piperazinocarbonylamino)-1,4-cyclohexadienylacetic acid
α-(4-n-Butyl-2,3-dioxo-1-piperazinocarbonylamino)-1,4-cyclohexadienylacetic acid
α-(4-Methyl-2,3-dioxo-1-piperazinocarbonylamino)-2-thienylacetic acid
α-(4-Ethyl-2,3-dioxo-1-piperazinocarbonylamino)-2-thienylacetic acid
α-(4-n-Propyl-2,3-dioxo-1-piperazinocarbonylamino)-2-thienylacetic acid
α-(4-n-Butyl-2,3-dioxo-1-piperazinocarbonylamino)-2-thienylacetic acid
α-(2,2-Pentamethylene-3,5-dioxo-1-piperazinocarbonylamino)phenylacetic acid
α-(4-Benzyl-2,2-pentamethylene-3,5-dioxo-1-piperazinocarbonylamino)phenylacetic acid
α-(4-β,β,β-Trichloroethoxycarbonyl-2,2-pentamethylene-3,5-dioxo-1-piperazinocarbonylamino)phenylacetic acid
α-(3,5-Dioxo-1-piperazinocarbonylamino)phenylacetic acid
α-(2-Methyl-2-phenyl-3,5-dioxo-1-piperazinocarbonylamino)phenylacetic acid
α-(4-Benzyl-2-methyl-3,5-dioxo-1-piperazinocarbonylamino)phenylacetic acid
α-(4-Methyl-2,3-dioxo-1-piperazinocarbonylamino)phenylacetic acid As the reactive derivative in the carboxyl group of the compound represented by the general formula (V), there is used a reactive derivative of a carboxylic acid which is ordinarily used in the synthesis of acid amides. Suitable reactive derivatives include, for example, acid halides, acid anhydrides, mixed acid anhydrides with organic or inorganic acids, active acid amides, acid cyanides, active esters, etc. Particularly, acid chlorides, mixed acid anhydrides and active acid amides are preferred. Examples of the mixed acid anhydrides are mixed acid anhydrides with substituted acetic acids, alkyl carbonic acids, aryl carbonic acids and aralkyl carbonic acids; examples of the active esters are cyanomethyl esters, substituted phenyl esters, substituted benzyl esters, substituted thienyl esters, etc.; and examples of the active acid amides are N-acyl saccharins, N-acyl imidazoles, N-acyl benzoylamides, N,N-dicyclohexyl-N-acylureas, N-acyl sulfonamides, etc.

Compounds of formula (VI) can be obtained by, for example, process (1) or (2). Some of the compounds obtained by process (3) can further be used as the starting compounds in process (3). Any of the D-, L- and racemic compounds of formula (VI) may be used.

The modes of practice of the processes (1), (2) and (3) are explained below.

The processes (1) and (2) may be carried out under substantially the same conditions. That is, the compound of formula (II) or (IV) is dissolved or suspended in at least one inert solvent selected from, for example, water, acetone, tetrahydrofuran, dioxane, acetonitrile, dimethylformamide, methanol, ethanol, methoxyethanol, diethyl ether, isopropyl ether, benzene, toluene, methylene chloride, chloroform, ethyl acetate, methyl isobutyl ketone and the like. The resulting solution or suspension is reacted with a reactive derivative of the compound of formula (III), or with the compound of formula (V) or a reactive derivative in the carboxyl group of the compound of formula (V) in the presence or absence of a base at a temperature in the range from $-60°$ to $80°$ C., preferably from $-40°$ to $30°$ C. The reaction time is ordinarily 5 minutes to 5 hours. Examples of the base used in the above reaction are inorganic bases such as alkali hydroxides, alkali hydrogencarbonates, alkali carbonates, alkali acetates, etc.; tertiary amines such as trimethylamine, triethylamine, tributylamine, pyridine, N-methylpiperidine, N-methylmorpholine, lutidine, collidine, etc.; and secondary amines such as dicyclohexylamine, diethylamine, etc. When the compound of formula (V) is used in the form of a free acid or salt in the process (2), the reaction of the process (2) may be effected in the presence of a dehydrating condensing agent such as N,N-dicyclohexyl carbodiimide, N-cyclohexyl-N'-morpholinoethyl carbodiimide, N,N'-diethyl carbodiimide, N,N'-carbonyl di(2-methylimidazole), a trialkyl ester of phosphorous acid, ethyl ester of polyphosphoric acid, phosphorus oxychloride, phosphorus trichloride, 2-chloro-1,3,2-dioxaphospholane or oxazolyl chloride. Suitable salts of the compound of formula (V) include alkali metal salts, alkaline earth metal salts, ammonium salts, and salts with organic bases such as trimethylamine, dicyclohexylamine and the like.

The process (3) is carried out in the manner described below.

When B in the formula (VI) is a group other than a hetero aromatic N-oxide thio group having a thio group on the carbon atom adjacent to the N-oxide group in the molecule, the compound of formula (VI) is reacted with the compound of formula (VII) or a tertiary amine in at least one solvent selected from, for example, water, methanol, ethanol, propanol, isopropanol, butanol, acetone, methyl ethyl ketone, methyl isobutyl ketone, tetrahydrofuran, dioxane, acetonitrile, ethyl acetate, methoxyethanol, dimethoxyethane, dimethylformamide, dimethyl sulfoxide, dichloromethane, chloroform, a dichloroethane, and the like. The above-mentioned reaction is preferably effected in a strongly polar solvent such as water or the like. In this case, the pH of the reaction solution is advantageously maintained at 2 to 10, preferably 4 to 8. The desired pH may be attained by addition of a buffer solution such as sodium phosphate. The reaction conditions are not particularly limited, though the reaction is ordinarily conducted at 0° to 100°

C. over a period of several hours to tens hours. When B in the formula (VI) is a hetero aromatic N-oxide thio group having a thio group on the carbon atom adjacent to the N-oxide group in the molecule, the compound of formula (VI) is reacted with the compound of formula (VII) in the above-mentioned solvent in the presence of a cupric compound. This reaction is particularly useful where an alcohol is used such as methyl alcohol, ethyl alcohol, propyl alcohol, isopropyl alcohol, n-butyl alcohol, benzyl alcohol, ethylene glycol or the like as the compound of formula (VII). In this case, the reaction proceeds smoothly by using an excess of the alcohol per se to allow it to act as the reaction medium too. Suitable cupric compounds used in this process include organic and inorganic ones, such as cupric chloride, bromide, fluoride, nitrate, sulfate, borate, phosphate, cyanide, formate, acetate, propionate, citrate, tartarate, benzoate, salicylate and the like. The amount of the cupric compound used is preferably ½ mole per mole of the compound of formula (VI). The reaction temperature and the reaction time may be varied depending upon the nature of the compound of formula (VI), the cupric compound and the compound of formula (VII), though they are usually selected from the range of 0° to 100° C. and the range of several minutes to several days, respectively.

The reaction conditions to be adopted in the processes (1), (2) and (3) are not limited to those mentioned above, and can be properly varied depending upon the kinds of reaction reagents.

Further, the non-toxic salts of the general formula (I), in which $R^1$ is a salt-forming cation, can be easily obtained according to an ordinary procedure from compounds of the general formula (I), in which $R^1$ is a hydrogen atom or a blocking group.

Thus, among the compounds of formula (I) of the present invention, the penicillins can be easily obtained according to any of the aforesaid processes (1) and (2), while the cephalosporins can be easily obtained according to anyone of the aforesaid processes (1), (2) and (3).

The present penicillins and cephalosporins include the following compounds though are not restricted thereto. The following penicillins can be produced by any of the aforesaid processes (1) and (2), and the following cephalosporins can be produced by any of the aforesaid processes (1), (2) and (3). Penicillins:

6-[D(−)-α-(4-acetyl-2-oxo-1-piperazinocarbonylamino)-phenylacetamido]penicillanic acid,
6-[D(−)-α-(4-dichloroacetyl-2-oxo-1-piperazinocarbonylamino)phenylacetamido]penicillanic acid,
6-[D(−)-α-(4-enanthoyl-2-oxo-1-piperazinocarbonylamino)phenylacetamido]penicillanic acid,
6-[D(−)-α-(4-cyclohexanecarbonyl-2-oxo-1-piperazinocarbonylamino)phenylacetamido]penicillanic acid,
6-[D(−)-α-(4-acetyl-3-methyl-2-oxo-1-piperazinocarbonylamino)phenylacetamido]penicillanic acid,
6-[D(−)-α-(4-methanesulfonyl-2-oxo-1-piperazinocarbonylamino)phenylacetamido]penicillanic acid,
6-[D(−)-α-(4-n-hexyl-2-oxo-1-piperazinocarbonylamino)-phenylacetamido]penicillanic acid,
6-[D(−)-α-(4-n-butyl-2-oxo-1-piperazinocarbonylamino)-phenylacetamido]penicillanic acid,
6-[D(−)-α-(4-n-butyl-6-methyl-2-oxo-1-piperazinocarbonylamino)phenylacetamido]penicillanic acid,
6-[D(−)-α-(4-n-octyl-2-oxo-1-piperazinocarbonylamino)phenylacetamido]penicillanic acid,
6-[D(−)-α-(4-pivaloyloxymethyl-2-oxo-1-piperazinocarbonylamino)phenylacetamido]penicillanic acid,
6-[D(−)-α-(4-palmitoyl-2-oxo-1-piperazinocarbonylamino)phenylacetamido]penicillanic acid,
6-[D(−)-α-(4-capryloyl-2-oxo-1-piperazinocarbonylamino)phenylacetamido]penicillanic acid,
6-[D(−)-α-(4-caproyl-2-oxo-1-piperazinocarbonylamino)-phenylacetamido]penicillanic acid,
6-[D(−)-α-(4-chloroacetyl-2-oxo-1-piperazinocarbonylamino)phenylacetamido]penicillanic acid,
6-[D(−)-α-(4-benzoyl-2-oxo-1-piperazinocarbonylamino)phenylacetamido]penicillanic acid,
6-[D(−)-α-(4-p-chlorobenzoyl-2-oxo-1-piperazinocarbonylamino)phenylacetamido]penicillanic acid,
6-[D(−)-α-(4-p-methoxybenzoyl-2-oxo-1-piperazinocarbonylamino)phenylacetamido]penicillanic acid,
6-{D(−)-α-[4-(3,4,5-trimethoxybenzoyl)-2-oxo-1-piperazinocarbonylamino]phenylacetamido}·penicillanic acid,
6-{D(−)-α-[4-(2,4-dichlorobenzoyl)-2-oxo-1-piperazinocarbonylamino]phenylacetamido}·penicillanic acid,
6-[D(−)-α-(4-acetylaminocarbonyl-2-oxo-1-piperazinocarbonylamino)phenylacetamido]penicillanic acid,
6-[D(−)-α-(4-phenylaminocarbonyl-2-oxo-1-piperazinocarbonylamino)phenylacetamido]penicillanic acid,
6-[D(−)-α-(4-ethoxycarbonyl-2-oxo-1-piperazinocarbonylamino)phenylacetamido]penicillanic acid,
6-[D(−)-α-(4-methyl-3-oxo-1-piperazinocarbonylamino)-phenylacetamido]penicillanic acid,
6-[D(−)-α-(4-n-butyl-3-oxo-1-piperazinocarbonylamino)-phenylacetamido]penicillanic acid,
6-[D(−)-α-(4-ethyl-3-oxo-1-piperazinocarbonylamino)-phenylacetamido]penicillanic acid,
6-[D(−)-α-(4-isopropyl-3-oxo-1-piperazinocarbonylamino)phenylacetamido]penicillanic acid,
6-[D(−)-α-(4-n-pentyl-3-oxo-1-piperazinocarbonylamino)phenylacetamido]penicillanic acid,
6-[D(−)-α-(4-iso-pentyl-3-oxo-1-piperazinocarbonylamino)phenylacetamido]penicillanic acid,
6-[D(−)-α-(2-methyl-4-n-butyl-3-oxo-1-piperazinocarbonylamino)phenylacetamido]penicillanic acid,
6-[D(−)-α-(4-n-butyl-5-methyl-3-oxo-1-piperazinocarbonylamino)phenylacetamido]penicillanic acid,
6-[D(−)-α-(4-n-butyl-6-methyl-3-oxo-1-piperazinocarbonylamino)phenylacetamido]penicillanic acid,
6-[D(−)-α-(4-benzyl-3-oxo-1-piperazinocarbonylamino)-phenylacetamido]penicillanic acid,
6-[D(−)-α-(4-β-hydroxyethyl-3-oxo-1-piperazinocarbonylamino)phenylacetamido]penicillanic acid,
6-[D(−)-α-(4-acetyl-2-methyl-3-oxo-1-piperazinocarbonylamino)phenylacetamido]penicillanic acid,
6-[D(−)-α-(4-carbamoyl-2-methyl-3-oxo-1-piperazinocarbonylamino)phenylacetamido]penicillanic acid, 6-[D(—)-α-(3-oxo-1-piperazinocarbonylamino)-phenylacetamido]penicillanic acid,
6-[D(—)-α-(2,5-dimethyl-3-oxo-1-piperazinocarbonylamino)phenylacetamido]penicillanic acid,
6-[D(—)-α-(5-methyl-3-oxo-1-piperazinocarbonylamino)-phenylacetamido]penicillanic acid,
6-[D(—)-α-(2-ethoxycarbonylmethyl-3-oxo-1-piperazinocarbonylamino)phenylacetamido]-penicillanic acid,
6-[D(—)-α-(2-methyl-3-oxo-1-piperazinocarbonylamino)-phenylacetamido]penicillanic acid,
6-[D(—)-α-(4-ethyl-3-oxo-1-piperazinocarbonylamino)-propionamido]penicillanic acid,
6-[D(—)-α-(4-allyl-3-oxo-1-piperazinocarbonylamino)-phenylacetamido]penicillanic acid,
6-[D(—)-α-(4-α-methylallyl-3-oxo-1-piperazinocarbonylamino)phenylacetamido]penicillanic acid,
6-[D(—)-α-(4-β-methylallyl-3-oxo-1-piperazinocarbonylamino)phenylacetamido]penicillanic acid,
6-{D(—)-α-[4-(trans-2-butenyl)-3-oxo-1-piperazinocarbonylamino]phenylacetamido}·penicillanic acid,
6-[D(—)-α-(4-n-hexyl-3-oxo-1-piperazinocarbonylamino)phenylacetamido]penicillanic acid,
6-[D(—)-α-(4-n-heptyl-3-oxo-1-piperazinocarbonylamino)phenylacetamido]penicillanic acid,
6-[D(—)-α-(4-n-octyl-3-oxo-1-piperazinocarbonylamino)-phenylacetamido]penicillanic acid,
6-[D(—)-α-(4-n-dodecyl-3-oxo-1-piperazinocarbonylamino)phenylacetamido]penicillanic acid,
6-[D(—)-α-(4-cyclopentyl-3-oxo-1-piperazinocarbonylamino)phenylacetamido]penicillanic acid,
6-[D(—)-α-(4-phenylaminocarbonyl-3-oxo-1-piperazinocarbonylamino)phenylacetamido]-penicillanic acid,
6-[D(—)-α-(2-phenyl-3-oxo-1-piperazinocarbonylamino)phenylacetamido]penicillanic acid,
6-[D(—)-α-(4-morpholinomethyl-3-oxo-1-piperazinocarbonylamino)phenylacetamido]-penicillanic acid,
6-[D(—)-α-(4-acetyl-2,5-dioxo-1-piperazinocarbonylamino)phenylacetamido]penicillanic acid,
6-[D(—)-α-(4-benzoyl-2,5-dioxo-1-piperazinocarbonylamino)phenylacetamido]penicillanic acid,
6-[D(—)-α-(4-methyl-2,5-dioxo-1-piperazinocarbonylamino)phenylacetamido]penicillanic acid,
6-[D(—)-α-(4-benzyl-2,5-dioxo-1-piperazinocarbonylamino)phenylacetamido]penicillanic acid,
6-[D(—)-α-(4-ethyl-2,3-dioxo-1-piperazinocarbonylamino)phenylacetamido]penicillanic acid,
6-[D(—)-α-(4-methyl-2,3-dioxo-1-piperazinocarbonylamino)phenylacetamido]penicillanic acid,
6-[D(—)-α-(4-n-propyl-2,3-dioxo-1-piperazinocarbonylamino)phenylacetamido]penicillanic acid,
6-[D(—)-α-(4-n-butyl-2,3-dioxo-1-piperazinocarbonylamino)phenylacetamido]penicillanic acid,
6-[D(—)-α-(4-iso-propyl-2,3-dioxo-1-piperazinocarbonylamino)phenylacetamido]penicillanic acid,
6-[D(—)-α-(4-acetoxyethyl-2,3-dioxo-1-piperazinocarbonylamino)phenylacetamido]-penicillanic acid,
6-[D(—)-α-(4-allyl-2,3-dioxo-1-piperazinocarbonylamino)phenylacetamido]penicillanic acid,
6-[D(—)-α-(4-phenyl-2,3-dioxo-1-piperazinocarbonylamino)phenylacetamido]penicillanic acid,
6-[D(—)-α-(4-β-chloroethyl-2,3-dioxo-1-piperazinocarbonylamino)phenylacetamido]-penicillanic acid,
6-[D(—)-α-(6-methyl-4-ethyl-2,3-dioxo-1-piperazinocarbonylamino)phenylacetamido]-penicillanic acid,
6-[D(—)-α-(4,6-dimethyl-2,3-dioxo-1-piperazinocarbonylamino)phenylacetamido]penicillanic acid,
6-[D(—)-α-(4-n-pentyl-2,3-dioxo-1-piperazinocarbonylamino)phenylacetamido]penicillanic acid,
6-[D(—)-α-(4-n-hexyl-2,3-dioxo-1-piperazinocarbonylamino)phenylacetamido]penicillanic acid,
6-[D(—)-α-(4-n-heptyl-2,3-dioxo-1-piperazinocarbonylamino)phenylacetamido]penicillanic acid,
6-[D(—)-α-(4-n-octyl-2,3-dioxo-1-piperazinocarbonylamino)phenylacetamido]penicillanic acid,
6-[D(—)-α-(4-ethyl-2,3-dioxo-1-piperazinothiocarbonylamino)phenylacetamido]penicillanic acid,
6-[D(—)-α-(4-methyl-2,3-dioxo-1-piperazinocarbonylamino)-p-hydroxyphenylacetamido]penicillanic acid,
6-[D(—)-α-(4-ethyl-2,3-dioxo-1-piperazinocarbonylamino)-p-hydroxyphenylacetamido]penicillanic acid,
6-[D(—)-α-(4-methyl-2,3-dioxo-1-piperazinocarbonylamino)-1,4-cyclohexadienylacetamido]-penicillanic acid,
6-[D(—)-α-(4-ethyl-2,3-dioxo-1-piperazinocarbonylamino)-1,4-cyclohexadienylacetamido]-penicillanic acid,
6-[D(—)-α-(4-n-propyl-2,3-dioxo-1-piperazinocarbonylamino)-1,4-cyclohexadienylacetamido]-penicillanic acid,
6-[D(—)-α-(4-n-butyl-2,3-dioxo-1-piperazinocarbonylamino)-1,4-cyclohexadienylacetamido]-penicillanic acid,
6-[DL-α-(4-methyl-2,3-dioxo-1-piperazinocarbonylamino)-2-thienylacetamido]penicillanic acid,
6-[DL-α-(4-ethyl-2,3-dioxo-1-piperazinocarbonylamino)-2-thienylacetamido]penicillanic acid,
6-[DL-α-(4-n-propyl-2,3-dioxo-1-piperadinocarbonylamino)-2-thienylacetamido]penicillanic acid,
6-[DL-α-(4-n-butyl-2,3-dioxo-1-piperazinocarbonylamino)-2-thienylacetamido]penicillanic acid,
6-[D(—)-α-(2,2-pentamethylene-3,5-dioxo-1-piperazinocarbonylamino)phenylacetamido]-penicillanic acid,
6-[D(—)-α-(3,5-dioxo-1-piperazinocarbonylamino)-phenylacetamido]penicillanic acid,
6-[D(—)-α-(2-methyl-2-phenyl-3,5-dioxo-1-piperazinocarbonylamino)phenylacetamido]-penicillanic acid,
6-[D(—)-α-(4-benzyl-2,2-pentamethylene-3,5-dioxo-1-piperazinocarbonylamino)phenylacetamido]-penicillanic acid,
6-[D(—)-α-(4-β,β,β-trichloroethoxycarbonyl-2,2-pentamethylene-3,5-dioxo-1-piperazinocarbonylamino)phenylacetamido]penicillanic acid,
6-[D(—)-α-(4-benzyl-2-methyl-2-phenyl-3,5-dioxo-1-piperazinocarbonylamino)phenylacetamido]-penicillanic acid,
pivaloyloxymethyl 6-[D(—)-α-(2-methyl-3-oxo-1-piperazinocarbonylamino)phenylacetamido]-penicillanate,
phthalidyl 6-[D(—)-α-(4-methyl-2,3-dioxo-1-piperazinocarbonylamino)phenylacetamido]-penicillanate,
phthalidyl 6-[D(—)-α-(4-ethyl-2,3-dioxo-1-piperazinocarbonylamino)phenylacetamido]-penicillanate, phthalidyl 6-[D(—)-α-(4-iso-propyl-2,3-dioxo-1-piperazinocarbonylamino)phenylacetamido]-penicillanate,
phthalidyl 6-[D(—)-α-(4-n-butyl-2,3-dioxo-1-piperazinocarbonylamino)phenylacetamido]-penicillanate,
methoxymethyl 6-[D(—)-α-(4-methyl-2,3-dioxo-1-piperazinocarbonylamino)phenylacetamido]-penicillanate,
methoxymethyl 6-[D(—)-α-(4-ethyl-2,3-dioxo-1-piperazinocarbonylamino)phenylacetamido]-penicillanate,
methoxymethyl 6-[D(—)-α-(4-n-butyl-2,3-dioxo-1-piperazinocarbonylamino)phenylacetamido]-penicillanate,
methoxymethyl 6-[D(—)-α-(4-iso-propyl-2,3-dioxo-1-piperazinocarbonylamino)phenylacetamido]-penicillanate,
methoxymethyl 6-[D(—)-α-(4-n-octyl-2,3-dioxo-1-piperazinocarbonylamino)phenylacetamido]-penicillanate,
pivaloyloxymethyl 6-[D(—)-α-(4-methyl-2,3-dioxo-1-piperazinocarbonylamino)phenylacetamido]-penicillanate,
pivaloyloxymethyl 6-[D(—)-α-(4-ethyl-2,3-dioxo-1-piperazinocarbonylamino)phenylacetamido]-penicillanate,
pivaloyloxymethyl 6-[D(—)-α-(4-n-octyl-2,3-dioxo-1-piperazinocarbonylamino)phenylacetamido]-penicillanate,
β-piperidinoethyl 6-[D(—)-α-(4-methyl-2,3-dioxo-1-piperazinocarbonylamino)phenylacetamido]-penicillanate,
β-piperidinoethyl 6-[D(—)-α-(4-n-octyl-2,3-dioxo-1-piperazinocarbonylamino)phenylacetamido]-penicillanate,
β-morpholinoethyl 6-[D(—)-α-(4-methyl-2,3-dioxo-1-piperazinocarbonylamino)phenylacetamido]-penicillanate,
β-morpholinoethyl 6-[D(—)-α-(4-n-octyl-2,3-dioxo-1-piperazinocarbonylamino)phenylacetamido]-penicillanate, etc.

Cephalosporins:
7-[D(—)-α-(4-methyl-2,3-dioxo-1-piperazinocarbonylamino)phenylacetamido]-3-methyl-Δ³-cephem-4-carboxylic acid,
7-[D(—)-α-(4-ethyl-2,3-dioxo-1-piperazinocarbonylamino)phenylacetamido]-3-methyl-Δ³-cephem-4-carboxylic acid,
7-[D(—)-α-(4-n-propyl-2,3-dioxo-1-piperazinocarbonylamino)phenylacetamido]-3-methyl-Δ³-cephem-4-carboxylic acid,
7-[D(—)-α-(4-n-butyl-2,3-dioxo-1-piperazinocarbonylamino)phenylacetamido]-3-methyl-Δ³-cephem-4-carboxylic acid,
7-[D(—)-α-(4-n-pentyl-2,3-dioxo-1-piperazinocarbonylamino)phenylacetamido]-3-methyl-Δ³-cephem-4-carboxylic acid,
7-[D(—)-α-(4-n-hexyl-2,3-dioxo-1-piperazinocarbonylamino)phenylacetamido]-3-methyl-Δ³-cephem-4-carboxylic acid,
7-[D(—)-α-(4-n-heptyl-2,3-dioxo-1-piperazinocarbonylamino)phenylacetamido]-3-methyl-Δ³-cephem-4-carboxylic acid,
7-[D(—)-α-(4-n-octyl-2,3-dioxo-1-piperazinocarbonylamino)phenylacetamido]-3-methyl-Δ³-cephem-4-carboxylic acid,
7-[D(—)-α-(4-methyl-2,3-dioxo-1-piperazinocarbonylamino)phenylacetamido]-3-acetoxymethyl-Δ³-cephem-4-carboxylic acid,
7-[D(—)-α-(4-n-propyl-2,3-dioxo-1-piperazinocarbonylamino)phenylacetamido]-3-acetoxymethyl-Δ³-cephem-4-carboxylic acid,
7-[D(—)-α-(4-ethyl-2,3-dioxo-1-piperazinocarbonylamino)phenylacetamido]-3-acetoxymethyl-Δ³-cephem-4-carboxylic acid,
7-[D(—)-α-(4-iso-propyl-2,3-dioxo-1-piperazinocarbonylamino)phenylacetamido]-3-acetoxymethyl-Δ³-cephem-4-carboxylic acid,
7-[D(—)-α-(4-ethyl-2,3-dioxo-1-piperazinothiocarbonylamino)phenylacetamido]-3-acetoxymethyl-Δ³-cephem-4-carboxylic acid,
7-[D(—)-α-(4-methyl-2,3-dioxo-1-piperazinothiocarbonylamino)phenylacetamido]-3-acetoxymethyl-Δ³-cephem-4-carboxylic acid,
7-[D(—)-α-(4-methyl-2,3-dioxo-1-piperazinocarbonylamino)phenylacetamido]-3-[2-(5-methyl-1,3,4-thiadiazolyl)-thiomethyl]-Δ³-cephem-4-carboxylic acid,
7-[D(—)-α-(4-ethyl-2,3-dioxo-1-piperazinocarbonylamino)phenylacetamido]-3-[2-(5-methyl-1,3,4-thiadiazolyl)-thiomethyl]-Δ³-cephem-4-carboxylic acid,
7-[D(—)-α-(4-n-propyl-2,3-dioxo-1-piperazinocarbonylamino)phenylacetamido]-3-[2-(5-methyl-1,3,4-thiadiazolyl)-thiomethyl]-Δ³-cephem-4-carboxylic acid,
7-[D(—)-α-(4-n-butyl-2,3-dioxo-1-piperazinocarbonylamino)phenylacetamido]-3-[2-(5-methyl-1,3,4-thiadiazolyl)-thiomethyl]-Δ³-cephem-4-carboxylic acid,
7-[D(—)-α-(4-phenyl-2,3-dioxo-1-piperazinocarbonylamino)phenylacetamido]-3-[2-(5-methyl-1,3,4-thiadiazolyl)-thiomethyl]-Δ³-cephem-4-carboxylic acid,
7-[D(—)-α-(4-methyl-2,3-dioxo-1-piperazinocarbonylamino)phenylacetamido]-3-[5-(1-methyl-1,2,3,4-tetrazolyl)-thiomethyl]-Δ³-cephem-4-carboxylic acid,
7-[D(—)-α-(4-ethyl-6-methyl-2,3-dioxo-1-piperazinocarbonylamino)phenylacetamido]-3-[5-(1-methyl-1,2,3,4-tetrazolyl)-thiomethyl]-Δ³-cephem-4-carboxylic acid,
7-[D(—)-α-(4,6-dimethyl-2,3-dioxo-1-piperazinocarbonylamino)phenylacetamido]-3-[5-(1-methyl-1,2,3,4-tetrazolyl)-thiomethyl]-Δ³-cephem-4-carboxylic acid,
7-[D(—)-α-(4-phenyl-2,3-dioxo-1-piperazinocarbonylamino)phenylacetamido]-3-[5-(1-methyl-1,2,3,4-tetrazolyl)-thiomethyl]-Δ³-cephem-4-carboxylic acid,
7-[D(—)-α-(4-methyl-2,3-dioxo-1-piperazinocarbonylamino)phenylacetamido]-3-[5-(1,3,4-thiadiazolyl)-thiomethyl]-Δ³-cephem-4-carboxylic acid,
7-[D(—)-α-(4-ethyl-2,3-dioxo-1-piperazinocarbonylamino)phenylacetamido]-3-[5-(1,3,4-thiadiazolyl)-thiomethyl]-Δ³-cephem-4-carboxylic acid,
7-[D(—)-α-(4-methyl-2,3-dioxo-1-piperazinocarbonylamino)phenylacetamido]-3-[2-(1-methyl-1,3,4-triazolyl)-thiomethyl]-Δ³-cephem-4-carboxylic acid,
7-[D(—)-α-(4-ethyl-2,3-dioxo-1-piperazinocarbonylamino)phenylacetamido]-3-[2-(1-methyl- 1,3,4-triazolyl)-thiomethyl]-Δ³-cephem-4-carboxylic acid, 7-[D(—)-α-(4-phenyl-2,3-dioxo-1-piperazinocarbonylamino)phenylacetamido]-3-[2-(1-methyl-1,3,4-triazolyl)-thiomethyl]-Δ³-cephem-4-carboxylic acid, 7-[D(—)-α-(4-methyl-2,3-dioxo-1-piperazinocarbonylamino)propionamido]-3-acetoxymethyl-Δ³-cephem-4-carboxylic acid, 7-[D(—)-α-(4-methyl-2,3-dioxo-1-piperazinocarbonylamino)-p-hydroxyphenylacetamido]-3-[5-(1-methyl-1,2,3,4-tetrazolyl)-thiomethyl]-Δ³-cephem-4-carboxylic acid, 7-[D(—)-α-(4-methyl-2,3-dioxo-1-piperazinocarbonylamino)phenylacetamido]-3-azidomethyl-Δ³-cephem-4-carboxylic acid, 7-[D(—)-α-(4-ethyl-2,3-dioxo-1-piperazinocarbonylamino)phenylacetamido]-3-[5-(1-methyl-1,2,3,4-tetrazolyl)-thiomethyl]-Δ³-cephem-4-carboxylic acid, 7-[D(—)-α-(4-methyl-2,3-dioxo-1-piperazinocarbonylamino)phenylacetamido]-3-[5-(1-methyl-1,2,3,4-tetrazolyl)-thiomethyl]-Δ³-cephem-4-carboxylic acid, 7-[D(—)-α-(4-methyl-2,3-dioxo-1-piperazinocarbonylamino)phenylacetamido]-3-[2-(1,3,4-triazolyl)-thiomethyl]-Δ³-cephem-4-carboxylic acid, 7-[D(—)-α-(4-methyl-2,3-dioxo-1-piperazinocarbonylamino)phenylacetamido]-3-[5-(1,2,3,4-tetrazolyl)-thiomethyl]-Δ³-cephem-4-carboxylic acid, 7-[D(—)-α-(4-ethyl-2,3-dioxo-1-piperazinocarbonylamino)phenylacetamido]-3-[5-(1,2,3,4-tetrazolyl)-thiomethyl]-Δ³-cephem-4-carboxylic acid, 7-[D(—)-α-(4-methyl-2,3-dioxo-1-piperazinocarbonylamino)phenylacetamido]-3-[2-(5-methyl-1,3,4-oxadiazolyl)-thiomethyl]-Δ³-cephem-4-carboxylic acid, 7-[D(—)-α-(4-methyl-2,3-dioxo-1-piperazinocarbonylamino)phenylacetamido]-3-[3-(2,6-dimethyl-5-oxo-2,5-dihydro-1,2,4-triazinyl)-thiomethyl]-Δ³-cephem-4-carboxylic acid, 7-[D(—)-α-(4-ethyl-2,3-dioxo-1-piperazinocarbonylamino)phenylacetamido]-3-[2-(4-methyloxazolyl)-thiomethyl]-Δ³-cephem-4-carboxylic acid, 7-[D(—)-α-(4-methyl-2,3-dioxo-1-piperazinocarbonylamino)phenylacetamido]-3-[2-(4-methylthiazolyl)-thiomethyl]-Δ³-cephem-4-carboxylic acid, 7-[D(—)-α-(4-ethyl-2,3-dioxo-1-piperazinocarbonylamino)phenylacetamido]-3-[2-(pyridyl-1-oxide)-thiomethyl]-Δ³-cephem-4-carboxylic acid, 7-[D(—)-α-(4-methyl-2,3-dioxo-1-piperazinocarbonylamino)phenylacetamido]-3-(2-thiazolinylthiomethyl)-Δ³-cephem-4-carboxylic acid, 7-[D(—)-α-(4-methyl-2,3-dioxo-1-piperazinocarbonylamino)phenylacetamido]-3-[2-(1-methylimidazolyl)-thiomethyl]-Δ³-cephem-(4-carboxylic acid, 7-[D(—)-α-(4-methyl-2,3-dioxo-1-piperazinocarbonylamino)phenylacetamido]-3-(2-pyrimidinylthiomethyl)-Δ³-cephem-4-carboxylic acid, 7-[D(—)-α-(4-ethyl-2,3-dioxo-1-piperazinocarbonylamino)phenylacetamido]-3-[3-(6-methylpyridazinyl)thiomethyl]-Δ³-cephem-4-carboxylic acid, 7-[D(—)-α-(4-methyl-2,3-dioxo-1-piperazinocarbonylamino)phenylacetamido]-3-[1-(4-methylpiperazino)thiocarbonylthiomethyl]-Δ³-cephem-4-carboxylic acid, 7-[D(—)-α-(4-methyl-2,3-dioxo-1-piperazinocarbonylamino)phenylacetamido]-3-[5-(3-methylisoxazolyl)carbonylthiomethyl]-Δ³-cephem-4-carboxylic acid, 7-[D(—)-α-(4-methyl-2,3-dioxo-1-piperazinocarbonylamino)phenylacetamido]-3-ethoxythiocarbonylthiomethyl-Δ³-cephem-4-carboxylic acid, 7-[D(—)-α-(4-ethoxycarbonyl-2-oxo-1-piperazinocarbonylamino)phenylacetamido]-3-methyl-Δ³-cephem-4-carboxylic acid, 7-[D(—)-α-(4-n-hexyl-3-oxo-1-piperazinocarbonylamino)phenylacetamido]-3-methyl-Δ³-cephem-4-carboxylic acid, 7-[D(—)-α-(4-acetyl-2-oxo-1-piperazinocarbonylamino)phenylacetamido]-3-[2-(5-methyl-1,3,4-thiadiazolyl)-thiomethyl]-Δ³-cephem-4-carboxylic acid, 7-[D(—)-α-(4-methanesulfonyl-2-oxo-1-piperazinocarbonylamino)phenylacetamido]-3-[2-(5-methyl-1,3,4-thiadiazolyl)-thiomethyl]-Δ³-cephem-4-carboxylic acid, 7-[D(—)-α-(4-methyl-2-oxo-1-piperazinocarbonylamino)phenylacetamido]-3-[2-(5-methyl-1,3,4-thiadiazolyl)-thiomethyl]-Δ³-cephem-4-carboxylic acid, 7-[D(—)-α-(4-ethyl-2-oxo-1-piperazinocarbonylamino)phenylacetamido]-3-[2-(5-methyl-1,3,4-thiadiazolyl)-thiomethyl]-Δ³-cephem-4-carboxylic acid, 7-[D(—)-α-(4-acetylaminocarbonyl-2-oxo-1-piperazinocarbonylamino)phenylacetamido]-3-[2-(5-methyl-1,3,4-thiadiazolyl)-thiomethyl]-Δ³-cephem-4-carboxylic acid, 7-[D(—)-α-(4-methyl-3-oxo-1-piperazinocarbonylamino)phenylacetamido]-3-[2-(5-methyl-1,3,4-thiadiazolyl)-thiomethyl]-Δ³-cephem-4-carboxylic acid, 7-[D(—)-α-(4-ethyl-3-oxo-1-piperazinocarbonylamino)phenylacetamido]-3-[2-(5-methyl-1,3,4-thiadiazolyl)-thiomethyl]-Δ³-cephem-4-carboxylic acid, 7-[D(—)-α-(3,5-dioxo-1-piperazinocarbonylamino)phenylacetamido]-3-[2-(5-methyl-1,3,4-thiadiazolyl)-thiomethyl]-Δ³-cephem-4-carboxylic acid, 7-[D(—)-α-(4-acetyl-2,5-dioxo-1-piperazinocarbonylamino)phenylacetamido]-3-[2-(5-methyl-1,3,4-thiadiazolyl)-thiomethyl]-Δ³-cephem-4-carboxylic acid, 7-[D(—)-α-(4-acetyl-2-oxo-1-piperazinocarbonylamino)phenylacetamido]-3-[5-(1-methyl-1,2,3,4-tetrazolyl)-thiomethyl]-Δ³-cephem-4-carboxylic acid, 7-[D(—)-α-(4-methanesulfonyl-2-oxo-1-piperazinocarbonylamino)phenylacetamido]-3-[5-(1-methyl-1,2,3,4-tetrazolyl)-thiomethyl]-Δ³-cephem-4-carboxylic acid, 7-[D(—)-α-(4-methyl-2-oxo-1-piperazinocarbonylamino)phenylacetamido]-3-[5-(1-methyl-1,2,3,4-tetrazolyl)-thiomethyl]-Δ³-cephem-4-carboxylic acid, 7-[D(—)-α-(4-ethyl-2-oxo-1-piperazinocarbonylamino)phenylacetamido]-3-[5-(1-methyl-1,2,3,4-tetrazolyl)-thiomethyl]-Δ³-cephem-4-carboxylic acid, 7-[D(−)-α-(4-acetylaminocarbonyl-2-oxo-1-piperazinocarbonylamino)phenylacetamido]-3-[5-(1-methyl-1,2,3,4-tetrazolyl)-thiomethyl]-Δ³-cephem-4-carboxylic acid, 7-[D(−)-α-(4-methyl-3-oxo-1-piperazinocarbonylamino)phenylacetamido]-3-[5-(1-methyl-1,2,3,4-tetrazolyl)-thiomethyl]-Δ³-cephem-4-carboxylic acid, 7-[D(−)-α-(4-ethyl-3-oxo-1-piperazinocarbonylamino)phenylacetamido]-3-[5-(1-methyl-1,2,3,4-tetrazolyl)-thiomethyl]-Δ³-cephem-4-carboxylic acid, 7-[D(−)-α-(3,5-dioxo-1-piperazinocarbonylamino)phenylacetamido]-3-[5-(1-methyl-1,2,3,4-tetrazolyl)-thiomethyl]-Δ³-cephem-4-carboxylic acid, 7-[D(−)-α-(4-acetyl-2,5-dioxo-1-piperazinocarbonylamino)phenylacetamido]-3-[5-(1-methyl-1,2,3,4-tetrazolyl)-thiomethyl]-Δ³-cephem-4-carboxylic acid, methoxymethyl 7-[D(−)-α-(4-methyl-2,3-dioxo-1-piperazinocarbonylamino)phenylacetamido]-3-methyl-Δ³-cephem-4-carboxylate, etc.

The antibacterial effectiveness tests of typical compounds among the compounds of the present invention are shown below.

(1) The minimum inhibitory concentrations (MIC) of the compounds against different standard strains are shown in Tables 3 and 4.

The minimum inhibitory concentration (MIC) was determined by the plate method disclosed in "Chemotherapy" (Japan), Vol. 16, (1968), pages 98–99. The culture medium used was a Heart infusion agar (pH 7.4). The number of the cells per plate used in the inoculum was $10^4$ ($10^6$ cells/ml).

Table 3

| Compound No. | Compound | Staphylococcus aureus 209p | Escherichia coli NIHJ | Pseudomonas aeruginosa I.F.O | Klebsiella pneumoniae | Proteus vulgaris 3027 |
|---|---|---|---|---|---|---|
| (Control) | Sodium Ampicillin | <1.57 | <1.57 | >200 | 50 | >200 |
| (Control) | Sodium Carbenicillin | <1.57 | <1.57 | 50 | >200 | <1.57 |
| (Control) | Sodium Sulbenicillin | 3.13 | 1.57 | 50 | >200 | 0.79 |
| 1 | (structure) | <1.57 | <1.57 | 25 | 12.5 | 3.13 |
| 2 | (structure) | <1.57 | <1.57 | 50 | 12.5 | 6.25 |
| 3 | (structure) | <1.57 | <1.57 | 100 | 3.13 | 3.13 |

Table 3-continued

| Compound No. | Compound | Staphylococcus aureus 209p | Escherichia coli NIHJ | Pseudomonas aeruginosa I.F.O | Klebsiella pneumoniae | Proteus vulgaris 3027 |
|---|---|---|---|---|---|---|
| 4 | (structure) | <1.57 | <1.57 | 25 | 12.5 | 3.13 |
| 5 | (structure) | <1.57 | <1.57 | 25 | 12.5 | <1.57 |
| 6 | (structure) | 3.13 | 3.13 | 50 | 6.25 | 6.25 |
| 7 | (structure) | <1.57 | <1.57 | 200 | 12.5 | 6.25 |
| 8 | (structure) | <1.57 | <1.57 | 100 | 6.25 | 3.13 |

Table 3-continued

| Compound No. | Compound | Staphylo- coccus aureus 209p | Escherichia coli NIHJ | Pseudomonas aeruginosa I.F.O | Klebsiella pneumoniae | Proteus vulgaris 3027 |
|---|---|---|---|---|---|---|
| 9 | (structure with CH₃-C₆H₄-CON-piperazinone-CONHCH(C₆H₅)CONH-penicillin COONa) | <1.57 | 3.13 | 100 | 3.13 | 3.13 |
| 10 | (structure with 2,4-Cl₂-C₆H₃-CON-piperazinone-CONHCH(C₆H₅)CONH-penicillin COONa) | <1.57 | <1.57 | 100 | 6.25 | 3.13 |
| 11 | (structure with CH₃CONH-CH₂-OCON-piperazinone-CONHCH(C₆H₅)CONH-penicillin COONa) | <1.57 | <1.57 | 50 | 50 | 6.25 |
| 12 | (structure with CH₃CH₂OCON-piperazinone-CONHCH(C₆H₅)CONH-penicillin COONa) | <1.57 | 3.13 | 50 | 6.25 | 12.5 |
| 13 | (structure with CH₃(CH₂)₄CH₂N-piperazinone-CONHCH(C₆H₅)CONH-penicillin COONa) | <1.57 | <1.57 | 25 | <1.57 | <1.57 |

Table 3-continued

| Compound No. | Compound | Staphylo-coccus aureus 209p | Escherichia coli NIHJ | Pseudomonas aeruginosa I.F.O | Klebsiella pneumoniae | Proteus vulgaris 3027 |
|---|---|---|---|---|---|---|
| 14 | (structure) | <1.57 | <1.57 | 25 | 3.13 | <1.57 |
| 15 | (structure) | <1.57 | 3.13 | 50 | 6.25 | 6.25 |
| 16 | (structure) | <1.57 | <1.57 | 12.5 | 1.57 | <1.57 |
| 17 | (structure) | <1.57 | <1.57 | 12.5 | 50 | 6.25 |
| 18 | (structure) | <1.57 | <1.57 | 12.5 | 25 | 3.13 |

Table 3-continued

| Compound No. | Compound | Staphylo- coccus aureus 209p | Escherichia coil NIHJ | Pseudomonas aeruginosa I.F.O | Klebsiella pneumoniae | Proteus vulgaris 3027 |
|---|---|---|---|---|---|---|
| 19 | (structure with CH₃CH₂N-piperidinone-NCONHCHCONH-penicillin, phenyl) | <1.57 | <1.57 | 12.5 | 50 | 3.13 |
| 20 | (structure with (CH₃)₂CHN-piperidinone-NCONHCHCONH-penicillin, phenyl) | 3.13 | <1.57 | 12.5 | 25 | 3.13 |
| 21 | (structure with (CH₃)₂CHCH₂CH₂N-piperidinone-NCONHCHCONH-penicillin, phenyl) | <0.79 | 1.57 | 25 | 25 | 3.13 |
| 22 | (structure with CH₃(CH₂)₂CH₂N-methylpiperidinone-NCONHCHCONH-penicillin, phenyl) | <1.57 | <1.57 | 50 | 12.5 | 6.25 |
| 23 | (structure with phenyl-N-piperidinone-NCONHCHCONH-penicillin, phenyl) | <1.57 | <1.57 | 25 | 6.25 | 3.13 |

Table 3-continued

| Compound No. | Compound | Staphylo- coccus aureus 209p | Escherichia coli NIHJ | Pseudomonas aeruginosa I.F.O | Klebsiella pneumoniae | Proteus vulgaris 3027 |
|---|---|---|---|---|---|---|
| 24 | HOCH$_2$CH$_2$N-[piperidone-NCONHCHCONH-phenyl-β-lactam-S-C(CH$_3$)$_2$-CHCOONa] | 3.13 | <1.57 | 50 | 50 | 25 |
| 25 | CH$_2$=CHCH$_2$N(CH$_3$)-[piperidone-NCONHCHCONH-phenyl-β-lactam-S-C(CH$_3$)$_2$-CHCOONa] | <1.57 | <1.57 | 25 | 50 | 3.13 |
| 26 | CH$_2$=CHCH$_2$N(CH$_3$)-[piperidone-NCONHCHCONH-phenyl-β-lactam-S-C(CH$_3$)$_2$-CHCOONa] | <1.57 | <1.57 | 25 | 25 | 12.5 |
| 27 | CH$_2$=CHCH$_2$N(CH$_3$)-[piperidone-NCONHCHCONH-phenyl-β-lactam-S-C(CH$_3$)$_2$-CHCOONa] | <1.57 | <1.57 | 25 | 25 | 3.13 |
| 28 | CH$_3$CH$_2$CH(CH$_3$)N-CH$_2$-[piperidone-NCONHCHCONH-phenyl-β-lactam-S-C(CH$_3$)$_2$-CHCOONa] (trans-) | <1.57 | <1.57 | 25 | 25 | 3.13 |

Table 3-continued

| Compound No. | Compound | Staphylococcus aureus 209p | Escherichia coli NIHJ | Pseudomonas aeruginosa I.F.O | Klebsiella pneumoniae | Proteus vulgaris 3027 |
|---|---|---|---|---|---|---|
| 29 | [CH₃(CH₂)₄CH₂N-piperidone-NCONHCHCONH-phenyl-penicillin-COONa] | 3.13 | <1.57 | 12.5 | 3.13 | 3.13 |
| 30 | [CH₃(CH₂)₆CH₂N-piperidone-NCONHCHCONH-phenyl-penicillin-COONa] | <1.57 | <1.57 | 25 | 6.25 | 3.13 |
| 31 | [CH₃(CH₂)₁₀CH₂N-piperidone-NCONHCHCONH-phenyl-penicillin-COONa] | <1.57 | <1.57 | 12.5 | 6.25 | <1.57 |
| 32 | [cyclopentyl-N-piperidone-NCONHCHCONH-phenyl-penicillin-COONa] | <1.57 | <1.57 | 12.5 | 12.5 | 6.25 |
| 33 | [phenyl-NHCON-piperidone-NCONHCHCONH-phenyl-penicillin-COONa] | <1.57 | <1.57 | 50 | 6.25 | 3.13 |

Table 3-continued
| Compound No. | Compound | Staphylo- coccus aureus 209p | Escherichia coli NIHJ | Pseudomonas aeruginosa I.F.O | Klebsiella pneumoniae | Proteus vulgaris 3027 |
|---|---|---|---|---|---|---|
| 34 | 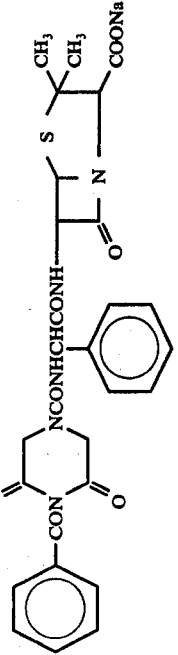 | 1.57 | 3.13 | 100 | 50 | 50 |
| 35 | 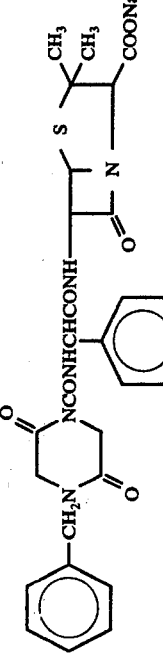 | 1.57 | 6.25 | 100 | 25 | 25 |
| 36 | 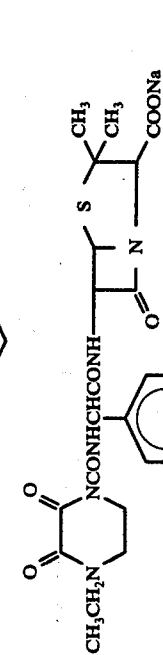 | <1.57 | <1.57 | 6.25 | <1.57 | <1.57 |
| 37 | 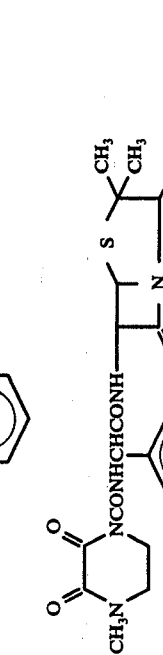 | <1.57 | <1.57 | 6.25 | 6.25 | <1.57 |
| 38 | 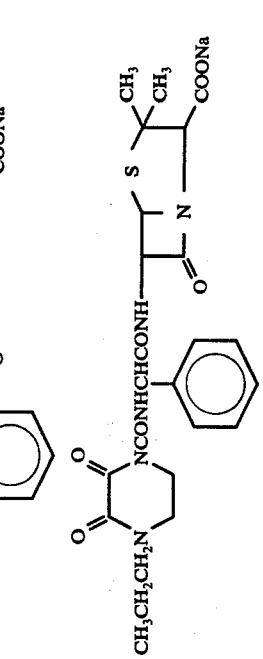 | 0.4 | <0.1 | 6.25 | 3.13 | 0.4 |

Table 3-continued

| Compound No. | Compound | Staphylococcus aureus 209p | Escherichia coli NIHJ | Pseudomonas aeruginosa I.F.O | Klebsiella pneumoniae | Proteus vulgaris 3027 |
|---|---|---|---|---|---|---|
| 39 | CH$_3$(CH$_2$)$_2$CH$_2$N–[dioxopiperazine]–CONHCHCONH–[penicillin, COONa]–C$_6$H$_5$ | 0.4 | <0.1 | 6.25 | 1.57 | 0.4 |
| 40 | (CH$_3$)$_2$CHN–[dioxopiperazine]–CONHCHCONH–[penicillin, COONa]–C$_6$H$_5$ | 0.4 | <0.1 | 6.25 | 3.13 | 0.4 |
| 41 | CH$_3$COOCH$_2$CH$_2$N–[dioxopiperazine]–CONHCHCONH–[penicillin, COONa]–C$_6$H$_5$ | <1.57 | <1.57 | 25 | 6.25 | <1.57 |
| 42 | CH$_2$=CHCH$_2$N–[dioxopiperazine]–CONHCHCONH–[penicillin, COONa]–C$_6$H$_5$ | 1.57 | <1.57 | 12.5 | 6.25 | <1.57 |
| 43 | C$_6$H$_5$–N–[dioxopiperazine]–CONHCHCONH–[penicillin, COONa]–C$_6$H$_5$ | <1.57 | <1.57 | 6.25 | 1.57 | <1.57 |

Table 3-continued

| Compound No. | Compound | Staphylo-coccus aureus 209p | Escherichia coli NIHJ | Pseudomonas aeruginosa I.F.O | Klebsiella pneumoniae | Proteus vulgaris 3027 |
|---|---|---|---|---|---|---|
| 44 | ClCH₂CH₂N-[2,3-dioxopiperazine]-CONHCHCONH-[penicillin core]-C₆H₅ | <1.57 | <1.57 | 6.25 | <1.57 | <1.57 |
| 45 | CH₃(CH₂)₃CH₂N-[2,3-dioxopiperazine]-CONHCHCONH-[penicillin core]-C₆H₅ | 0.79 | <0.1 | 12.5 | 0.79 | 0.4 |
| 46 | CH₃(CH₂)₄CH₂N-[2,3-dioxopiperazine]-CONHCHCONH-[penicillin core]-C₆H₅ | 0.2 | <0.1 | 6.25 | 0.4 | 0.4 |
| 47 | CH₃(CH₂)₆CH₂N-[2,3-dioxopiperazine]-CONHCHCONH-[penicillin core]-C₆H₅ | <1.57 | <1.57 | 6.25 | <1.57 | <1.57 |
| 48 | CH₃N-[2,3-dioxopiperazine]-CONHCHCONH-[penicillin core]-C₆H₄OH | <0.4 | <0.4 | 6.25 | 25 | <0.4 |

Table 3-continued

| Compound No. | Compound | Staphylococcus aureus 209p | Escherichia coli NIHJ | Pseudomonas aeruginosa I.F.O | Klebsiella pneumoniae | Proteus vulgaris 3027 |
|---|---|---|---|---|---|---|
| 49 | | <0.4 | 0.79 | 12.5 | 12.5 | 1.57 |
| 50 | | <0.79 | <0.79 | 6.25 | 6.25 | <0.79 |
| 51 | | <0.4 | <0.4 | 12.5 | <0.4 | <0.4 |
| 52 | | 0.79 | 0.79 | 25 | 25 | 1.57 |
| 53 | | 0.79 | <0.4 | 6.25 | 25 | 0.79 |

Table 3-continued

| Compound No. | Compound | Staphylo-coccus aureus 209p | Escherichia coli NIHJ | Pseudomonas aeruginosa I.F.O | Klebsiella pneumoniae | Proteus vulgaris 3027 |
|---|---|---|---|---|---|---|
| 54 | | 0.79 | 0.4 | 12.5 | 0.79 | 0.79 |
| 55 | | 0.79 | 0.4 | 6.25 | 25 | 0.79 |
| 56 | | <0.4 | <0.4 | 12.5 | 1.57 | 0.79 |
| 57 | | <0.79 | <0.79 | 12.5 | 12.5 | 3.13 |
| 58 | | <1.57 | <1.57 | 12.5 | 25 | 3.13 |

Table 3-continued
| Compound No. | Compound | Staphylo-coccus aureus 209p | Escherichia coil NIHJ | Pseudomonas aeruginosa I.F.O | Klebsiella pneumoniae | Proteus vulgaris 3027 |
|---|---|---|---|---|---|---|
| 59 | 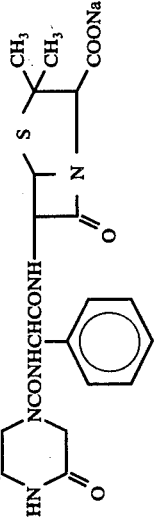 | <1.57 | <1/57 | 25 | 200 | 3.13 |
(Note)
Sodium Carbenicillin and Sodium Sulbenicillin are regarded as preferable drugs at the level of skill of this technical field, and hence are described for reference.

Table 4

| Compound No. | Compound | Staphylococcus aureus 209p | Escherichia coli NIHJ | Pseudomonas aeruginosa I.F.O. | Klebsiella pneumoniae | Proteus vulgaris 3027 |
|---|---|---|---|---|---|---|
| (Control) | (Sodium Cephaloglycin) | < 1.57 | < 1.57 | > 200 | < 1.57 | 100 |
| | (Sodium Cephalothin) | < 1.57 | < 1.57 | > 200 | < 1.57 | 100 |
| | (Sodium Cephazolin) | < 1.57 | < 1.57 | > 200 | 1.57 | 200 |
| | (Cephaloridine) | < 1.57 | > 3.13 | 200 | 3.13 | 200 |
| 60 | | 0.79 | < 0.1 | 25 | 3.13 | 3.13 |
| 61 | | < 0.79 | < 0.79 | 25 | 3.13 | 3.13 |
| 62 | | 0.79 | < 0.1 | 50 | 1.57 | 3.13 |
| 63 | | < 0.79 | < 0.79 | 25 | < 0.79 | 1.57 |

Table 4-continued

| Compound No. | Compound | Staphylococcus aureus 209p | Escherichia coli NIHJ | Pseudomonas aeruginosa I.F.O. | Klebsiella pneumoniae | Proteus vulgaris 3027 |
|---|---|---|---|---|---|---|
| 64 | (structure) | 0.79 | <0.1 | 25 | 1.57 | 3.13 |
| 65 | (structure) | 3.13 | 0.79 | 25 | 3.13 | 3.13 |
| 66 | (structure) | <0.79 | <0.79 | 25 | 0.79 | <1.57 |
| 67 | (structure) | 6.25 | <0.79 | 100 | 3.13 | 12.5 |
| 68 | (structure) | 1.57 | <0.79 | 12.5 | <0.79 | 1.57 |
| 69 | (structure) | <0.79 | <0.79 | 12.5 | <0.4 | <0.79 |
| 70 | (structure) | <0.79 | 1.57 | 100 | 1.56 | <0.79 |
| 71 | (structure) | <0.79 | <0.79 | 50 | 1.56 | <0.79 |

Table 4-continued

| Compound No. | Compound | Staphylococcus aureus 209p | Escherichia coli NIHJ | Pseudomonas aeruginosa I.F.O. | Klebsiella pneumoniae | Proteus vulgaris 3027 |
|---|---|---|---|---|---|---|
| 72 | | < 1.57 | < 0.1 | 6.25 | < 0.1 | 0.4 |
| 73 | | 1.57 | < 0.1 | 25 | 0.2 | 1.57 |
| 74 | | 1.57 | 0.2 | 12.5 | 0.79 | 1.57 |
| 75 | | 1.57 | < 0.4 | 50 | 1.57 | 12.5 |
| 76 | | 1.57 | < 0.4 | 50 | 0.79 | 3.13 |
| 77 | | 1.57 | < 0.1 | 25 | 0.4 | 1.57 |
| 78 | | 3.13 | < 0.1 | 12.5 | 0.2 | 0.79 |

Table 4-continued

| Compound No. | Compound | Staphylococcus aureus 209p | Escherichia coli NIHJ | Pseudomonas aeruginosa I.F.O. | Klebsiella pneumoniae | Proteus vulgaris 3027 |
|---|---|---|---|---|---|---|
| 79 | CH₃CH₂N-piperazinedione-NCONHCHCONH-[4-OH-phenyl]-cephem-CH₂S-thiadiazole, COONa | 1.57 | <0.1 | 3.13 | 0.79 | 3.13 |
| 80 | CH₃CH₂N-piperazinedione-NCONHCHCONH-[phenyl]-cephem-CH₂OCH₃, COONa | 0.79 | <0.1 | 50 | 3.13 | 6.25 |
| 81 | CH₃CH₂N-piperazinedione-NCONHCHCONH-[4-OH-phenyl]-cephem-CH₂OCOCH₃, COONa | <1.57 | <1.57 | 12.5 | <1.57 | <1.57 |
| 82 | HOCH₂CH₂N-piperazinedione-NCONHCHCONH-[phenyl]-cephem-CH₂S-tetrazole-CH₃, COONa | 1.57 | <0.1 | 25 | 0.79 | 0.79 |
| 83 | HOCH₂CH₂N-piperazinedione-NCONHCHCONH-[4-OH-phenyl]-cephem-CH₂S-tetrazole-CH₃, COONa | 1.57 | <1.57 | 25 | <1.57 | <1.57 |
| 84 | CH₃CH₂N-piperazinedione-NCONHCHCONH-[4-OH-phenyl]-cephem-CH₂OCONH₂, COONa | <1.57 | <1.57 | 25 | <1.57 | <1.57 |

(Note) Sodium Cephalothin, Sodium Cephazolin and Cephaloridine are regarded as preferable drugs at the level of skill of this technical field, and hence are set forth for reference.

(2) The minimum inhibitory concentrations (MIC) of the compounds against clinical isolates of bacteria are shown in Tables 5 and 6.

MIC was determined in the same manner as in the preceding paragraph (1).

Table 5-1

| | | Staphylococcus aureus | | | | | | | | | |
|---|---|---|---|---|---|---|---|---|---|---|---|
| Compound | | MS 8619 | MS 8588 | MS 8713 | MS 8596 | MS 8684 | F-1 | F-2 | F-3 | F-4 | F-5 |
| Control | Sodium Ampicillin | <0.4 | 6.25 | 3.13 | 1.56 | 1.56 | 12.5 | 0.79 | | 12.5 | 50 |
| | Sodium Carbenicillin | 0.79 | 6.25 | 6.25 | 6.25 | 6.25 | 6.25 | 3.13 | 3.13 | 12.5 | >200 |

Table 5-1-continued

| Compound | | Staphylococcus aureus | | | | | | | | | |
|---|---|---|---|---|---|---|---|---|---|---|---|
| | | MS 8619 | MS 8588 | MS 8713 | MS 8596 | MS 8684 | F-1 | F-2 | F-3 | F-4 | F-5 |
| Sodium Sulbenicillin | | 3.13 | 3.13 | 3.13 | 3.13 | 3.13 | 6.25 | 3.13 | 6.25 | 6.25 | >200 |
| Compound No. | 1 | 1.57 | 6.25 | 3.13 | 3.13 | 3.13 | 12.5 | 3.13 | | 6.25 | >200 |
| " | 13 | 0.79 | 3.13 | 3.13 | 3.13 | 3.13 | 12.5 | 1.57 | | 6.25 | 200 |
| " | 14 | 0.79 | 3.13 | 3.13 | 3.13 | 3.13 | 12.5 | 1.57 | | 6.25 | 200 |
| " | 16 | <0.4 | 3.13 | 3.13 | 3.13 | 3.13 | 6.25 | 0.79 | | 6.25 | 100 |
| " | 30 | <0.4 | 1.57 | 1.57 | 1.57 | 1.57 | 3.13 | 0.79 | 0.79 | 3.13 | 100 |
| " | 36 | 0.79 | 3.13 | 6.25 | 3.13 | 3.13 | 12.5 | 3.13 | 1.57 | 6.25 | >200 |
| " | 37 | 0.79 | 3.13 | 12.5 | 3.13 | 3.13 | 12.5 | 1.57 | 3.13 | 6.25 | >200 |
| " | 38 | 0.79 | 3.13 | 6.25 | 3.13 | 3.13 | 6.25 | 1.57 | 0.79 | 6.25 | >200 |
| " | 39 | 0.79 | 1.57 | 3.13 | 1.57 | 3.13 | 6.25 | 1.57 | 1.57 | 6.25 | >200 |
| " | 40 | 0.79 | 3.13 | 12.5 | 3.13 | 3.13 | 6.25 | 3.13 | 0.79 | 6.25 | >200 |
| " | 45 | 0.79 | 3.13 | 6.25 | 3.13 | 3.13 | 6.25 | 1.57 | 1.57 | 6.25 | >200 |
| " | 46 | <0.4 | 1.57 | 6.25 | 3.13 | 1.57 | 6.25 | 1.57 | 0.79 | 6.25 | >200 |
| " | 47 | <0.4 | 3.13 | 6.25 | 3.13 | 3.13 | 6.25 | 1.57 | 1.57 | 12.5 | >200 |

Table 5-2

| Compound | | Escherichia coli | | | | | | | | |
|---|---|---|---|---|---|---|---|---|---|---|
| | | GN 3481 | GN 3435 | GN 3452 | GN 3465 | GN 3611 | K-1 | K-2 | K-3 | K-4 |
| Control | Sodium Ampicillin | 6.25 | 3.13 | 6.25 | | >200 | 6.25 | 6.25 | >200 | 12.5 |
| | Sodium Carbenicillin | 6.25 | 6.25 | 12.5 | >200 | >200 | 6.25 | 6.25 | >200 | 12.5 |
| | Sodium Sulbenicillin | 12.5 | 6.25 | 12.5 | >200 | >200 | 6.25 | 12.5 | >200 | 6.25 |
| Compound No. | 1 | 12.5 | 6.25 | 12.5 | 200 | | 6.25 | 25 | >200 | 12.5 |
| " | 13 | 6.25 | 3.13 | 3.13 | 25 | | 3.13 | 6.25 | 100 | 6.25 |
| " | 14 | 6.25 | 6.25 | 6.25 | 50 | | 3.13 | 12.5 | 200 | 6.25 |
| " | 16 | 3.13 | 1.57 | 1.57 | 12.5 | | 1.57 | 3.13 | 50 | 3.13 |
| " | 30 | 25 | 12.5 | 25 | 50 | >200 | 12.5 | 25 | >200 | 12.5 |
| " | 36 | 3.13 | 1.57 | 3.13 | 100 | >200 | 3.13 | 3.13 | >200 | 1.57 |
| " | 37 | 6.25 | 3.13 | 12.5 | 200 | >200 | 12.5 | 6.25 | >200 | 3.13 |
| " | 38 | 3.13 | 0.79 | 3.13 | 50 | >200 | 3.13 | 3.13 | >200 | 0.79 |
| " | 39 | 1.57 | 0.79 | 0.79 | 25 | >200 | 1.57 | 1.57 | >200 | 0.79 |
| " | 40 | 1.57 | 0.79 | 1.57 | 50 | >200 | 1.57 | 3.13 | >200 | 0.79 |
| " | 45 | 1.57 | 0.79 | 1.57 | 25 | >200 | 0.79 | 1.57 | 200 | 0.79 |
| " | 46 | 3.13 | <0.4 | 0.79 | 6.25 | >200 | 0.79 | 0.79 | 50 | <0.4 |
| " | 47 | 1.57 | 0.79 | 1.57 | 6.25 | >200 | 1.57 | 1.57 | 100 | 0.79 |

Table 5-3

| Compound | | Pseudomonas aeruginosa | | | | | | | | | |
|---|---|---|---|---|---|---|---|---|---|---|---|
| | | GN 1035 | GN 376 | GN 82 | GN 221 | GN 1091 | GN 2565 | GN2987 | GN 163 | GN 244 | GN 383 |
| Control | Sodium Ampicillin | >200 | >200 | >200 | >200 | >200 | >200 | >200 | >200 | >200 | >200 |
| | Sodium Carbenicillin | >200 | 50 | 100 | 25 | 100 | 200 | 50 | 50 | 50 | 50 |
| | Sodium Sulbenicillin | 100 | 50 | 50 | 25 | 50 | 100 | 25 | 50 | 50 | 50 |
| Compound No. | 1 | 100 | 25 | 25 | 25 | 25 | 50 | 25 | 25 | 25 | 50 |
| " | 13 | 50 | 50 | 50 | 25 | 25 | 25 | 50 | 12.5 | 25 | 50 |
| " | 14 | 50 | 50 | 50 | 25 | 25 | 25 | 50 | 12.5 | 25 | 50 |
| " | 16 | 25 | 25 | 6.25 | 25 | 12.5 | 12.5 | 3.13 | 12.5 | 12.5 | 25 |
| " | 19 | 100 | 12.5 | 12.5 | 12.5 | 12.5 | 50 | 12.5 | 12.5 | 25 | 12.5 |
| " | 30 | 50 | 50 | 25 | 50 | 25 | 50 | 12.5 | 25 | 50 | 50 |
| " | 36 | 25 | 6.25 | 6.25 | 3.13 | 6.25 | 25 | 12.5 | 6.25 | 12.5 | 6.25 |
| " | 37 | 50 | 12.5 | 6.25 | 6.25 | 12.5 | 25 | 25 | 12.5 | 50 | 25 |
| " | 38 | 12.5 | 3.13 | 3.13 | 6.25 | 3.13 | 12.5 | 6.25 | 3.13 | 6.25 | 6.25 |
| " | 39 | 12.5 | 6.25 | 3.13 | 3.13 | 3.13 | 12.5 | 3.13 | 3.13 | 6.25 | 6.25 |
| " | 40 | 25 | 3.13 | 6.25 | 6.25 | 6.25 | 12.5 | 3.13 | 6.25 | 6.25 | 6.25 |
| " | 45 | 50 | 25 | 12.5 | 3.13 | 12.5 | 25 | 12.5 | 12.5 | 25 | 25 |
| " | 46 | 50 | 25 | 6.25 | 12.5 | 12.5 | 12.5 | 6.25 | 6.25 | 12.5 | 25 |
| " | 47 | 25 | 50 | 12.5 | 25 | 12.5 | 25 | 12.5 | 12.5 | 25 | 50 |

Table 5-4

| Compound | | Pseudomonas aeruginosa | | | | Klebsiella pneumoniae | | | |
|---|---|---|---|---|---|---|---|---|---|
| | | S-1 | S-2 | S-3 | S-4 | GN 4117 | GN 4081 | GN 3850 | GN 917 |
| Control | Sodium Ampicillin | >200 | >200 | >200 | >200 | >200 | >200 | 50 | 25 |
| | Sodium Carbenicillin | 200 | 200 | 200 | 200 | >200 | >200 | | >200 |
| | Sodium Sulbenicillin | 100 | 100 | 100 | 100 | >200 | >200 | >200 | >200 |
| Compound No. | 1 | 50 | 100 | 50 | 50 | 200 | >200 | 25 | 25 |
| " | 13 | 50 | 50 | 100 | 50 | 25 | 25 | 6.25 | 12.5 |
| " | 14 | 50 | 50 | 100 | 50 | 50 | 50 | 12.5 | 25 |
| " | 16 | 12.5 | 25 | 50 | 25 | 25 | 25 | 3.13 | 12.5 |
| " | 19 | 50 | 50 | 50 | 50 | >200 | >200 | 100 | 50 |
| " | 30 | 50 | 50 | 100 | 50 | 100 | 100 | 25 | 25 |
| " | 36 | 50 | 12.5 | 25 | 50 | 100 | 100 | 12.5 | 6.25 |
| " | 37 | 200 | 25 | 50 | 100 | 100 | 200 | 25 | 12.5 |
| " | 38 | 12.5 | 12.5 | 12.5 | 12.5 | 50 | 50 | 6.25 | 3.13 |

Table 5-4-continued

| Compound | | Pseudomonas aeruginosa | | | | Klebsiella pneumoniae | | | |
|---|---|---|---|---|---|---|---|---|---|
| | | S-1 | S-2 | S-3 | S-4 | GN 4117 | GN 4081 | GN 3850 | GN 917 |
| " | 39 | 12.5 | 12.5 | 25 | 12.5 | 25 | 25 | 3.13 | 1.57 |
| " | 40 | 12.5 | 25 | 25 | 12.5 | 50 | 100 | 12.5 | 6.25 |
| " | 45 | 25 | 25 | 50 | 25 | 25 | 25 | 3.13 | 1.57 |
| " | 46 | 50 | 50 | 50 | 50 | 12.5 | 12.5 | 1.57 | 0.79 |
| " | 47 | 50 | 50 | 50 | 50 | 12.5 | 12.5 | 3.13 | 1.57 |

Table 5-5

| Compound | | Shigella sonnei | | Shigella flexneri | | Salmonella typhi | | Salmonella typhi-murium | |
|---|---|---|---|---|---|---|---|---|---|
| | | JS 11755 | JS 11232 | JS 11215 | JS 11839 | SL 2169 | SL 819 | SL 2136 | SL 858 |
| Control | Sodium Ampicillin | 6.25 | >200 | | 1.57 | 0.78 | 1.56 | >200 | 3.13 |
| | Sodium Carbenicillin | 12.5 | >200 | >200 | 12.5 | 3.13 | 6.25 | >200 | 12.5 |
| | Sodium Sulbenicillin | >200 | >200 | >200 | 12.5 | 1.57 | 6.25 | >200 | 25 |
| | Compound No. 1 | 12.5 | >200 | 100 | 3.13 | 6.25 | 6.25 | >200 | 12.5 |
| " | 13 | 3.13 | 12.5 | 12.5 | 1.57 | 3.13 | 6.25 | 200 | 0.79 |
| " | 14 | 6.25 | 25 | 25 | 3.13 | 3.13 | 6.25 | 200 | 1.57 |
| " | 16 | 1.57 | 6.25 | 6.25 | 0.79 | 1.57 | 3.13 | 100 | 1.57 |
| " | 36 | 3.13 | 50 | 100 | 3.13 | 1.57 | 1.57 | >200 | 6.25 |
| " | 37 | 6.25 | 100 | >200 | 6.25 | 3.13 | 6.25 | >200 | 12.5 |
| " | 38 | 3.13 | 50 | 25 | 1.57 | 0.79 | 1.57 | 200 | 3.13 |
| " | 39 | 1.57 | 25 | 25 | 0.79 | 0.79 | 0.79 | 100 | 0.79 |
| " | 40 | 3.13 | 50 | 50 | 3.13 | 1.57 | 1.57 | >200 | 6.25 |
| " | 45 | 1.57 | 25 | 25 | 1.57 | 0.79 | 1.57 | 200 | 0.79 |
| " | 46 | 0.79 | 12.5 | 6.25 | 0.79 | 0.79 | 1.57 | 50 | <0.4 |
| " | 47 | 0.79 | 6.25 | 6.25 | 1.57 | 1.57 | 3.13 | 50 | <0.4 |

Table 5-6

| Compound | | Proteus | | | |
|---|---|---|---|---|---|
| | | mirabilis | morganii | vulgaris | rettgeri |
| Control | Sodium Ampicillin | <1.57 | <1.57 | <1.5 | 200 |
| | Sodium Carbenicillin | 0.8 | 0.4 | 0.8 | >200 |
| | Sodium Sulbenicillin | 0.79 | <0.4 | <0.4 | >200 |
| | Compound No. 16 | 1.56 | 1.56 | 0.8 | 6.25 |
| " | 30 | 3.13 | 3.13 | 3.13 | 12.5 |
| " | 36 | <0.4 | <0.4 | <0.4 | 12.5 |
| " | 37 | 0.79 | 0.79 | <0.4 | 25 |
| " | 38 | <0.4 | <0.4 | <0.4 | 12.5 |
| " | 39 | <0.4 | <0.4 | <0.4 | 6.25 |
| " | 40 | <0.4 | 0.79 | <0.4 | 6.25 |
| " | 45 | <0.4 | 0.79 | <0.4 | 6.25 |
| " | 46 | <0.4 | <0.4 | <0.4 | 3.13 |
| " | 47 | <0.4 | <0.4 | <0.4 | 0.79 |

Table 6-1

| Compound | | Staphylococcus aureus | | | | | | | | |
|---|---|---|---|---|---|---|---|---|---|---|
| | | MS 8619 | MS 8588 | MS 8713 | MS 8596 | MS 8684 | F-1 | F-2 | F-3 | F-4 | F-5 |
| Control | Sodium Cephaloglycin | 1.56 | 3.13 | 3.13 | 1.56 | 1.56 | 3.13 | 1.56 | 1.56 | 3.13 | 25 |
| | Sodium Cephalothin | <0.4 | <0.4 | <0.4 | <0.4 | <0.4 | <0.4 | <0.4 | <0.4 | <0.4 | 1.56 |
| | Sodium Cephazolin | <0.4 | <0.4 | <0.4 | <0.4 | <0.4 | 0.78 | <0.4 | <0.4 | <0.4 | 0.78 |
| | Cephalorizine | <0.4 | <0.4 | <0.4 | <0.4 | <0.4 | <0.4 | <0.4 | <0.4 | <0.4 | 0.78 |
| | Compound No. 60 | 0.78 | 1.56 | 0.78 | 0.78 | 1.56 | 3.13 | 0.78 | 1.56 | 1.56 | 50 |
| " | 61 | 1.56 | 1.56 | 1.56 | 1.56 | 1.56 | 3.13 | 1.56 | 1.56 | 3.13 | 50 |
| " | 62 | 0.78 | 1.56 | 1.56 | 0.78 | 1.56 | 3.13 | 0.78 | 1.56 | 1.56 | 12.5 |
| " | 63 | 0.78 | 1.56 | 1.56 | 1.56 | 1.56 | 3.13 | 0.78 | 1.56 | 1.56 | 12.5 |
| " | 68 | 0.78 | 1.56 | 3.13 | 1.56 | 1.56 | 1.56 | 1.56 | 0.78 | 6.25 | 0.78 |
| " | 69 | 0.78 | 1.56 | 1.56 | 1.56 | 1.56 | 3.13 | 1.56 | 0.78 | 3.13 | 0.78 |
| " | 72 | 1.56 | 1.56 | — | 3.13 | 1.56 | 1.56 | — | — | — | — |
| " | 73 | 1.56 | 1.56 | — | 3.13 | 1.56 | 1.56 | — | — | — | — |
| " | 74 | 0.78 | 0.78 | — | 0.78 | 0.78 | 0.78 | — | — | — | — |
| " | 77 | 1.56 | 1.56 | — | 1.56 | 1.56 | 1.56 | — | — | — | — |
| " | 78 | 1.56 | 3.13 | — | 3.13 | 1.56 | 3.13 | — | — | — | — |
| " | 79 | 1.56 | 3.13 | — | 3.13 | 1.56 | 1.56 | — | — | — | — |
| " | 82 | 1.56 | 3.13 | — | 3.13 | 1.56 | 3.13 | — | — | — | — |

Table 6-2

| Compound | | Escherichia coli | | | | | | | | |
|---|---|---|---|---|---|---|---|---|---|---|
| | | GN 3481 | GN 3435 | GN 3452 | GN 3465 | GN 3611 | K-1 | K-2 | K-3 | K-4 |
| Control | Sodium Cephaloglycin | 3.13 | 1.56 | 3.13 | 12.5 | 25 | 1.56 | 1.56 | 25 | 12.5 |
| | Sodium Cephalothin | 12.5 | 6.25 | 12.5 | 25 | 50 | 6.25 | 6.25 | 100 | 25 |
| | Sodium Cephazolin | 1.56 | 1.56 | 1.56 | 6.25 | 25 | 1.56 | 1.56 | >200 | 3.13 |
| | Cephalorizine | 3.13 | 3.13 | 3.13 | 50 | 100 | 3.13 | 3.13 | 200 | 6.25 |
| | Compound No. 60 | 6.25 | 6.25 | 12.5 | 100 | >200 | 6.25 | 12.5 | 200 | 25 |
| " | 61 | 3.13 | 3.13 | 6.25 | 50 | 200 | 3.13 | 6.25 | 100 | 6.25 |

Table 6-2-continued

| Compound | | Escherichia coli | | | | | | | | |
|---|---|---|---|---|---|---|---|---|---|---|
| | | GN 3481 | GN 3435 | GN 3452 | GN 3465 | GN 3611 | K-1 | K-2 | K-3 | K-4 |
| " | 62 | 6.25 | 6.25 | 6.25 | 25 | 200 | 6.25 | 12.5 | 200 | 12.5 |
| " | 63 | 3.13 | 3.13 | 12.5 | 25 | 100 | 3.13 | 6.25 | 50 | 6.25 |
| " | 72 | — | 0.1 | 0.2 | 1.56 | — | — | 0.39 | — | 0.39 |
| " | 73 | — | 0.78 | 0.78 | 1.56 | — | — | 1.56 | — | 0.78 |
| " | 74 | — | 0.78 | 1.56 | 1.56 | — | — | 3.13 | — | 1.56 |
| " | 77 | — | 1.56 | 1.56 | 6.25 | — | — | 3.13 | — | 1.56 |
| " | 78 | — | 0.39 | 0.39 | 1.56 | — | — | 0.78 | — | 0.39 |
| " | 79 | — | 0.39 | 0.39 | 3.13 | — | — | 1.56 | — | 0.78 |
| " | 82 | — | 1.56 | 1.56 | 6.25 | — | — | 6.25 | — | 1.56 |

Table 6-3

| Compound | | Pseudomonas aeruginosa | | | | | | | | | |
|---|---|---|---|---|---|---|---|---|---|---|---|
| | | GN 1035 | GN 376 | GN 82 | GN 221 | GN 1091 | GN 2565 | GN 2987 | GN 163 | GN 244 | GN 383 |
| Control | Sodium Cephaloglycin | >200 | >200 | >200 | >200 | >200 | >200 | >200 | >200 | >200 | >200 |
| | Sodium Cephalothin | >200 | >200 | >200 | >200 | >200 | >200 | >200 | >200 | >200 | >200 |
| | Sodium Cephazolin | >200 | >200 | >200 | >200 | >200 | >200 | >200 | >200 | >200 | >200 |
| | Cephalorizine | >200 | >200 | >200 | >200 | >200 | >200 | >200 | >200 | >200 | >200 |
| Compound No. | 60 | 200 | 50 | 50 | 12.5 | 50 | 100 | 50 | 50 | 50 | 50 |
| " | 61 | 100 | 12.5 | 25 | 6.25 | 25 | 50 | 25 | 25 | 25 | 12.5 |
| " | 62 | 200 | 100 | 100 | 50 | 100 | 100 | 50 | 50 | 100 | 100 |
| " | 63 | 100 | 50 | 50 | 25 | 50 | 50 | 25 | 25 | 50 | 25 |
| " | 68 | 50 | 12.5 | 6.25 | 3.13 | 12.5 | 50 | 12.5 | 12.5 | 25 | 12.5 |
| " | 69 | 50 | 12.5 | 12.5 | 6.25 | 12.5 | 50 | 12.5 | 12.5 | 25 | 25 |
| " | 72 | 25 | 6.25 | 6.25 | 6.25 | 6.25 | 25 | — | — | 12.5 | 12.5 |
| " | 73 | 50 | 12.5 | 12.5 | 12.5 | 12.5 | 25 | — | — | 12.5 | 12.5 |
| " | 74 | 25 | 50 | 25 | 50 | 25 | 50 | — | — | 25 | 50 |
| " | 77 | 50 | 25 | 25 | 12.5 | 25 | 50 | — | — | 25 | 25 |
| " | 78 | 25 | 12.5 | 12.5 | 6.25 | 25 | 12.5 | — | — | 12.5 | 25 |
| " | 79 | 25 | 6.25 | 12.5 | 6.25 | 12.5 | 25 | — | — | 12.5 | 12.5 |
| " | 82 | 50 | 25 | 50 | 25 | 50 | 50 | — | — | 50 | 50 |

Table 6-4

| Compound | | Pseudomonas aeruginosa | | | | Klebsiella pneumoniae | | |
|---|---|---|---|---|---|---|---|---|
| | | S-1 | S-2 | S-3 | S-4 | GN 4117 | GN 4081 | GN 917 |
| Control | Sodium Cephaloglycin | >200 | >200 | >200 | >200 | 3.13 | 3.13 | 1.56 |
| | Sodium Cephalothin | >200 | >200 | >200 | >200 | 6.25 | 12.5 | 3.13 |
| | Sodium Cephazolin | >200 | >200 | >200 | >200 | 3.13 | 3.13 | 1.56 |
| | Cephalorizine | >200 | >200 | >200 | >200 | 12.5 | 12.5 | 3.13 |
| Compound No. | 60 | 200 | 100 | 100 | 100 | 25 | 25 | 6.25 |
| " | 61 | 50 | 50 | 50 | 50 | 12.5 | 12.5 | 6.25 |
| " | 62 | 200 | 200 | 200 | 200 | 25 | 12.5 | 6.25 |
| " | 63 | 100 | 100 | 100 | 100 | 6.25 | 6.25 | 3.13 |
| " | 68 | 25 | 25 | 25 | 25 | — | — | 1.56 |
| " | 69 | 25 | 25 | 50 | 50 | — | — | 0.78 |
| " | 72 | 12.5 | — | — | — | — | 1.56 | 0.2 |
| " | 73 | 50 | — | — | — | — | 1.56 | 0.78 |
| " | 74 | 50 | — | — | — | — | 1.56 | 1.56 |
| " | 77 | 50 | — | — | — | — | 3.13 | 1.56 |
| " | 78 | 25 | — | — | — | — | 3.13 | 0.39 |
| " | 79 | 25 | — | — | — | — | 12.5 | 0.78 |
| " | 82 | 100 | — | — | — | — | 6.25 | 1.56 |

Table 6-5

| Compound | Proteus | | | |
|---|---|---|---|---|
| | mirabilis | morganii | vulgaris | rettgeri |
| Sodium Cephaloglycin | 3.13 | 1.56 | 50 | 50 |
| Compound No. 60 | 3.13 | 3.13 | 1.56 | 6.25 |
| " 61 | 1.56 | 1.56 | 0.8 | 3.13 |
| " 62 | 6.25 | 3.13 | 3.13 | 6.25 |
| " 63 | 3.13 | 3.13 | 1.56 | 3.13 |
| " 72 | 0.78 | 0.78 | 0.39 | 1.56 |
| " 73 | 0.39 | 0.78 | 0.78 | 3.13 |
| " 74 | 0.39 | 0.78 | 0.78 | 6.25 |
| " 77 | 1.56 | 1.56 | 0.78 | 1.56 |
| " 78 | 1.56 | 1.56 | 0.39 | 1.56 |
| " 79 | 1.56 | 1.56 | 0.39 | 3.13 |
| " 82 | 3.13 | 1.56 | 0.78 | 6.25 |

(3) Resistant activity against β-lactamase, Pseudomonas aerugionsa GN 238:

The resistant activity of each compound against β-lactamase was measured in the manner described below.

β-Lactamase was prepared from *Pseudomonas aeruginosa* GN 238. This microorganism was cultured in 100 ml of a medium containing 2 g of yeast extract, 10 g of polypeptone, 2 g of glucose, 7 g of disodium hydrogen phosphate, 2 g of potassium dihydrogen phosphate, 1.2 g of ammonium sulfate and 0.4 g of magnesium sulfate, per liter, in a 500-ml Erlenmeyer flask for 6 hrs. at 37° C. with shaking. The resulting cells were collected by centrifugation (5,000 r.p.m. × 10 min.), washed three times with 0.1 M phosphate buffer (pH 7.0). Subsequently, the cells were subjected to sonication (20 KH$_z$, 20 min.) and then centrifuged at 15,000 r.p.m. for 60 min. By using the supernatant of enzyme fluid, the resistance of each compound against β-lactamase was determined by the iodometric assay method. The results obtained were as set forth in Table 7. Each numeral shown in Table 7 is a relative activity value calculated by assuming as 100 the activity of the control Potassium Penicillin G.

Table 7-1

| Compound | | Comparison of resistant activity against β-lactamase Relative activity (%) |
|---|---|---|
| Con-trol | Potassium Penicillin G | 100 |
| | Sodium Ampicillin | 115 |
| | Sodium Carbenicillin | 116 |
| | Sodium Sulbenicillin | 50 |
| | Compound No. 30 | 3 |
| " | 36 | 14 |
| " | 37 | 15 |
| " | 38 | 15 |
| " | 39 | 15 |
| " | 40 | 15 |
| " | 45 | 16 |
| " | 46 | 12 |
| " | 47 | 1 |

(4) Resistant activity of each cephalosporin compound against β-lactamase, *Proteus vulgaris* GN 76 and *Escherichia freundii* GN 346:

The resistant activity of each cephalosporin compound against β-lactamase was measured in the manner described below.

β-lactamase was prepared from *Proteus vulgaris* GN 76 and *Esherichia freundii* GN 346. 10 ml of an overnight culture in Heart Infusion broth was diluted with 100 ml of a medium containing 2 g of yeast extract, 10 g of polypeptone, 2 g of glucose, 7 g of disodium hydrogen phosphate, 2 g of potassium dihydrogen phosphate, 1.2 g of ammonium sulfate and 0.4 g of magnesium sulfate, per liter, and incubated with shaking at 37° C. After incubation of 2 hrs, Penicillin G (50 μg/ml) was added as the inducer, and further incubated for 2 hrs. The resulting cells were collected by centrifugation (5,000 r.p.m. × 10 min.) and washed two times with 0.1 M phosphate buffer (pH 7.0). Subsequently, the cells were subjected to sonication (20 KHz, 5 min.) and then centrifuged at 15,000 r.p.m. for 60 min. By using the supernatant of enzyme fluid, the stability of each compound against β-lactamase was determined by the iodometric assay method. The results obtained were as set forth in Table 7-2. Each numeral shown in Table 7-2 is a relative activity value calculated by assuming as 100 the activity of the control Cephalorizine.

Table 7-2

| Compound | | Comparison of relative activity against β-lactamase | |
|---|---|---|---|
| | | Relative activity (%) | |
| | | Pr. vulgaris GN 76 | E. freundii GN 346 |
| Con-trol | Cephalorigine | 100 | 100 |
| | Sodium Cephalexin | 150 | 29 |
| | Sodium Cephaloglycin | 1300 | 0.3 |
| | Sodium Cephalothin | 105 | 17 |
| | Sodium Cephazoline | 440 | 150 |
| | Compound No. 63 | 6 | 0.2 |
| " | 67 | 5 | 0.4 |
| " | 69 | 4 | 0.1 |
| " | 72 | 7 | 0.2 |
| " | 73 | 4 | 0.1 |
| " | 74 | 5 | 0.03 |
| " | 76 | 11 | 1 |
| " | 81 | 6 | 0.4 |
| " | 84 | 10 | 1 |

From Tables 3 to 6, it is understood that the compounds of the present invention have a broader antibacterial spectrum and more excellent antibacterial activity against not only *Pseudomonas aeruginosa, Klebsiella pneumoniae,* and *Proteus* species but also many drug-resistant bacteria than the control ampicillin and cephaloglycin, i.e. compounds having an amino group at the α-position of the acyl group. It is also understood from Table 7-1 and Table 7-2 that the compounds of the present invention are far higher in resistance to β-lactamase than the control drugs.

As is clear from the above results, the compounds represented by the formula (Ie), among the compounds of the present invention, show prominent effects, and particularly preferable compounds are those of the formula (Ie), in which A represents a hydrogen atom, or an unsubstituted or substituted alkyl, alkenyl, aryl or aralkyl group; and $R^2$ and $R^3$ represent individually a hydrogen atom or an alkyl group.

The present penicillins and cephalosporins have generally low toxicity. For example, 6-[D(-)-α-(4-methyl-2,3-dioxo-1-piperazinocarbonylamino)-phenylacetamido]penicillanic acid and 6-[D(-)-α-(4-ethyl-2,3-dioxo-1-piperazinocarbonylamino)-phenylacetamido]penicillanic acid have $LD_{50}$ (i.v. in mouse having a weight of 19 ± 1 g) greater than 5 g/kg.

The compounds of formula (I) of the present invention may be administered not only in the form of free acids but also in the form of non-toxic salts or physiologically acceptable esters. Furthermore, the compounds, when in the form of physiologically unacceptable esters, are ordinarily put into use after bringing them into the form of free acids or non-toxic salts by removing the ester-forming group according to a conventional procedure known in this technical field.

The compounds of the present invention can be administered to humans and animals after formulating them into a physiological form such as a tablet, capsule, syrup, injection or the like which is usually adopted in the case of penicillin and cephalosporin type drugs.

Procedures for producing the compounds of the present invention are shown below with reference to examples.

EXAMPLE 1

(1) To a mixture comprising 2.5 g of 1-acetyl-3-oxopiperazine, 3.45 g of triethylamine and 20 ml of anhydrous dioxane was added a solution of 3.71 g of trimethylchlorosilane in 10 ml of anhydrous dioxane. The resulting mixture was refluxed for 17 hours and cooled to deposit triethylamine hydrochloride, which was then removed by filtration. The filtrate was dropped at −40° to −30° C. into a solution of 1.8 g of phosgene in 30 ml of anhydrous methylene chloride. After the dropping, the resulting mixture was elevated in temperature, and reacted at room temperature for 30 minutes. Subsequently, the excess phosgene and the solvent were removed by distillation under reduced pressure to obtain 3.5 g of pale brown, oily 4-acetyl-2-oxo-1-piperazinocarbonyl chloride.

IR (film) cm$^{-1}$: $\nu_{C=O}$ 1790, 1710, 1640

(2) A suspension of 1.0 g of 6-[D(-)-α-aminophenylacetamido]penicillanic acid in 20 ml of tetrahydrofuran containing 20% by volume of water was adjusted to a pH of 8.0 to 8.5 by gradual addition of triethylamine with stirring, and then cooled to 0° C. Into the thus treated suspension was dropped a solution of 900 mg of the aforesaid 4-acetyl-2-oxopiperazinocarbonyl chloride in 5 ml of tetrahydrofuran at said temperature over a period of 30 minutes. During this period, the pH of the suspension was maintained at 7.5 to 8.0 by gradual addition of triethylamine. Subsequently, the temperature of the resulting mixture was elevated to 5° to 10°

C., and the mixture was reacted at said temperature for 1 hour while maintaining the pH thereof at 7.5 to 8.0 by addition of triethylamine. After the reaction, the tetrahydrofuran was removed by reduced pressure distillation, and the residue was dissolved in a mixed solvent comprising 30 ml of ethyl acetate and 10 ml of water. The resulting solution was adjusted to a pH of 1.5 to 2 by addition of dilute hydrochloric acid with ice-cooling, and then the organic layer was separated off. The aqueous layer was re-extracted with 20 ml of ethyl acetate, and the resulting organic layer was combined with the aforesaid organic layer. The combined organic layer was washed with water, dried over anhydrous magnesium sulfate, and then ice-cooled. Into this organic layer was dropped a solution of 470 mg of a sodium salt of 2-ethylhexanoic acid in 20 ml of ethyl acetate to deposit white crystals. The deposited crystals were collected by filtration, washed with ethyl acetate and then dried to obtain 1.4 g of a sodium salt of 6-[D(-)-α-(4-acetyl-2-oxo-1-piperazinocarbonylamino)-phenylacetamido]penicillanic acid, m.p. 205° C. (decomp.), yield 94%.

IR (KBr) cm$^{-1}$: $\nu_{C=O}$ 1760 (lactam), 1600 - 1700 (—COO$^{\ominus}$, —CON<)

NMR [(CD$_3$)$_2$SO + D$_2$O]$\tau$values: 2.73 (5H), 4.35 (1H), 4.75 (2H), 5.75 (1H), 5.84 (2H), 6.42 (4H), 8.03 (3H), 8.52 (3H), 8.64 (3H)

The above-mentioned operation was repeated, except that the 4-acetyl-2-oxo-1-piperazinocarbonyl chloride was replaced by each of the reactive derivatives of compounds of formula (III) shown in Table 8, to obtain the respective objective compounds as shown in Table 8. The structure of each objective compound was confirmed by IR and NMR.

Table 8

| Reactive derivative of compound of formula (III) | Objective compound |
|---|---|
| Cl$_2$CHCO—N⌒N—COCl (2-oxopiperazine) | D(—)— Cl$_2$CHCO—N⌒N—CONHCHCONH—[penicillanate] (phenyl) COONa  m.p. (decomp.) 203 – 205° C, yield 73 % |
| CH$_3$(CH$_2$)$_4$CH$_2$CO—N⌒N—COCl | D(—)— CH$_3$(CH$_2$)$_4$CH$_2$CO—N⌒N—CONHCHCONH—[penicillanate] (phenyl) COONa  m.p. (decomp.) 202° C, yield 85.5 % |
| C$_6$H$_{11}$—CO—N⌒N—COCl | D(—)— C$_6$H$_{11}$—CO—N⌒N—CONHCHCONH—[penicillanate] (phenyl) COONa  m.p. (decomp.) 203 – 205° C, yield 87.5 % |
| CH$_3$CO—N(CH$_3$)⌒N—COCl | D(—)— CH$_3$SO$_2$—N⌒N—CONHCHCONH—[penicillanate] (phenyl) COONa  m.p. (decomp.) 199 – 200° C, yield 95 % |
| CH$_3$SO$_2$—N⌒N—COCl | D(—)— CH$_3$SO$_2$—N⌒N—CONHCHCONH—[penicillanate] (phenyl) COONa  m.p. (decomp.) 199° C, yield 80 % |
| | D(—)— |

Table 8-continued

| Reactive derivative of compound of formula (III) | Objective compound |
|---|---|
| 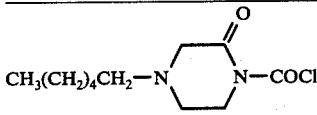 | 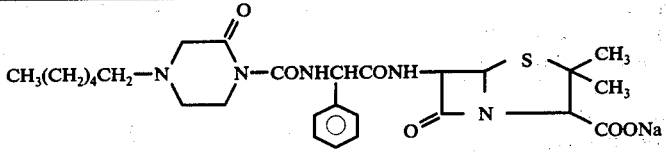<br>m.p. (decomp.) 171 – 174° C, yield 74 %<br>D(−)− |
| 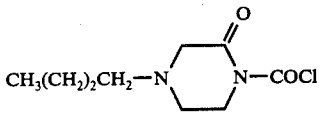 | 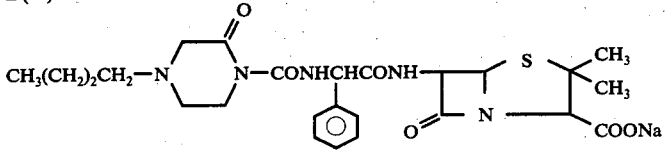<br>m.p. (decomp.) 158– 161° C, yield 69 %<br>D(−)− |
| 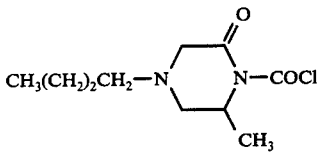 | 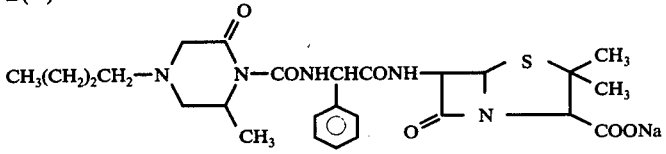<br>m.p. (decomp.) 188 – 190° C, yield 81 %<br>D(−)− |
| 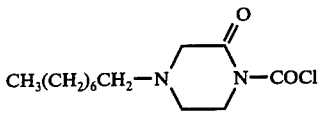 | 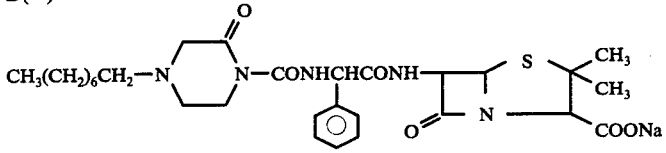<br>m.p. (decomp.) 132 – 134° C, yield 63 %<br>D(−)− |
| 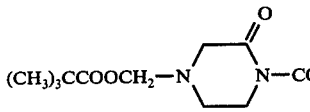 | 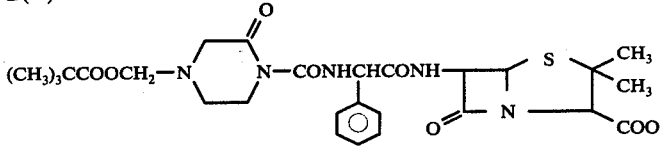<br>m.p. (decomp.) 218° C, yield 80 % |

EXAMPLE 2

(1) Into a solution of 1.74 g of a sodium salt of D(−)-α-aminophenylacetic acid in 30 ml of tetrahydrofuran containing 20% by volume of water which had been cooled to 0° C., a solution of 2.5 g of 4-acetyl-2-oxo-1-piperazinocarbonyl chloride in 5 ml of tetrahydrofuran was dropped at said temperature over a period of 30 minutes. During this period, the pH of the reaction solution was maintained at 11.0 to 12.0 by gradual addition of a 10% aqueous sodium hydroxide solution. Subsequently, the temperature of the resulting mixed solution was elevated to 5° to 10° C., and the solution was reacted at room temperature for 2 hours while maintaining the pH thereof at 10.0 to 11.0 by addition of a 10% aqueous sodium hydroxide solution. After the reaction, the tetrahydrofuran was removed by reduced pressure distillation. The residue was dissolved in a mixed solvent comprising 20 ml of water and 50 ml of ethyl acetate, and the resulting solution was adjusted to a pH of 1.0 to 1.5 by addition of dilute hydrochloric acid with ice-cooling. Subsequently, the organic layer was separated off, washed with water and then dried over anhydrous magnesium sulfate. To this organic layer, a solution of 1.66 g of a sodium salt of 2-ethylhexanoic acid in 20 ml of ethyl acetate was added to deposit white crystals. The deposited crystals were collected by filtration, sufficiently washed with ethyl acetate and then dried to obtain 1.89 g of a sodium salt of D(−)-α-(4-acetyl-2-oxo-1-piperazinocarbonylamino)phenylacetic acid, m.p. 115° C. (decomp.), yield 52%.

IR (KBr) cm$^{-1}$: —$\nu_{C=O}$ 1690, 1650–1600

(2) — To a suspension in 15 ml of anhydrous acetone of 833 mg of the above-mentioned sodium salt of D(−)-α-(4-acetyl-2-oxo-1-piperazinocarbonylamino)phenylacetic acid was added 10 mg of N-methylmorpholine. The resulting mixture was cooled to −20° to −15° C., and a solution of 286 mg of ethyl chlorocarbonate in 5 ml of anhydrous acetone was dropped into said mixture over a period of 5 minutes. Subsequently, the mixture was stirred at said temperature for 60 minutes. Into the thus treated mixture, a solution of 646 mg of a triethylamine salt of 6-aminopenicillanic acid in 30 ml of anhydrous methylene chloride was dropped at −40° to −30° C. over a period of 10 minutes. Thereafter, the mixture was reacted with stirring at −30° to −20° C. for 60 minutes, at −20° to −10° C. for 30 minutes, and at −10° to 0° C. for 30 minutes. After the reaction, the organic solvent was removed by reduced pressure distillation. The residue was dissolved in a mixed solvent comprising 50 ml of ethyl acetate and 20 ml of water, and the resulting solution was adjusted to a pH of 1.5 to 2.0 by addition of dilute hydrochloric acid with ice-cooling. Subsequently, the organic layer was separated off, sufficiently washed with water and then dried over anhydrous magnesium sulfate, and the ethyl acetate was removed by reduced pressure distillation. The residue was dissolved in 50 ml of acetone, and the resulting solution was mixed with a solution of 340 mg of a sodium salt of 2-ethylhexanoic acid in 20 ml of acetone with ice-cooling to deposit white crystals. The deposited crystals were collected by filtration, sufficiently washed with acetone and then dried to obtain 1.16 g of a sodium salt of 6-[D(−)-α-(4-acetyl-2-oxo-1-piperazinocarbonylamino)phenylacetamido]penicillanic acid, m.p. 205° C. (decomp.), yield 94%.

EXAMPLE 3

(1) — To a mixture comprising 1.0 g of 1-palmitoyl-3-oxo-piperazine, 0.6 g of triethylamine and 20 ml of anhydrous dioxane was added a solution of 0.65 g of trimethylchlorosilane in 10 ml of anhydrous dioxane. The resulting mixture was refluxed for 16 hours and cooled to deposit triethylamine hydrochloride, which was then removed by filtration. The filtrate was dropped at −40° to −30° C. into a solution of 0.6 g of phosgene in 30 ml of anhydrous methylene chloride. After the dropping, the temperature of the resulting mixture was elevated and the mixture was reacted at room temperature for 30 minutes. Subsequently, the excess phosgene and the solvent were removed by reduced pressure distillation to obtain 1.1 g of pale yellow, oily 4-palmitoyl-2-oxo-1-piperazinocarbonyl chloride.

IR (film) cm$^{-1}$: — $\nu_{C=O}$ 1740, 1660, 1640

(2) — A suspension of 1.0 g of 6-[D(−)-α-aminophenylacetamido]penicillanic acid in 20 ml of tetrahydrofuran containing 20% by volume of water was adjusted to a pH of 8.0 to 8.5 by gradual addition of triethylamine with stirring, and then cooled to 0° C. Into the thus treated suspension, a solution of 1.27 g of the aforesaid palmitoyl-2-oxo-1-piperazinocarbonyl chloride in 5 ml of tetrahydrofuran was dropped at said temperature over a period of 30 minutes. During this period, the pH of the suspension was maintained at 7.5 to 8.0 by gradual addition of triethylamine. Subsequently, the temperature of the resulting mixture was elevated to 5° to 10° C., and the mixture was reacted at said temperature for 1 hour while maintaining the pH thereof at 7.5 to 8.0 by addition of triethylamine. After the reaction, the tetrahydrofuran was removed by reduced pressure distillation, and the residue was dissolved in a mixed solvent comprising 30 ml of ethyl acetate and 10 ml of water. The resulting solution was adjusted to a pH of 1.0 to 2.0 by addition of dilute hydrochloric acid with ice-cooling, and then the organic layer was separated off. The aqueous layer was re-extracted with 20 ml of ethyl acetate, and the resulting organic layer was combined with the aforesaid organic layer. The combined organic layer was washed with water, and dried over anhydrous magnesium sulfate. This organic layer was concentrated under reduced pressure to remove the solvent, and the concentrate was charged into 10 ml of diisopropyl ether to deposit crystals. Thereafter, the crystals were collected by filtration to obtain 1.65 g of white crystals of 6-[D(−)-α-(4-palmitoyl-2-oxo-1-piperazinocarbonylamino)phenylacetamido]penicillanic acid, m.p. 121°–123° C. (decomp.), yield 80%.

IR (KBr) cm$^{-1}$: — $\nu_{C=O}$ 1770 (lactam), 1730 (—COOH), 1660–1630 (—CON<).

The above-mentioned operation was repeated, except that the 4-palmitoyl-2-oxo-1-piperazinocarbonyl chloride was replaced by each of the reactive derivatives of compounds of formula (III) shown in Table 9, to obtain respective objective compounds as shown in Table 9. The structure of each objective compound was confirmed by IR and NMR.

Table 9

| Reactive derivative of compound of formula (III) | Objective compound |
|---|---|
| CH$_3$(CH$_2$)$_5$CH$_2$CO—N◯N—COCl | D(−)— CH$_3$(CH$_2$)$_5$CH$_2$CO—N◯N—CONHCHCONH—[penicillanic structure] m.p. (decomp.) 151 – 153° C, yield 82 % |
| CH$_3$(CH$_2$)$_3$CH$_2$CO—N◯N—COCl | D(−)— CH$_3$(CH$_2$)$_3$CH$_2$CO—N◯N—CONHCHCONH—[penicillanic structure] m.p. (decomp.) 157 – 158° C, yield 83.3 % |
| ClCH$_2$CO—N◯N—COCl | D(−)— ClCH$_2$CO—N◯N—CONHCHCONH—[penicillanic structure] m.p. (decomp.) 215° C, yield 82.6 % |

Table 9-continued
| Reactive derivative of compound of formula (III) | Objective compound |
|---|---|
| 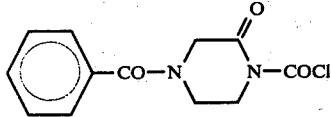 | 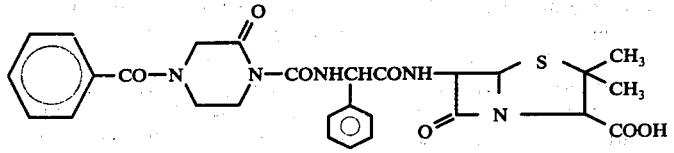<br>m.p. (decomp.) 120 – 124° C, yield 80 %<br>D(−)− |
| 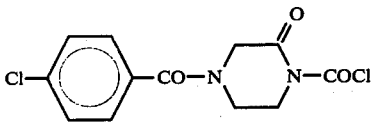 | 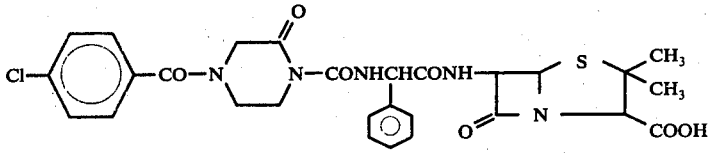<br>m.p. (decomp.) 120 – 123° C, yield 91 %<br>D(−)− |
| 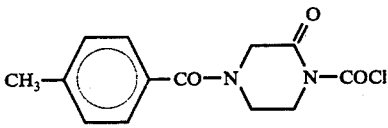 | 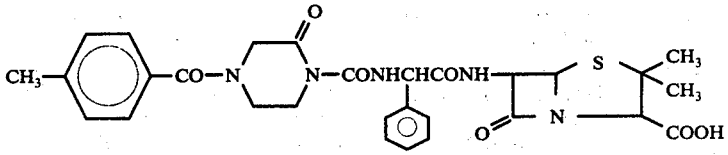<br>m.p. (decomp.) 105 – 108° C, yield 88.6 %<br>D(−)− |
| 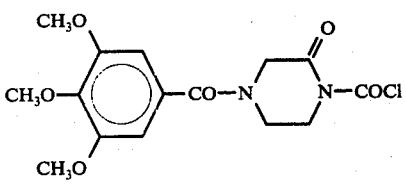 | 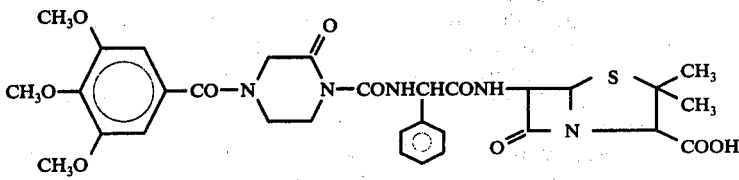<br>m.p. (decomp.) 120 – 124° C, yield 86.1 %<br>D(−)− |
| 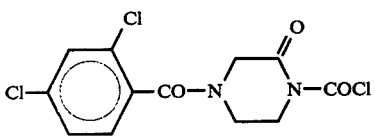 | 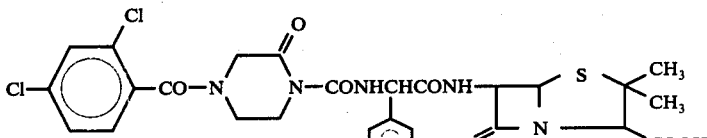<br>m.p. (decomp.) 130 – 133° C, yield 92 %<br>D(−)− |
| 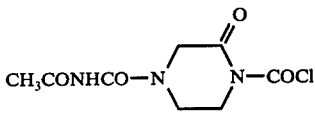 | 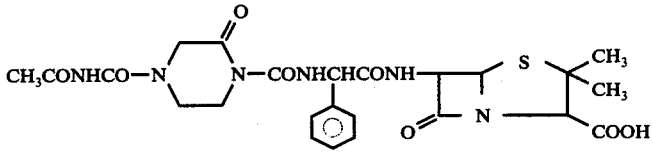<br>m.p. (decomp.) 172 – 176° C, yield 79.2 %<br>D(−)− |
| 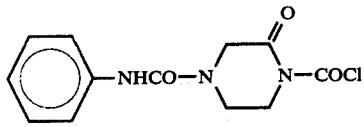 | 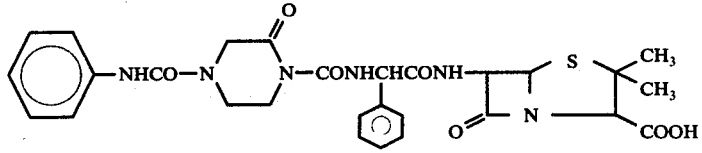<br>m.p. (decomp.) 168 – 170° C, yield 83.3 %<br>D(−)− |

Table 9-continued

| Reactive derivative of compound of formula (III) | Objective compound |
|---|---|
| 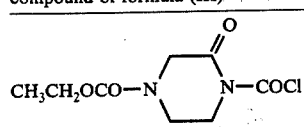 | 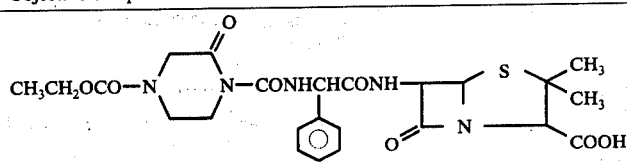 |
| | m.p. (decomp.) 86° C, yield 91 % |

EXAMPLE 4

(1) — To a solution of 6.4 g of 1-formyl-3-oxo-piperazine in 10 ml of anhydrous dimethylformamide was added 2.7 g of a sodium hydride (purity 53%) with ice-cooling, and the resulting mixture was reacted at room temperature for 1 hour. Subsequently, the mixture was incorporated with 7.1 g of methyl iodide and reacted for 10 hours. After the reaction, the dimethylformamide was removed by reduced pressure distillation to obtain 1-formyl-4-methyl-3-oxo-piperazine. This piperazine was dissolved in 70 ml of a 50% aqueous acetone solution containing 2.2 g of sodium hydroxide, and the resulting solution was reacted at room temperature for 3 hours. Thereafter, the solvent was removed by distillation under reduced pressure, and the residue was charged into acetone to deposit insolubles. The insolubles were separated by filtration, and the acetone was removed from the filtrate by distillation under reduced pressure. Subsequently, the residue was subjected to reduced pressure distillation to obtain 5.2 g of 1-methyl-2-oxo-piperazine, b.p. 104° C/4 mmHg, yield 91%.

(2) — Into a solution of 1.9 g of phosgene in 20 ml of anhydrous dioxane was dropped at 10° C. 20 ml of an anhydrous dioxane solution containing 2.0 g of 1-methyl-2-oxo-piperazine and 1.95 g of triethylamine, upon which reaction took place to deposit white crystals of triethylamine hydrochloride. The deposited crystals were removed by filtration, and the filtrate was concentrated to dryness to obtain 3.0 g of pale yellow, oily 4-methyl-3-oxo-1-piperazinocarbonyl chloride.

IR (film) cm$^{-1}$: — $\nu_{C=O}$ 1710, 1630

(3) — A suspension of 4.0 g of 6-[D(—)-α-aminophenylacetamido]penicillanic acid in 40 ml of tetrahydrofuran containing 20% by volume of water was adjusted to a pH of 8.0 to 8.5 by gradual addition of triethylamine with stirring, and then cooled to 0° C. Into the thus treated suspension, 10 ml of a tetrahydrofuran solution containing 2.2 g of the aforesaid 4-methyl-3-oxo-1-piperazinocarbonyl chloride was dropped. During this period, the pH of the suspension was maintained at 7.5 to 8.5 by gradual addition of triethylamine. Subsequently, the resulting mixture was reacted at said temperature for 30 minutes, and the temperature thereof was elevated to 10° to 15° C., after which the mixture was further reacted at said temperature for 90 minutes while maintaining the pH thereof at 7.5 to 8.0 by addition of triethylamine. After the reaction, the tetrahydrofuran was removed by distillation under reduced pressure, and the residue was dissolved in 30 ml of water. The resulting solution was washed with ethyl acetate, and then the aqueous layer was separated off. This aqueous layer was ice-cooled and then adjusted to a pH of 1.5 by addition of dilute hydrochloric acid to deposit white crystals. The deposited crystals were collected by filtration, washed several times with a small amount of water, dried, and then dissolved in 100 ml of acetone. To the resulting solution was added 1.9 g of a sodium salt of 2-ethylhexanoic acid with ice-cooling to deposit white crystals, which were then collected by filtration to obtain 5.4 g of a sodium salt of 6-[D(—)-α-(4-methyl-3-oxo-1-piperazinocarbonylamino)phenylacetamido]-penicillanic acid, m.p. 195° C. (decomp.), yield 92%.

IR (KBr) cm$^{-1}$: — $\nu_{C=O}$ 1760 (lactam), 1600–1660 (—CON<, —COO$^{\ominus}$)

NMR [(CD$_3$)$_2$SO + D$_2$O] τ values: 2.62 (5H), 4.48 (1H), 4.56 (2H), 5.97 (3H), 6.63–6.39 (4H), 7.13 (3H), 8.46 (3H), 8.55 (3H)

The above-mentioned operation was repeated, except that the 4-methyl-3-oxo-1-piperazinocarbonyl chloride was replaced by each of the reactive derivatives of compounds of formula (III) shown in Table 10, to obtain respective objective compounds as shown in Table 10. The structure of each objective compound was confirmed by IR and NMR.

Table 10

| Reactive derivative of compound of formula (III) | Objective compound |
|---|---|
| 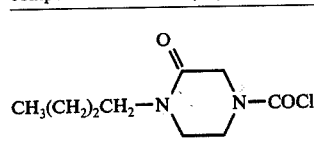 | D(—)—<br>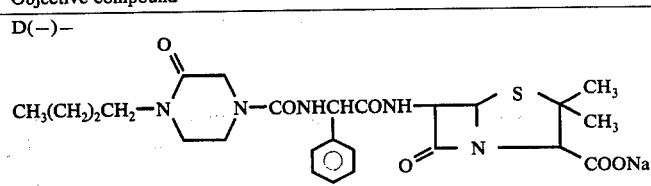 |
| | m.p. (decomp.) 206 – 207° C, yield 90 % |
| 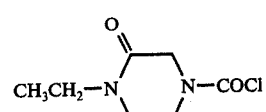 | D(—)—<br>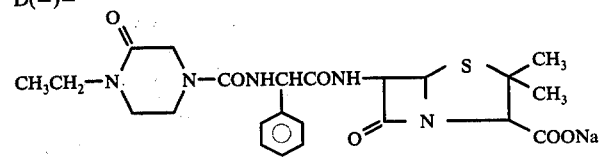 |

Table 10-continued

| Reactive derivative of compound of formula (III) | Objective compound |
|---|---|
| (CH₃)₂CH—N(piperazinone)—COCl | m.p. (decomp.) 207° C, yield 96 %<br>D(−)−<br>(CH₃)₂CH—N(piperazinone)—CONHCHCONH—(β-lactam with S, C(CH₃)₂, COONa), phenyl |
| CH₃(CH₂)₃CH₂—N(piperazinone)—COCl | m.p. (decomp.) 208° C, yield 87 %<br>D(−)−<br>CH₃(CH₂)₃CH₂—N(piperazinone)—CONHCHCONH—(β-lactam), phenyl |
| (CH₃)₂CHCH₂CH₂—N(piperazinone)—COCl | m.p. (decomp.) 200° C, yield 96 %<br>D(−)−<br>(CH₃)₂CHCH₂CH₂—N(piperazinone)—CONHCHCONH—(β-lactam), phenyl |
| CH₃(CH₂)₂CH₂—N(3-methylpiperazinone)—COCl | m.p. (decomp.) 185° C, yield 90 %<br>D(−)−<br>CH₃(CH₂)₂CH₂—N(3-methylpiperazinone)—CONHCHCONH—(β-lactam), phenyl |
| CH₃(CH₂)₂CH₂—N(piperazinone with CH₃)—COCl | m.p. (decomp.) 193 – 197° C, yield 74 %<br>D(−)−<br>CH₃(CH₂)₂CH₂—N(piperazinone with CH₃)—CONHCHCONH—(β-lactam), phenyl |
| CH₃(CH₂)₂CH₂—N(piperazinone, CH₃ substituent)—COCl | m.p. (decomp.) 199 – 202° C, yield 93 %<br>D(−)−<br>CH₃(CH₂)₂CH₂—N(piperazinone, CH₃)—CONHCHCONH—(β-lactam), phenyl |
| Ph-CH₂—N(piperazinone)—COCl | m.p. (decomp.) 191 – 194° C, yield 88 %<br>D(−)−<br>Ph-CH₂—N(piperazinone)—CONHCHCONH—(β-lactam), phenyl |
| HOCH₂CH₂—N(piperazinone)—COCl | m.p. (decomp.) 100 – 105° C, yield 90 %<br>D(−)−<br>HOCH₂CH₂—N(piperazinone)—CONHCHCONH—(β-lactam), phenyl |
| CH₃CO—N(3-methylpiperazinone)—COCl | m.p. (decomp.) 100 – 105° C, yield 67 %<br>D(−)−<br>CH₃CO—N(3-methylpiperazinone)—CONHCHCONH—(β-lactam), phenyl |

Table 10-continued

| Reactive derivative of compound of formula (III) | Objective compound |
|---|---|
| (structure: H₂NCO—N(ring with O, CH₃)N—COCl) | m.p. (decomp.) 202° C, yield 66 % <br> D(−)− <br> (structure: H₂NCO—N(ring with O, CH₃)N—CONHCHCONH—[β-lactam with S, C(CH₃)₂, COONa], phenyl) |
| (structure: HN(ring with O)N—COCl) | m.p. (decomp.) 215° C, yield 65 % <br> D(−)− <br> (structure: HN(ring with O)N—CONHCHCONH—[β-lactam with S, C(CH₃)₂, COONa], phenyl) |
| (structure: HN(ring with O, CH₃, CH₃)N—COCl) | m.p. (decomp.) 213° C, yield 70 % <br> D(−)− <br> (structure: HN(ring with O, CH₃, CH₃)N—CONHCHCONH—[β-lactam with S, C(CH₃)₂, COONa], phenyl) |
| (structure: HN(ring with O, CH₃)N—COCl) | m.p. (decomp.) 203 – 206° C, yield 82 % <br> D(−)− <br> (structure: HN(ring with O, CH₃)N—CONHCHCONH—[β-lactam with S, C(CH₃)₂, COONa], phenyl) |
| (structure: HN(ring with O, CH₂COOCH₂CH₃)N—COCl) | m.p. (decomp.) 216 – 218° C, yield 87 % <br> D(−)− <br> (structure: HN(ring with O, CH₂COOCH₂CH₃)N—CONHCHCONH—[β-lactam with S, C(CH₃)₂, COONa], phenyl) |
| (structure: HN(ring with O, CH₃)N—COCl) | m.p. (decomp.) 200° C, yield 98 % <br> D(−)− <br> (structure: HN(ring with O, CH₃)N—CONHCHCONH—[β-lactam with S, C(CH₃)₂, COONa], phenyl) <br> m.p. (decomp.) 208° C, yield 75 % |

EXAMPLE 5

(1) — A solution of 1.0 g of a sodium salt of D(−)-α-aminophenyl acetic acid in 20 ml of tetrahydrofuran containing 20% by volume of water was cooled to 0° to 5° C. To this solution was added 1.2 g of 2-methyl-3-oxo-1-piperazinocarbonyl chloride over a period of 10 minutes. During this period, the pH of the solution was maintained at 11.0 to 12.0 by gradual addition of a 10% aqueous sodium hydroxide solution. The solution was reacted at said temperature for 1 hour, and the temperature thereof was elevated to 5° to 10° C, after which the mixture was further reacted at said temperature for 2 hours, while maintaining the pH thereof at 10.0 to 11.0 by addition of a 10% aqueous sodium hydroxide solution. After the reaction, tetrahydrofuran was removed by distillation under reduced pressure, and the residue was dissolved in a mixed solvent comprising 20 ml of water and 50 ml of ethyl acetate. The resulting solution was adjusted to a pH of 1.5 by addition of dilute hydrochloric acid with ice-cooling, and then the organic layer was separated off. The aqueous layer was further extracted with 50 ml of ethyl acetate, and the resulting organic layer was combined with the aforesaid organic layer. The combined organic layer was washed with water and then dried over anhydrous magnesium sulfate. To this organic layer was added 0.9 g of a sodium salt of 2-ethylhexanoic acid to deposit white crystals. The deposited crystals were collected by filtration and then dried to obtain 1.26 g of white crystals of a sodium salt of D(−)-α-(2-methyl-3-oxo-1-piperazinocarbonylamino)phenylacetic acid, m.p. 215° C. (decomp.), yield 70%.

IR (KBr) cm$^{-1}$: — $\nu_{C=O}$ 1650–1590

(2) — To a suspension in 15 ml of anhydrous acetone of 1.0 g of the above-mentioned sodium salt of D(−)-α-(2-methyl-3-oxo-1-piperazinocarbonylamino)phenylacetic acid was added 10 mg of N-methylmorpholine. The resulting mixture was cooled to −20° to −15° C., and a solution of 380 mg of ethyl chlorocarbonate in 5 ml of anhydrous acetone was dropped into said mixture over a period of 5 minutes. Subsequently, the mixture was stirred at said temperature for 60 minutes, and then cooled to −40° to −30° C. Into the thus treated mixture was dropped a solution of 960 mg of a triethylamine salt of 6-aminopenicillanic acid in 10 ml of anhydrous methylene chloride over a period of 10 minutes. Thereafter, the mixture was reacted with stirring at −30° to −20° C. for 60 minutes, at −20° to −10° C. for 30 minutes, and at −10° to 0° C. for 30 minutes. After the reaction, the organic solvent was removed by distillation under reduced pressure. The residue was dissolved in a mixed solvent comprising 20 ml of water and 50 ml of ethyl acetate, and the resulting solution was adjusted to a pH of 1.5 by addition of dilute hydrochloric acid with ice-cooling. Subsequently, the organic layer was separated off, sufficiently washed with water and then dried over anhydrous magnesium sulfate. To this organic layer was added 0.5 g of a sodium salt of 2-ethylhexanoic acid with ice-cooling to deposit white crystals. The deposited crystals were collected by filtration, and then dried to obtain 1.39 g of a sodium salt of 6-[D(−)-α-(2-methyl-3-oxo-1-piperazinocarbonylamino)-phenylacetamido]penicillanic acid, m.p. 208° C. (decomp.), yield 90%.

In the same manner as above, 2.0 g of a sodium salt of 6-[D(−)-α-(4-ethyl-3-oxo-1-piperazinocarbonylamino)-propionamido]penicillanic acid, m.p. 195° C. (decomp.), yield 86%, was obtained from 1.59 g of a sodium salt of D(−)-α-(4-ethyl-3-oxo-1-piperazinocarbonylamino)-propionic acid and 1.59 g of a triethylamine salt of 6-aminopenicillanic acid.

IR (KBr) cm$^{-1}$: — $\nu_{C=O}$ 1760 (lactam), 1680–1600 (—CON<, —COO$^\ominus$)

EXAMPLE 6

(1) — Into a solution of 0.5 g of phosgene in 10 ml of anhydrous dioxane was dropped at 10° C. 10 ml of anhydrous dioxane containing 0.56 g of 1-allyl-2-oxo-piperazine and 0.5 g of triethylamine, upon which reaction took place to deposit white crystals of triethylamine hydrochloride. Subsequently, the deposited crystals were collected by filtration, and the filtrate was concentrated to dryness to obtain 800 mg of pale yellow, oily 4-allyl-3-oxo-1-piperazinocarbonyl chloride.

IR (film) cm$^{-1}$: — $\nu_{C=O}$ 1720, 1640

(2) — A suspension of 1.4 g of 6[D(−)-α-amino-phenylacetamido]penicillanic acid in tetrahydrofuran containing 20% by volume of water was adjusted to a pH of 8.0 to 8.5 by gradual addition of triethylamine with stirring, and then cooled to 0° C. Into the thus treated suspension was dropped 10 ml of a tetrahydrofuran solution containing 800 mg of the aforesaid 4-allyl-3-oxo-1-piperazinocarbonyl chloride. During this period, the pH of the suspension was maintained at 7.5 to 8.5 by gradual addition of triethylamine. Subsequently, the resulting mixture was reacted at said temperature for 30 minutes, and the temperature thereof was then elevated to 10° to 15° C., after which the mixture was further reacted at said temperature for 90 minutes while maintaining the pH thereof at 7.5 to 8.0 by addition of triethylamine. After the reaction, the tetrahydrofuran was removed by distillation under reduced pressure, and the residue was dissolved in 20 ml of water. The resulting solution was washed with ethyl acetate, and the aqueous layer was then separated off. This aqueous layer was ice-cooled and adjusted to a pH of 1.5 by addition of dilute hydrochloric acid to deposit white crystals. The deposited crystals were collected by filtration, sufficiently washed with water and then dried to obtain 1.8 g of 6-[D(−)-α-(4-allyl-3-oxo-1-piperazinocarbonylamino)phenylacetamido]penicillanic acid, m.p. 92° C. (decomp.), yield 90%.

IR (KBr) cm$^{-1}$: — $\nu_{C=O}$ 1760 (lactam), 1720–1620 (—COOH, —CON<)

The above-mentioned operation was repeated, except that the 4-allyl-3-oxo-1-piperazinocarbonyl chloride was replaced by each of the reactive derivatives of compounds of formula (III) shown in Table 11, to obtain respective objective compounds as shown in Table 11. The structure of each objective compound was confirmed by IR and NMR.

Table 11

| Reactive derivative of compound of formula (III) | Objective compound |
|---|---|
| CH$_2$=CHCH(CH$_3$)—N[piperazinone]N—COCl | D(−)— CH$_2$=CHCH(CH$_3$)—N[piperazinone]N—CONHCHCONH—[penicillin nucleus]—COOH  m.p. (decomp.) 102° C, yield 80 % |
| CH$_2$=CCH$_2$(CH$_3$)—N[piperazinone]N—COCl | D(−)— CH$_2$=CCH$_2$(CH$_3$)—N[piperazinone]N—CONHCHCONH—[penicillin nucleus]—COOH  m.p. (decomp.) 90° C, yield 85 % |
| CH$_3$CH=HCCH$_2$—N[piperazinone]N—COCl  (trans—) | D(−)— CH$_3$CH=HCCH$_2$—N[piperazinone]N—CONHCHCONH—[penicillin nucleus]—COOH  (trans—) m.p. (decomp.) 95° C, yield 84 %  D(−)— |

Table 11-continued

| Reactive derivative of compound of formula (III) | Objective compound |
|---|---|
| 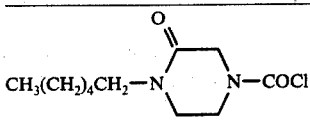 CH₃(CH₂)₄CH₂—N⟨⟩N—COCl | 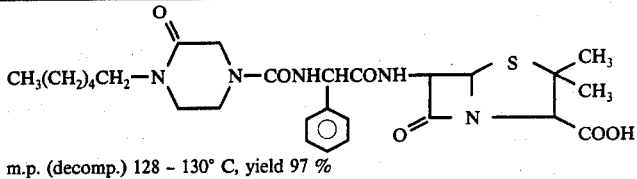 CH₃(CH₂)₄CH₂—N⟨⟩N—CONHCHCONH—[β-lactam]—S—C(CH₃)₂—COOH, Ph<br>m.p. (decomp.) 128 – 130° C, yield 97 %<br>D(−)— |
| CH₃(CH₂)₅CH₂—N⟨⟩N—COCl | CH₃(CH₂)₅CH₂—N⟨⟩N—CONHCHCONH—[β-lactam], Ph<br>m.p. (decomp.) 120° C, yield 94 %<br>D(−)— |
| CH₃(CH₂)₆CH₂—N⟨⟩N—COCl | CH₃(CH₂)₆CH₂—N⟨⟩N—CONHCHCONH—[β-lactam], Ph<br>m.p. (decomp.) 110° C, yield 98 %<br>D(−)— |
| CH₃(CH₂)₁₀CH₂—N⟨⟩N—COCl | CH₃(CH₂)₁₀CH₂—N⟨⟩N—CONHCHCONH—[β-lactam], Ph<br>m.p. (decomp.) 106° C, yield 96 %<br>D(−)— |
| H—[cyclopentyl]—N⟨⟩N—COCl | H—[cyclopentyl]—N⟨⟩N—CONHCHCONH—[β-lactam], Ph<br>m.p. (decomp.) 134° C, yield 87 %<br>D(−)— |
| Ph—NHCO—N⟨⟩N—COCl | Ph—NHCO—N⟨⟩N—CONHCHCONH—[β-lactam], Ph<br>m.p. (decomp.) 150 – 153° C, yield 76 %<br>D(−)— |
| HN⟨⟩(Ph)—N—COCl | HN⟨⟩(Ph)—N—CONHCHCONH—[β-lactam], Ph<br>m.p. (decomp.) 125 – 128° C, yield 79.5 % |

EXAMPLE 7

Using 0.63 g of 6-[D(−)-α-aminophenylacetamido]-penicillanic acid and 600 mg of a hydrochloride of 4-(N-morpholinomethyl)-3-oxo-1-piperazinocarbonyl chloride, the same operation as in Example 6 was repeated to obtain 0.63 g of 6-{D(−)-α-[4-(N-morpholinomethyl)-3-oxo-1-piperazinocarbonylamino]-phenylacetamido}penicillanic acid, m.p. 85° C. (decomp.), yield 60%.

IR (KBr) cm⁻¹: — $\nu_{C=O}$: 1770 (lactam), 1600 –1680 (—COO⁻, —CON<)

EXAMPLE 8

Using 5.0 g of a hydrochloride of pivaloyloxymethyl ester of 6-[D(−)-α-aminophenylacetamido]-penicillanic acid and 1.94 g of 2-methyl-3-oxo-1-piperazinocarbonyl chloride, the same operation as in Example 6 was repeated to obtain 5.2 g of a pivaloyloxymethyl ester of 6-[D(−)-α-(2-methyl-3-oxo-1-piperazinocarbonylamino)phenylacetamido]-penicillanic acid, m.p. 140° C. (decomp.), yield 80%.

IR (KBr) cm⁻¹: — $\nu_{C=O}$ 1740–1770 (lactam, ester) 1630–1670 (—CON<)

EXAMPLE 9

(1)—Into a mixture comprising 8.0 g of 4-acetyl-2,5-dioxo-piperazine, 5.0 g of triethylamine and 100 ml of anhydrous tetrahydrofuran was dropped 6.0 g of trimethylchlorosilane with stirring at room temperature. After the dropping, the resulting mixture was reacted at said temperature for 2 hours to deposit triethylamine hydrochloride. The deposited hydrochloride was separated by filtration, and the filtrate was dropped at 0° to 5° C. into 100 ml of an anhydrous tetrahydrofuran solution containing 10.0 g of phosgene. After completion of the dropping, the resulting mixture was stirred at 10° to 15° C. for 3 hours to terminate the reaction. Subsequently, the tetrahydrofuran and the excess phosgene were removed by distillation under reduced pressure to obtain 11.0 g of oily 4-acetyl-2,5-dioxo-1-piperazinocarbonyl chloride.

(2)—A suspension of 17.5 g of 6-[D(−)-α-aminophenylacetamido]penicillanic acid in 200 ml of tetrahydrofuran containing 20% by volume of water was adjusted to a pH of 8.0 to 8.5 by gradual addition or triethylamine with stirring at 10° to 15° C. to form a homogeneous solution. Into this solution was dropped a solution of 11.0 g of the aforesaid 4-acetyl-2,5-dioxo-1-piperazinocarbonyl chloride in 30 ml of tetrahydrofuran at 0° C. over a period of 30 minutes. During this period, the pH of the reaction solution was maintained at 7.5 to 8.0 by gradual addition of triethylamine. Subsequently, the temperature of the resulting mixed solution was elevated to 5° to 10° C. and the solution was further reacted for 1 hour while maintaining the pH thereof at 7.5 to 8.0 by addition of triethylamine. After completion of the reaction, the tetrahydrofuran was removed by distillation under reduced pressure. To the residue was added 100 cc of N hydrochloric acid at 0° to 10° C., and the resulting mixture was stirred for 30 minutes to deposit white crystals. The deposited crystals were collected by filtration, and again suspended in water. The resulting aqueous suspension was adjusted to a pH of 8.0 by gradual addition of triethylamine at 5° to 10° C., and then freed from insolubles by filtration. The filtrate was adjusted to a pH of 1.5 by gradual addition of N hydrochloric acid to deposit crystals. The deposited crystals were collected by filtration, washed with water and then dried to obtain 21.2 g of 6-[D(−)-α-(4-acetyl-2,5-dioxo-1-piperazinocarbonylamino)phenylacetamido]-penicillanic acid, m.p. 162°–164° C. (decomp.), yield 80%.

IR (KBr) cm$^{-1}$: $\nu_{C=O}$ 1770 (lactam), 1730–1660 (—COOH, —CON<)

NMR ((CD$_3$)$_2$CO)τ values:
0.23 (1H), 2.65 (5H), 4.26 (1H), 4.33–4.63 (2H), 5.38 (4H), 5.68 (1H), 7.55 (3H), 8.47 (3H), 8.53 (3H)

The above-mentioned operation was repeated, except that the 4-acetyl-2,5-dioxo-1-piperazinocarbonyl chloride was replaced by each of the reactive derivatives of compounds of formula (III) shown in Table 12, to obtain respective objective compounds as shown in Table 12. The structure of each objective compound was confirmed by IR and NMR.

Table 12

| Reactive derivative of compound of formula (III) | Objective compound |
|---|---|
| Ph–CO–N(piperazine-2,5-dione)–N–COCl | D(−)– Ph–CO–N(piperazine-2,5-dione)–N–CONHCHCONH–(penicillanic acid with phenyl); m.p. (decomp.) 88° C, yield 60 % |
| CH$_3$–N(piperazine-2,5-dione)–N–COCl | D(−)– CH$_3$–N(piperazine-2,5-dione)–N–CONHCHCONH–(penicillanic acid with phenyl); m.p. (decomp.) 179 – 181° C, yield 83 % |
| Ph–CH$_2$–N(piperazine-2,5-dione)–N–COCl | D(−)– Ph–CH$_2$–N(piperazine-2,5-dione)–N–CONHCHCONH–(penicillanic acid with phenyl); m.p. (decomp.) 88° C, yield 82 % |
| Spiro: HN–(piperazine-2,5-dione with spiro cyclohexyl H)–N–COCl | D(−)– Spiro: HN–(piperazine-2,5-dione with spiro cyclohexyl H)–N–CONHCHCONH–(penicillanic acid with phenyl); m.p. 214 – 215° C, yield 89.6 % |
| D(−)– | |

Table 12-continued

| Reactive derivative of compound of formula (III) | Objective compound |
|---|---|
| [structure: HN-piperazine-2,5-dione-N—COCl] | [structure with phenylacetic penicillin]<br>m.p. (decomp.) 176 – 181° C, yield 84.4 %<br>D(−)− |
| [structure: HN-piperazine-2,5-dione with phenyl, CH₃—N—COCl] | [structure]<br>m.p. (decomp.) 148 – 151° C, yield 92 %<br>D(−)− |
| [structure: PhCH₂—N-piperazinone—N—COCl] | [structure]<br>m.p. (decomp.) 95 – 100° C, yield 91 %<br>D(−)− |
| [structure: Cl₃CCH₂OCO—N-piperazinone—N—COCl] | [structure]<br>m.p. (decomp.) 120 – 125° C, yield 92 %<br>D(−)− |
| [structure: PhCH₂—N-piperazinone with phenyl, CH₃—N—COCl] | [structure]<br>m.p. (decomp.) 147 – 149° C, yield 89 % |

EXAMPLE 10

(1)—A suspension of 8.0 g of D(−)-α-aminophenyl acetic acid in 80 ml of tetrahydrofuran was adjusted to a pH of 11.5 by gradual addition of a N sodium hydroxide solution with stirring to form a homogeneous solution. This solution was cooled to 0° C., and 15 ml of a tetrahydrofuran solution containing 11 g of 4-acetyl-2,5-dioxo-1-piperazinocarbonyl chloride was dropped at said temperature into said solution over a period of 30 minutes. During this period, the pH of the reaction solution was maintained at 10.5 to 11.0 by gradual addition of a N sodium hydroxide solution. Subsequently, the temperature of the resulting mixed solution was elevated to 5° to 10° C., and the mixture was further reacted for 1 hour, upon which D(−)-α-aminophenylacetic acid deposited. After completion of the reaction, the deposited acid was separated by filtration, and the filtrate was concentrated under reduced pressure to remove tetrahydrofuran. The residue was dissolved in a mixed solvent comprising 10 ml of water and 80 ml of ethyl acetate, and the resulting solution was adjusted to a pH of 1.0 by addition of dilute hydrochloric acid with ice-cooling. Subsequently, the organic layer was separated off, dried over anhydrous magnesium sulfate, and then charged into 100 ml of an ethyl acetate solution containing 8.3 g of sodium 2-ethylhexanoate to deposit crystals. The deposited crystals were collected by filtration, washed with acetone, and then dried over $P_2O_5$ to obtain 7.9 g of a sodium salt of D(−)-α-(4-acetyl-2,5-dioxo-1-piperazinocarbonylamino)phenylacetic acid, m.p. 104° C. (decomp.), yield 42%.

IR (KBr) $cm^{-1}$: — $\nu_{C=O}$ 1690–1650, 1600–1590

(2)—To a suspension in 25 ml of anhydrous acetone of 1.75 g of the aforesaid sodium salt of D(−)-α-(4-acetyl-2,5-dioxo-1-piperazinocarbonylamino)phenyl acetic acid was added 20 mg of N-methylmorpholine, and the resulting mixture was cooled to −20° to −15° C. Into this mixture was dropped a solution of 0.57 g of ethyl chlorocarbonate in 5 ml of anhydrous acetone over a period of 5 minutes, and the mixture was stirred at said temperature for 60 minutes. Subsequently, a solution of 1.29 g of a triethylamine salt of 6-aminopenicillanic acid in 30 ml of anhydrous methylene chloride was dropped into said mixture at −40° to −30° C. over a period of 10 minutes. The temperature of the resulting mixture was elevated from −30° C. to 0° C., and the mixture was then reacted at said temperature for about 2 hours.

After the reaction, the solvent was removed by distillation under reduced pressure. The residue was charged into 30 ml of water, and the resulting mixture was freed from insolubles by filtration with ice-cooling. The filtrate was adjusted to a pH of 1.5 to 2.0 by addition of dilute hydrochloric acid to deposit crystals. The deposited crystals were collected by filtration, sufficiently washed with water, and then dried to obtain 2.34 g of 6-[D(−)-α-(4-acetyl-2,5-dioxo-1-piperazinocarbonylamino)phenylacetamido]penicillanic acid, m.p. 162°-164° C. (decomp.), yield 90%.

In the same manner as above, 530 mg of 6-[D(−)-α-(4-benzyl-2,2-pentamethylene-3,5-dioxo-1-piperazinocarbonylamino)phenylacetamido]penicillanic acid, m.p. 95°-100° C., yield 82.68%, was obtained from 450 mg of D(−)-α-(4-benzyl-2,2-pentamethylene-3,5-dioxo-1-piperazinocarbonylamino)phenylacetic acid and 320 mg of a triethylamine salt of 6-aminopenicillanic acid.

IR (KBr) cm$^{-1}$: — $\nu_{C=O}$ 1770 (Lactam), 1700–1660 (—COOH, —CON<)

EXAMPLE 11

(1)—Into a mixture comprising 8 g of a diethyl ester of oxalic acid and 8 ml of ethanol was dropped at room temperature 4.4 g of N-ethyl ethylenediamine. The resulting mixture was allowed to react for 3 hours, an then heated to remove the ethanol. Subsequently, the residue was recrystallized from 10 ml of dioxane to obtain 5.4 g of 1-ethyl-2,3-dioxopiperazine, m.p. 124° C., yield 76.0%.

(2)—To a suspension of 0.71 g of the abovementioned 1-ethyl-2,3-dioxo-piperazine in 15 ml of anhydrous dioxane were added with stirring 0.70 g of trimethylsilyl chloride and 0.83 ml of triethylamine. The resulting mixture was stirred at room temperature for 20 hours to deposit triethylamine hydrochloride. This hydrochloride was separated by filtration, and the filtrate was dropped at 5° to 10° C. into a solution of 0.70 g of phosgene in 10 ml of anhydrous tetrahydrofuran. Subsequently, the resulting mixture was reacted at 5° to 10° C. for 30 minutes and at room temperature for 2 hours, and then the solvent was removed by distillation under reduced pressure to obtain 1.0 g of pale yellow crystals of 4-ethyl-2,3-dioxo-1-piperazinocarbonyl chloride.

IR (KBr) cm$^{-1}$: — $\nu_{C=O}$ 1780, 1660

(3)—A suspension of 1.75 g of 6-[D(−)-α-aminophenylacetamido]penicillanic acid in 50 ml of tetrahydrofuran containing 20% by volume of water was adjusted to a pH of 8.0 to 8.5 by addition of triethylamine with stirring to form a solution. This solution was cooled to 0° to 5° C., and then 7 ml of an anhydrous tetrahydrofuran solution containing 1.0 g of the aforesaid 4-ethyl-2,3-dioxo-1-piperazinocarbonyl chloride was dropped into the solution. During this period, the pH of the reaction solution was maintained at 7.5 to 8.0 by gradual addition of triethylamine. The resulting mixed solution was reacted at said temperature for 30 minutes and then at 5° to 10° C. for 1 hour, while maintaining the pH thereof at 7.5 to 8.0. After the reaction, the tetrahydrofuran was removed by distillation under reduced pressure, and the residue was dissolved in 20 ml of water and then washed two times with 20 ml of ethyl acetate. To the aqueous layer was again added 50 ml of ethyl acetate, and the resulting mixture was adjusted to a pH of 1.5 by gradual addition of dilute hydrochloric acid with ice-cooling. Subsequently, the ethyl acetate layer was separated off, sufficiently washed with water, and then dried over anhydrous magnesium sulfate. Into the thus treated layer was dropped 10 ml of an ethyl acetate solution containing 0.83 g of sodium 2-ethylhexanoate to deposit white crystals. The deposited crystals were collected by filtration, sufficiently washed with ethyl acetate, washed with diethyl ether, and then dried to obtain 2.4 g of a sodium salt of 6-[D(−)-α-(4-ethyl-2,3-dioxo-1-piperazinocarbonylamino)-phenylacetamido]penicillanic acid, m.p. 183°–185° C. (decomp.), yield 89%.

IR (KBr) cm$^{-1}$: $\nu_{C=O}$ 1765 (lactam), 1720–1670 (—CON<), 1600 (—COO$^{\ominus}$)

NMR ((CD$_3$)$_2$SO + D$_2$O) τ values:
2.62 (5H), 4.31 (1H), 4.50 (1H), 4.70 (1H), 6.05 (1H), 6.35 - 6.65 (6H), 8.49 (3H), 8.60 (3H), 8.91 (3H)

The above-mentioned operation was repeated, except that the 4-ethyl-2,3-dioxo-1-piperazinocarbonyl chloride was replaced by each of the reactive derivatives of compounds of formula (III) shown in Table 13, to obtain respective objective compounds as shown in Table 13. The structure of each objective compound was confirmed by IR and NMR.

Table 13

| Reactive derivative of compound of formula (III) | Objective compound |
|---|---|
| CH$_3$—N(piperazine-2,3-dione)N—COCl | D(−)− CH$_3$—N(piperazine-2,3-dione)N—CONHCHCONH—(penicillanate)COONa (phenyl) <br> m.p. (decomp.) 170° C, yield 84 % |
| CH$_3$CH$_2$CH$_2$—N(piperazine-2,3-dione)N—COCl | D(−)− CH$_3$CH$_2$CH$_2$—N(piperazine-2,3-dione)N—CONHCHCONH—(penicillanate)COONa (phenyl) <br> m.p. (decomp.) 170° C, yield 86 % <br> D(−)− |

Table 13-continued

| Reactive derivative of compound of formula (III) | Objective compound |
|---|---|
| CH$_3$(CH$_2$)$_2$CH$_2$—piperazine-2,3-dione—N—COCl | CH$_3$(CH$_2$)$_2$CH$_2$—piperazine-2,3-dione—N—CONHCHCONH—penicillanate Na, phenyl side chain<br>m.p. (decomp.) 190° C, yield 87 %<br>D(−)− |
| (CH$_3$)$_2$CH—piperazine-2,3-dione—N—COCl | (CH$_3$)$_2$CH—piperazine-2,3-dione—N—CONHCHCONH—penicillanate Na, phenyl<br>m.p. (decomp.) 186° C, yield 85 %<br>D(−)− |
| CH$_3$COOCH$_2$CH$_2$—piperazine-2,3-dione—N—COCl | CH$_3$COOCH$_2$CH$_2$—piperazine-2,3-dione—N—CONHCHCONH—penicillanate Na, phenyl<br>m.p. (decomp.) 175° C, yield 79 %<br>D(−)− |
| CH$_2$=CHCH$_2$—piperazine-2,3-dione—N—COCl | CH$_2$=CHCH$_2$—piperazine-2,3-dione—N—CONHCHCONH—penicillanate Na, phenyl<br>m.p. (decomp.) 198 − 200° C, yield 75 %<br>D(−)− |
| phenyl—piperazine-2,3-dione—N—COCl | phenyl—piperazine-2,3-dione—N—CONHCHCONH—penicillanate Na, phenyl<br>m.p. (decomp.) 185 − 187° C, yield 86 %<br>D(−)− |
| ClCH$_2$CH$_2$—piperazine-2,3-dione—N—COCl | ClCH$_2$CH$_2$—piperazine-2,3-dione—N—CONHCHCONH—penicillanate Na, phenyl<br>m.p. (decomp.) 210° C, yield 83 %<br>D(−)− |
| CH$_3$CH$_2$—6-methylpiperazine-2,3-dione—N—COCl | CH$_3$CH$_2$—6-methylpiperazine-2,3-dione—N—CONHCHCONH—penicillanate Na, phenyl<br>m.p. (decomp.) 175 − 177° C, yield 86 %<br>D(−)− |
| CH$_3$—6-methylpiperazine-2,3-dione—N—COCl | CH$_3$—6-methylpiperazine-2,3-dione—N—CONHCHCONH—penicillanate Na, phenyl<br>m.p. (decomp.) 177 − 178° C, yield 79 % |

EXAMPLE 12

A suspension of 1.4 g of 6-[D(−)-α-aminophenylacetamido]penicillanic acid in 30 ml of tetrahydrofuran containing 20% by volume of water was adjusted to a pH of 8.0 to 8.5 by addition of triethylamine with stirring to form a solution. This solution was cooled to 0° to 5° C., and 10 ml of a tetrahydrofuran solution containing 1.2 g of 4-npentyl-2,3-dioxo-1-piperazinocarbonyl chloride was dropped into said solution. During this period, the pH of the reaction solution was maintained at 7.5 to 8.5 by gradual addition of triethylamine. Subsequently, the resulting mixed solution was reacted at said temperature for 30 minutes and then at 10° to 15° C. for 90 minutes, while maintaining the pH thereof at 7.5 to 8.5. After the reaction, the tetrahydrofuran was removed by distillation under reduced pressure, and the residue was dissolved in 20 ml of water and then washed two times with 20 ml of ethyl acetate. To the aqueous layer was further added 30 ml of ethyl acetate, and the resulting mixture was adjusted to a pH of 1.5 by addition of dilute hydrochloric acid with ice-cooling. Thereafter, the ethyl acetate layer was separated off, sufficiently washed with water, dried over magnesium sulfate, and then freed from the solvent by distillation under reduced pressure. The residue was crystallized by addition of diisopropyl ether to obtain 1.8 g of crystals of 6-[D(−)-α-(4-n-pentyl-2,3-dioxo-1-piperazinocarbonylamino)phenylacetamido]penicillanic acid, m.p. 96° C. (decomp.), yield 80.5%.

IR (KBr) cm$^{-1}$: $\nu_{C=O}$ 1770 (lactam), 1720–1660 (—CON<, —COOH)

NMR ((CD$_3$)$_2$SO + D$_2$O) τ values:
2.62 (5H), 4.31 (1H), 4.51–4.69 (2H), 6.04 (1H), 6.20–6.90 (6H), 8.50 (3H), 8.60 (3H), 8.75 (6H), 8.90 (3H)

The above-mentioned operation was repeated, except that the 4-n-pentyl-2,3-dioxo-1-piperazinocarbonyl chloride was replaced by each of the reactive derivatives of compounds of formula (III) shown in Table 14, to obtain respective objective compounds as shown in Table 14. The structure of each objective compound was confirmed by IR and NMR.

chloride, the same operation as in Example 12 was repeated to obtain 1.2 g of a sodium salt of 6-[D(−)-α-(4-methyl-2,3-dioxo-1-piperazinocarbonylamino)-p-hydroxyphenylacetamido]penicillanic acid, m.p. 170°–172° C. (decomp.), yield 75%.

IR (KBr) cm$^{-1}$: — $\nu_{C=O}$ 1760 (lactam), 1710–1660 (—CON<), 1600 (—COO$^\ominus$)

NMR ((CD$_3$)$_2$SO) τ values:
2.8–3.3 (4H), 4.45 (1H), 4.65 (2H), 6.05 (1H), 6.2 (4H), 6.97 (3H), 8.48 (3H), 8.60 (3H)

In the same manner as above, a sodium salt of 6-[D(−)-α-(4-ethyl-2,3-dioxo-1-piperazinocarbonylamino)-p-hydroxyphenylacetamido]penicillanic acid, m.p. 175° C. (decomp.), yield 72%, was obtained from 4-ethyl-2,3-dioxo-1-piperazinocarbonyl chloride and a triethylamine salt of 6-[D(−)-α-amino-p-hydroxyphenylacetamido]penicillanic acid.

EXAMPLE 14

To a solution of 0.8 g of a phthalide ester of 6-[D(−)-α-aminophenylacetamido]penicillanic acid in 10 ml of tetrahydrofuran was added 0.25 ml of triethylamine. Into the resulting mixture was dropped 0.32 g of 4-methyl-2,3-dioxo-1-piperazinocarbonyl chloride with ice-cooling, and the mixture was reacted at room temperature for 2 hours. After the reaction the solvent was removed by distillation under reduced pressure. The residue was dissolved in a mixed solvent comprising 20 ml of ethyl acetate and 20 ml of water, and the resulting solution was adjusted to a pH of 2 by addition of dilute Table 14

| Reactive derivative of compound of formula (III) | Objective compound |
|---|---|
| CH$_3$(CH$_2$)$_4$CH$_2$—N(piperazine-2,3-dione)—N—COCl | D(−)— CH$_3$(CH$_2$)$_4$CH$_2$—N(piperazine-2,3-dione)—N—CONHCHCONH—(penicillanic acid, phenyl) m.p. (decomp.) 107° C, yield 89% |
| CH$_3$(CH$_2$)$_5$CH$_2$—N(piperazine-2,3-dione)—N—COCl | D(−)— CH$_3$(CH$_2$)$_5$CH$_2$—N(piperazine-2,3-dione)—N—CONHCHCONH—(penicillanic acid, phenyl) m.p. (decomp.) 92° C, yield 88.5% |
| CH$_3$(CH$_2$)$_6$CH$_2$—N(piperazine-2,3-dione)—N—COCl | D(−)— CH$_3$(CH$_2$)$_6$CH$_2$—N(piperazine-2,3-dione)—N—CONHCHCONH—(penicillanic acid, phenyl) m.p. (decomp.) 95° C, yield 79.8% |
| CH$_3$CH$_2$—N(piperazine-2,3-dione)—N—CSCl | D(−)— CH$_3$CH$_2$—N(piperazine-2,3-dione)—N—CSNHCHCONH—(penicillanic acid, phenyl) m.p. (decomp.) 80–82° C, yield 95% |

EXAMPLE 13

Using 1.7 g of a triethylamine salt of 6-[D(−)-α-amino-p-hydroxyphenylacetamido]penicillanic acid and 0.7 g of 4-methyl-2,3-dioxo-1-piperazinocarbonyl hydrochloric acid. Subsequently, the organic layer was separated off, washed with water, washed with a 2% aqueous sodium hydrogencarbonate solution, washed with water, dried over magnesium sulfate, and then concentrated to a liquid amount of about 2 ml. To the concentrate was added 20 ml of diisopropyl ether to deposit crystals, which were then collected to obtain 0.95 g of crystals of a phthalide ester of 6-[D(−)-α-(4methyl-2,3-dioxo-1-piperazinocarbonyl)-phenylacetamido]penicillanic acid, m.p. 157°–160° C. (decomp.), yield 90.0 %.

IR (KBr) cm$^{-1}$:—$\nu_{C=O}$ 1780 (lactam, 1715 (ester), 1680 (—CON<)

NMR ((CD$_3$)$_2$CO + D$_2$O) $\tau$ values:
2.12 (4H), 2.40 (1H), 2.58 (5H), 4.25–4.60 (3H), 5.45 (1H), 5.85–6.42 (4H), 6.90 (3H), 8.50 (6H)

The above-mentioned operation was repeated except that the 4-methyl-2,3-dioxo-1-piperazinocarbonyl chloride was replaced by each of the reactive derivatives of compounds of formula (III) shown in Table 15, to obtain respective objective compounds as shown in Table 15. The structure of each objective compound was confirmed by IR and NMR.

at 7.5 to 8.0 by gradual addition of triethylamine. The resulting mixed solution was reacted for 30 minutes, while maintaining the pH thereof at 7.5 to 8.0. After completion of the reaction, the tetrahydrofuran was removed by distillation under reduced pressure. The residue was dissolved in a mixed solvent comprising 50 ml of water and 50 ml of ethyl acetate, and the resulting solution was adjusted to a pH of 1.5 by addition of dilute hydrochloric acid with ice-cooling. Subsequently, the organic layer was separated off, washed with water, dried over anhydrous magnesium sulfate, and then freed from the solvent by distillation under reduced pressure to form crystals. The thus formed crystals were washed with diethyl ether to obtain 0.9 g of a methoxymethyl ester of 6-[D(−)-α-(4-methyl-2,3-dioxo-1-piperazinocarbonylamino)phenylacetamido]penicillanic acid, m.p. 111°–115° C. (decomp.), yield 82.5%.

IR (KBr) cm$^{-1}$: — $\nu_{C=O}$ 1780 (lactam), 1740 (ester), 1700–1660 (—CON<)

NMR ((CD$_3$)$_2$CO) $\tau$ values:

Table 15

| Reactive derivative of compound of formula (III) | Objective compound |
|---|---|
| 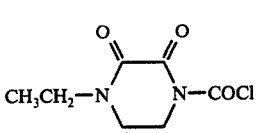 | 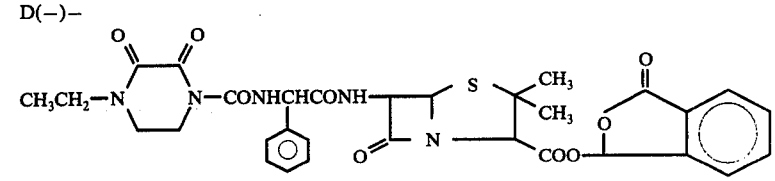<br>m.p. (decomp.) 108 – 110° C, yield 90 % |
| 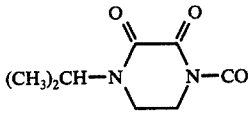 | 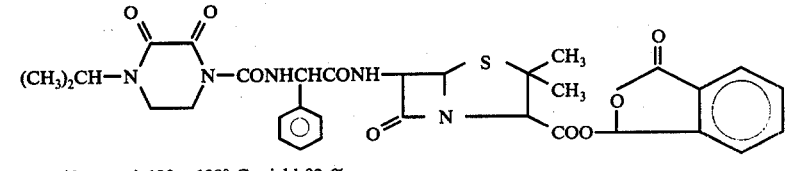<br>m.p. (decomp.) 128 – 130° C, yield 92 % |
| 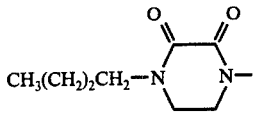 | 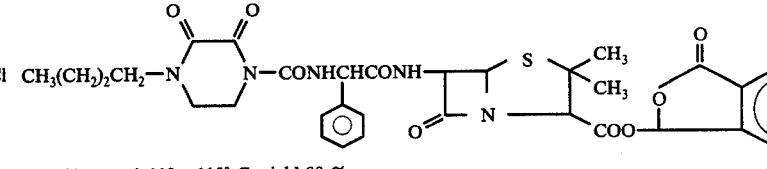<br>m.p. (decomp.) 113 – 115° C, yield 88 % |

0.15 (1H), 2.0 (1H), 2.67 (5H), 4.3–4.5 (3H), 4.75 (2H), 5.7 (1H), 6.55 (4H), 6.97 (3H), 7.25 (3H), 8.84 (3H), 8.60 (3H)

EXAMPLE 15

A solution of 0.86 g of a hydrochloride of methoxymethyl ester of 6-[D(−)-α-aminophenylacetamido]-penicillanic acid in 15 ml of tetrahydrofuran containing 20% by volume of water was adjusted to a pH of 8.0 to 8.5 by addition of triethylamine at 0° to 5° C. Into this solution, a solution of 0.38 g of 4-methyl-2,3-dioxo-1-piperazinocarbonyl chloride in 10 ml of tetrahydrofuran was dropped over a period of 10 minutes. During this period, the pH of the reaction solution was maintained The above-mentioned operation was repeated, except that the 4-methyl-2,3-dioxo-1-piperazinocarbonyl chloride was replaced by each of the reactive derivatives of compounds of formula (III) shown in Table 16, to obtain respective objective compounds as shown in Table 16. The structure of each objective compound was confirmed by IR and NMR.

Table 16

| Reactive derivative of compound of formula (III) | Objective compound |
|---|---|
| D(−)— | |

Table 16-continued

| Reactive derivative of compound of formula (III) | Objective compound |
|---|---|
| 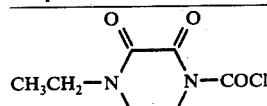 | 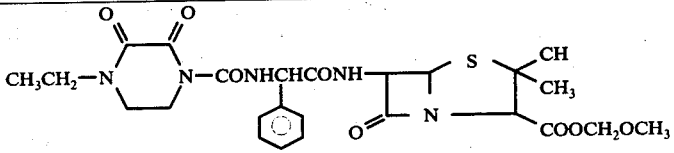 m.p. (decomp.) 83 – 85° C, yield 80.2 % |
| 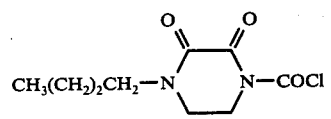 | D(−)− 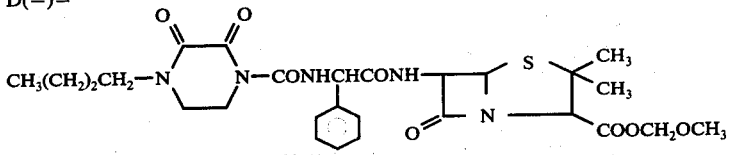 m.p. (decomp.) 78 – 80° C, yield 80 % |
| 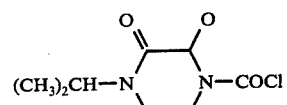 | D(−)− 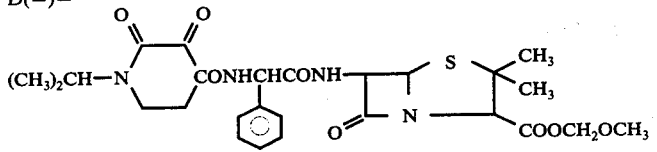 m.p. (decomp.) 93 – 95° C, yield 82.5 % |
| 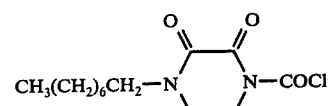 | D(−)− 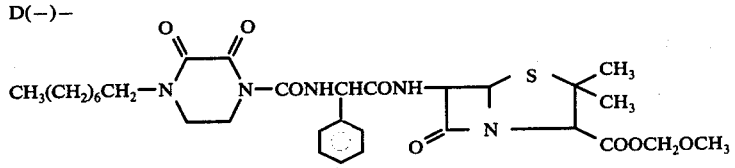 m.p. (decomp.) 70 – 74° C, yield 74.4 % |

EXAMPLE 16

Using 1.5 g of a hydrochloride of pivaloyloxymethyl ester of 6-[D(−)-α-aminophenylacetamido]-penicillanic acid and 0.6 g of 4-methyl-2,3-dioxo-1-piperazinocarbonyl chloride, the same operation as in Example 15 was repeated to obtain a pivaloyloxymethyl ester of 6-[D(−)-α-(4-methyl-2,3-dioxo-1-piperazinocarbonylamino)phenylacetamido]penicillanic acid, m.p. 108°–111° C. (decomp.). yield 75%.

IR (KBr) cm$^{-1}$: — $\nu_{C=O}$ 1780 (lactam), 1750 (ester), 1710–1660 (—CON<)

The above-mentioned operation was repeated, except that the 4-methyl-2,3-dioxo-1-piperazinocarbonyl chloride was replaced by each of the reactive derivatives of compounds of formula (III) shown in Table 17, to obtain respective objective compounds as shown in Table 17. The structure of each objective compound was confirmed by IR and NMR.

Table 17

| Reactive derivative of compound of formula (III) | Objective compound |
|---|---|
| 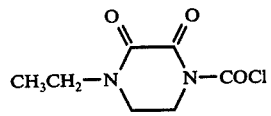 | D(−)− 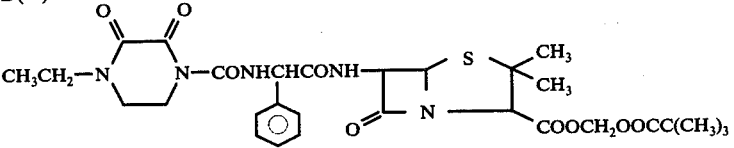 m.p. (decomp.) 94 – 98° C, yield 77 % |
| 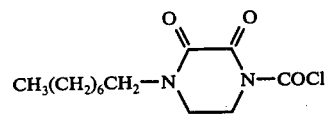 | D(−)− 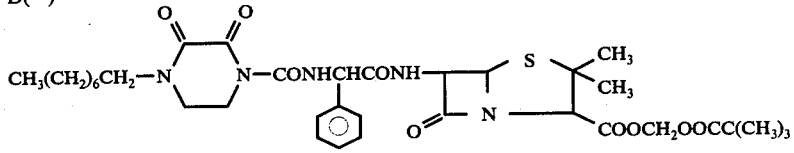 m.p. (decomp.) 72 – 75° C, yield 72 % |

EXAMPLE 17

Using 0.81 g of a hydrochloride of β-piperidinoethyl ester of 6-[D(−)-α-aminophenylacetamido]penicillanic acid and 0.3 g of 4-methyl-2,3-dioxo-1-piperazinocarbonyl chloride, the same operation as in Example 15 was repeated to obtain 0.75 g of a β-piperidinoethyl ester of 6-[D(—)-α-(4-methyl-2,3-dioxo-1-piperazinocarbonylamino)phenylacetamido]penicillanic acid, m.p. 166°–169° C. (decomp.), yield 78%.

IR (KBr) cm$^{-1}$: — $\nu_{C=O}$ 1780 (lactam), 1740 (ester), 1710–1670 (—CON<)

NMR (CDCl$_3$) τ values:
2.7 (5H), 4.3–4.6 (3H), 5.7 (1H), 5.75 (2H), 6.0 (2H), 6.4 (2H), 6.9 (3H), 7.45 (2H), 7.6 (4H), 8.5 (12H)

The above-mentioned operation was repeated, except that the 4-methyl-2,3-dioxo-1-piperazinocarbonyl chloride was replaced by 4-n-octyl-2,3-dioxo-1-piperazinocarbonyl chloride, to obtain a β-piperidinoethyl ester of 6-[D(—)-α-(4-n-octyl-2,3-dioxo-1-piperazinocarbonylamino)phenylacetamido]penicillanic acid, m.p. 110°–115° C. (decomp.), yield 73.58%.

EXAMPLE 18

Using 0.93 g of a hydrochloride of β-morpholinoethyl ester of 6-[D(—)-α-aminophenylacetamido]-penicillanic acid and 0.39 g of 4-methyl-2,3-dioxo-1-piperazinocarbonyl chloride, the same operation as in Example 15 was repeated to obtain 0.8 g of a β-morpholinoethyl ester of 6-[D(—)-α-(4-methyl-2,3-dioxo-1-piperazinocarbonylamino)phenylacetamido]-penicillanic acid, m.p. 150°–153° C. (decomp.), yield 73%.

IR (KBr) cm$^{-1}$: — $\nu_{C=O}$ 1780 (lactam), 1740 (ester), 1710–1680 (—CON<)

NMR (CDCl$_3$) τ values:
2.55 (5H), 4.3–4.55 (3H), 5.6 (1H), 5.7 (3H), 6.0 (2H), 6.3 (2H), 7.4 (2H), 7.5 (4H), 8.5 (6H)

The above-mentioned operation was repeated, except that the 4-methyl-2,3-dioxo-1-piperazinocarbonyl chloride was replaced by 4-n-octyl-2,3-dioxo-1-piperazinocarbonyl chloride, to obtain a β-morpholinoethyl ester of 6-[D(—)-α-(4-n-octyl-2,3-dioxo-1-piperazinocarbonylamino)phenylacetamido]penicillanic acid, m.p. 103°–105° C. (decomp.), yield 70%.

EXAMPLE 19

(1) — To a solution of 8.7 g of a sodium salt of D(—)-α-phenylglycine in 50 ml of water were added 50 ml of ethyl acetate and 5.05 g of triethylamine. To the resulting mixture was gradually added 9.5 g of 4-methyl-2,3-dioxo-1-piperazinocarbonyl chloride at 0° to 5° C. over a period of 15 minutes, and then the mixture was reacted at 5° to 15° C. for 30 minutes. After the reaction, the aqueous layer was separated off, washed with diethyl ether, and then adjusted to a pH of 1.5 by addition of dilute hydrochloric acid to deposit crystals. The deposited crystals were collected by filtration, washed with water and dried to obtain 14.1 g of D(—)-α-(4-methyl-2,3-dioxo-1-piperazinocarbonylamino)phenylacetic acid, m.p. 138°–141° C. (decomp.), yield 87%. Recrystallization from hydrous butanol gave white crystals, m.p. 140°–142° C. (decomp.).

Elementary analysis (for C$_{14}$H$_{15}$N$_3$O$_5$.H$_2$O): Calculated (%) C: 52.01 H: 5.30 N: 13.00 Found (%) C: 52.24 H: 5.32 N: 12.87

IR (KBr) cm$^{-1}$: — $\nu_{C=O}$ 1710, 1700, 1660

(2) — Into a solution of 10 g of the above-mentioned D(—)-α-(4-methyl-2,3-dioxo-1-piperazinocarbonylamino)phenylacetic acid in 200 ml of acetone was dropped a solution of 5.2 g of a sodium salt of 2-ethylhexonic acid in 50 ml of acetone with stirring to deposit crystals. The deposited crystals were collected by filtration and then washed with acetone to obtain 9.6 g of a sodium salt of D(—)-α-(4-methyl-2,3-dioxo-1-piperazinocarbonylamino)phenylacetic acid, m.p. 165° C. (decomp.), yield 95%.

(3) — To a suspension of 8.8 g of the abovementioned sodium salt of D(—)-α-(4-methyl-2,3-dioxo-1-piperazinocarbonylamino)phenylacetic acid in 80 ml of methylene chloride was added 20 mg of N-methylmorpholine. Into the resulting mixture was dropped a solution of 3.1 g of ethyl chlorocarbonate in 20 ml of methylene chloride at −20° to −15° C. over a period of 5 minutes, and the mixture was reacted at said temperature for 1 hour. Into this reaction liquid was dropped a solution of 9.4 g of a triethylamine salt of 6-aminopenicillanic acid in 40 ml of methylene chloride at −40° to −30° C. over a period of 10 minutes, and the resulting mixture was reacted at −40° to −20° C. over a period of 1 hour. After the reaction, the temperature of the reaction liquid was gradually elevated to 0° C. over a period of 1 hour, and the mixture was then subjected to extraction with 100 ml of water. Subsequently, the aqueous layer was separated off, and the methylene chloride layer was further subjected to extraction with 50 ml of water, and the resulting aqueous layer was combined with the aforesaid aqueous layer. The combined aqueous layer was adjusted to a pH of 2 by addition of dilute hydrochloric acid with ice-cooling to deposit crystals. The deposited crystals were collected by filtration, sufficiently washed with water, dried and then dissolved in 200 ml of acetone. Into the resulting solution was dropped a solution of 4 g of a sodium salt of 2-ethylhexanoic acid in 40 ml of acetone over a period of 10 minutes to deposit crystals. The deposited crystals were collected by filtration, washed with acetone and then dried to obtain 11.4 g of a sodium salt of 6-[D(—)-α-(4-methyl-2,3-dioxo-1-piperazinocarbonylamino)phenylacetamido]penicillanic acid, m.p. 170° C. (decomp.), yield 80.8%.

The above-mentioned operation was repeated, except that the D(—)-α-(4-methyl-2,3-dioxo-1-piperazinocarbonylamino)phenylacetic acid was replaced by each of the compounds of formula (V) shown in Table 18, to obtain respective objective compounds as shown in Table 18. The structure of each objective compound was confirmed by IR and NMR.

Table 18

| Compound of formula (V) | Objective compound |
|---|---|
| D(—)—<br>CH$_3$CH$_2$—N(piperazine-2,3-dione)N—CONHCHCOOH<br>(phenyl) | D(—)—<br>CH$_3$CH$_2$—N(piperazine-2,3-dione)N—CONHCHCONH—(β-lactam-thiazolidine)—CH$_3$, CH$_3$, COONa<br>(phenyl) |
| D(—)— | D(—)— |

Table 18-continued

| Compound of formula (V) | Objective compound |
|---|---|
| CH₃CH₂CH₂—N(piperazine-2,3-dione)N—CONHCHCOOH (phenyl) | CH₃CH₂CH₂—N(piperazine-2,3-dione)N—CONHCHCONH—(β-lactam)—S—C(CH₃)₂—COONa (phenyl) |
| D(−)− CH₃(CH₂)₂CH₂—N(piperazine-2,3-dione)N—CONHCHCOOH (phenyl) | D(−)− CH₃(CH₂)₂CH₂—N(piperazine-2,3-dione)N—CONHCHCONH—(β-lactam)—S—C(CH₃)₂—COONa (phenyl) |

EXAMPLE 20

(1) — To a solution of 2.28 g of D(−)-α-amino-1,4-cyclohexadienylacetic acid in 15 ml of N NaOH were added 20 ml of ethyl acetate and 2.1 ml of triethylamine, and the resulting mixture was cooled to 0° C. To this mixture was gradually added 1.69 g of 4-methyl-2,3-dioxo-1-piperazinocarbonyl chloride over a period of 10 minutes. Subsequently, the mixture was reacted for 30 minutes with ice-cooling, and then the aqueous layer was separated off. To the aqueous layer was further added 20 ml of ethyl acetate. The resulting mixture was adjusted to a pH of 2 by addition of 2N hydrochloric acid with ice-cooling, and the ethyl acetate layer was separated off. The organic layer was sufficiently washed with water, dried over anhydrous magnesium sulfate, freed from the solvent by distillation under reduced pressure and then incorporated with isopropyl alcohol to deposit crystals. The deposited crystals were collected by filtration to obtain 2.5 g of white crystals of D(−)-α-(4-methyl-2,3-dioxo-1-piperazinocarbonylamino)-1,4-cyclohexadienylacetic acid, m.p. 140°–145° C. (decomp.), yield 74%.

IR (KBr) cm⁻¹: — $\nu_{NH}$ 3300, $\nu_{C=O}$ 1715, 1660
NMR (d₆-DMSO) τ values:
0.57 (1H, d), 4.26 (1H, s), 4.36 (2H, s), 5.29 (1H, d), 6.07–6.18 (2H, m), 6.38–6.49 (2H, m), 7.05 (3H, s), 7.35 (4H, s)

(2) — To a suspension of 0.45 g of the above-mentioned D(−)-α-(4-methyl-2,3-dioxo-1-piperazinocarbonylamino)-1,4-cyclohexadienylacetic acid in 15 ml of anhydrous methylene chloride was added 0.24 ml of N-methylmorpholine with stirring to form a solution. After cooling the solution of −10° C., 3 ml of an anhydrous methylene chloride solution containing 0.24 g of ethyl chlorocarbonate was dropped into the solution, and the resulting mixture was reacted at said temperature for 90 minutes. Subsequently, the reaction liquid was cooled to −20° C., and 5 ml of a methylene chloride solution containing 0.70 g of a triethylamine salt of 6-aminopenicillanic acid and 0.31 ml of triethylamine was gradually dropped into the reaction liquid. The resulting mixture was reacted at −20° C. for 1 hour, at −20° to 0° C. for 1 hour, and at 0° to 5° C. for 1 hour. Thereafter, the reaction liquid was freed from the solvent by distillation under reduced pressure. The residue was dissolved in 10 ml of water and then washed with 10 ml of ethyl acetate. The aqueous layer was again incorporated with 15 ml of ethyl acetate, and then adjusted to a pH of 2.0 by addition of 2N HCl with ice-cooling. Subsequently, the ethyl acetate layer was separated off, washed with water, dried over anhydrous magnesium sulfate, and freed from the solvent by distillation under reduced pressure to obtain 0.74 g of white crystals of 6-[D(−)-α-(4-methyl-2,3-dioxo-1-piperazinocarbonylamino)-1,4-cyclohexadienylacetamido]penicillanic acid, m.p. 84°–87° C. (decomp.), yield 87%.

IR (KBr) cm⁻¹: — $\nu_{C=O}$ 1780 (lactam), 1730–1660 (—COOH, —CON<)
NMR (d₆-DMSO) τ values:
0.55 (1H, d), 0.95 (1H, d), 4.22 (1H, s), 4.35 (2H, s), 4.41–4.61 (2H, s), 4.92 (1H, d), 5.75 (1H, s), 6.05 (2H, bs), 6.40 (2H, bs), 7.03 (3H, s), 7.35 (4H, s), 8.40 (3H, s), 8.52 (3H, s)

The thus obtained product was adjusted to a pH of 7.0 by neutralization with an aqueous sodium hydrogencarbonate solution, and then subjected to filtration and freeze-drying to obtain a sodium salt thereof.

The above-mentioned operation was repeated, except that the D(−)-α-(4-methyl-2,3-dioxo-1-piperazinocarbonylamino)-1,4-cyclohexadienylacetic acid was replaced by each of the compounds of formula (V) shown in Table 19, to obtain respective objective compounds as shown in Table 19. The structure of each objective compound was confirmed by IR and NMR.

Table 19

| Compound of formula (V) | Objective compound |
|---|---|
| D(−)− CH₃CH₂—N(piperazine-2,3-dione)N—CONHCHCOOH (phenyl) | D(−)− CH₃CH₂—N(piperazine-2,3-dione)N—CONHCHCONH—(β-lactam)—S—C(CH₃)₂—COONa (phenyl) |
| D(−)− | D(−)− |

Table 19-continued

| Compound of formula (V) | Objective compound |
|---|---|
| 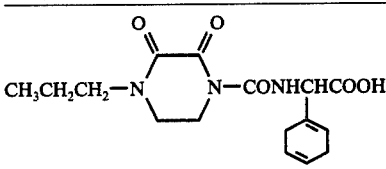 | 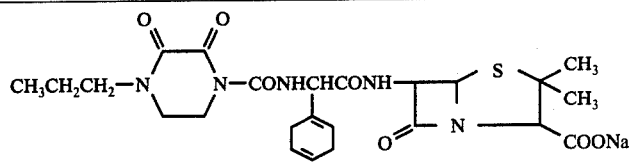 |
| D(−)− 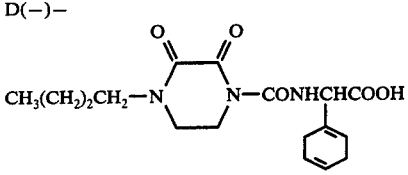 | D(−)− 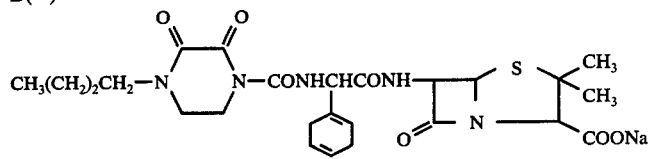 |

EXAMPLE 21

(1) — To a solution of 2.2 g of DL-α-amino-2-thienylacetic acid in 14 ml of a N sodium hydroxide solution was added at 0° C. 2.2 g of triethylamine. To the resulting mixture was further added 3.6 g of 4-methyl-2,3-dioxo-1-piperazinocarbonyl chloride incrementally at said temperature. Subsequently, the mixture was reacted at 0° C. for 30 minutes, and then at room temperature for 30 minutes. After the reaction, the reaction liquid was adjusted to a pH of 1.0 by addition of dilute hydrochloric acid to deposit crystals, the deposited crystals were collected by filtration, washed with water and then dried to obtain 3.5 g of DL-α-(4-methyl-2,3-dioxo-1-piperazinocarbonylamino)-2-thienylacetic acid, m.p. 214°–215° C. (decomp.), yield 80.5%.

IR (KBr) cm$^{-1}$: — $\nu_{C=O}$ 1710, 1680–1660

(2) — Into a solution of 3.5 g of the abovementioned DL-α-(4-methyl-2,3-dioxo-1-piperazinocarbonylamino)-2-thienylacetic acid in 100 ml of acetone was dropped a solution of 1.86 g of a sodium salt of 2-ethylhexanoic acid in 50 ml of acetone, upon which crystals were deposited. The deposited crystals were collected by filtration and then washed with acetone to obtain 3.5 g of a sodium salt of DL-α-(4-methyl-2,3-dioxo-1-piperazinocarbonylamino)-2-thienylacetic acid, m.p. 175°–176° C. (decomp.).

(3) — To a suspension of 3.3 g of the abovementioned sodium salt of DL-α-(4-methyl-2,3-dioxo-1-piperazinocarbonylamino)-2-thienylacetic acid in 50 ml of methylene chloride was added 30 mg of N-methylmorpholine, and the resulting mixture was then cooled to −20° to −15° C. Into the resulting mixture was dropped a solution of 1.3 g of ethyl chlorocarbonate in 20 ml of methylene chloride over a period of 5 minutes, and the mixture was stirred at said temperature for 90 minutes. Subsequently, a solution of 3.3 g of a triethylamine salt of 6-aminopenicillanic acid in 50 ml of methylene chloride was dropped into the mixture at −50° to −40° C. over a period of 20 minutes, and the resulting mixture was reacted with stirring at −40° to −30° C. for 30 minutes, at −30° to −20° C. for 30 minutes, and then at −20° to 0° C. for 30 minutes. After the reaction, the solvent was removed by distillation under reduced pressure, and the residue was dissolved in water. The resulting aqueous solution was adjusted to a pH of 2.0 by addition of dilute hydrochloric acid with ice-cooling to deposit crystals. The deposited crystals were collected by filtration, sufficiently washed with water and then dried to obtain 4.1 g of 6-[DL-α-(4-methyl-2,3-dioxo-1-piperazinocarbonylamino)-2-thienylacetamido]penicillanic acid, m.p. 185° C. (decomp.), yield 80.5%.

IR (nujol) cm$^{-1}$: — $\nu_{C=O}$ 1780 (lactam), 1715 (—COOH), 1685–1675 (—CON<)

NMR ((CD$_3$)$_2$CO) τ values:
0.5 (1H), 1.8 (1H), 2.6 (1H), 2.85–3.05 (2H), 4.0 (1H), 4.2–4.5 (2H), 5.7 (1H), 5.8–6.0 (2H), 6.2–6.4 (2H), 6.95 (3H), 8.4 (3H), 8.45 (3H)

The thus obtained product was adjusted to a pH of 7.0 by neutralization with an aqueous sodium hydrogencarbonate solution, and then subjected to filtration and freeze-drying to obtain a sodium salt thereof.

The above-mentioned operation was repeated, except that the sodium salt of DL-α-(4-methyl-2,3-dioxo-1-piperazinocarbonylamino)-2-thienylacetic acid was replaced by each of the compounds of formula (V) shown in Table 20, to obtain respective objective compounds as shown in Table 20. The structure of each objective compound was confirmed by IR and NMR.

Table 20

| Compound of formula (V) | Objective compound |
|---|---|
| DL− 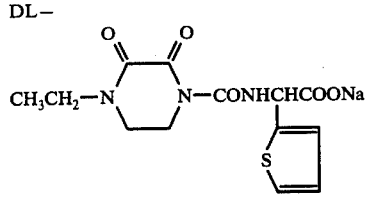 | DL− 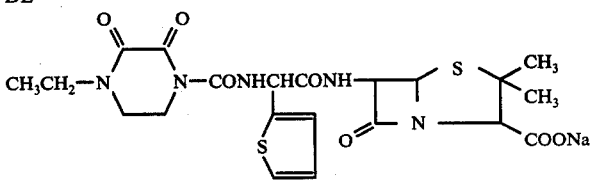 |
| DL−  | DL−  |

Table 20-continued

| Compound of formula (V) | Objective compound |
|---|---|
| CH₃CH₂CH₂—N(piperazine-2,3-dione)—CONHCH(2-thienyl)COONa | CH₃CH₂CH₂—N(piperazine-2,3-dione)—CONHCH(2-thienyl)CONH—(penicillin)—COONa |
| DL— CH₃(CH₂)₂CH₂—N(piperazine-2,3-dione)—CONHCH(2-thienyl)COONa | DL— CH₃(CH₂)₂CH₂—N(piperazine-2,3-dione)—CONHCH(2-thienyl)CONH—(penicillin)—COONa |

EXAMPLE 22

To a suspension of 0.9 g of 6-[D(—)-α-aminophenylacetamido]penicillanic acid in 30 ml of anhydrous ethyl acetate were added at 5° to 10° C. 0.55 g of triethylamine and 0.6 g of trimethylsilyl chloride. The resulting mixture was reacted at 15° to 20° C. for 3 hours to form trimethylsilylated 6-[D(—)-α-aminophenylacetamido]penicillanic acid. To this acid was then added 1 g of 4-ethyl-2,3-dioxo-1-piperazinocarbonyl chloride, and the resulting mixture was reacted at 15° to 20° C. for 2 hours. After the reaction, a deposited triethylamine hydrochloride was separated by filtration, and the filtrate was mixed with 0.4 g of n-butanol to deposit crystals. The deposited crystals were collected by filtration to obtain 1.25 g of white crystals of 6-[D(—)-α-(4-ethyl-2,3-dioxo-1-piperazinocarbonylamino)phenylacetamido]penicillanic acid. Into a solution of said crystals in 30 ml of tetrahydrofuran was dropped a solution of 0.38 g of a sodium salt of 2-ethylhexanoic acid in 10 ml of tetrahydrofuran, upon which white crystals were deposited. The deposited crystals were collected by filtration, sufficiently washed with tetrahydrofuran and then dried to obtain 1.25 g of a sodium salt of 6-[D(—)-α-(4-ethyl-2,3-dioxo-1-piperazinocarbonylamino)phenylacetamido]penicillanic acid, m.p. 183°–185° C. (decomp.), yield 90%.

EXAMPLE 23

To a suspension of 4 g of a trihydrate of 6-[D(—)-α-aminophenylacetamido]penicillanic acid in 40 ml of water was added 20 ml of ethyl acetate, and the resulting mixture was cooled to 2° C. Subsequently, the mixture was mixed with 1.37 g of potassium carbonate, and then stirred at 2° to 3° C. for 2 minutes. Thereafter, 1.89 g of 4-methyl-2,3-dioxo-1-piperazinocarbonyl chloride was added to the mixture at said temperature over a period of 10 minutes, and the resulting mixture was reacted at said temperature for 15 minutes. After the reaction, slight amounts of insolubles were separated by filtration, and the filtrate was charged into 80 ml of ethyl acetate. Into the resulting mixture was dropped 5 ml of 2N HCl at 20° to 22° C. over a period of 5 minutes, and the mixture was stirred at said temperature for 5 hours to deposit crystals. The deposited crystals were collected by filtration, washed two times with 4 ml of water, further washed two times with 4 ml of isopropanol, and then dried to obtain 4.0 g of a dihydrate of 6-[D(—)-α-(4-methyl-2,3-dioxo-1-piperazinocarbonylamino)phenylacetamido]penicillanic acid, m.p. 156°–157° C. (decomp.), yield 75.4%.

IR (KBr) cm⁻¹: — $\nu_{C=O}$ 1775, 1740, 1695, 1670
NMR (d₆-DMSO) τ values:
0.18 (1H, d), 0.77 (1H, d), 2.66 (5H, s), 4.30 (1H, d), 4.40 (3H, br), 4.48 (1H, g), 4.65 (1H, d), 5.80 (1H, s), 6.12 (2H, bs), 6.45 (2H, bs), 7.06 (3H, s), 8.48 (3H, s), 8.60 (3H, s)

The above-mentioned operation was repeated, except that the 4-methyl-2,3-dioxo-1-piperazinocarbonyl chloride was replaced by 4-ethyl-2,3-dioxo-1-piperazinocarbonyl chloride, to obtain a monohydrate of 6-[D(—)-α-(4-ethyl-2,3-dioxo-1-piperazinocarbonylamino)phenylacetamido]penicillanic acid, m.p. 154°–156° C. (decomp.), yield 84.8%.

IR (KBr) cm⁻¹: — $\nu_{C=O}$ 1775, 1735, 1705, 1680, 1665
NMR (d₆-DMSO) τ values:
0.20 (1H, d), 0.76 (1H, d), 2.69 (5H, s), 4.32 (1H, d), 4.53 (1H, q), 4.64 (1H, d), 5.00 (3H, br), 5.83 (1H, s), 6.13 (2H, bs), 6.49 (2H, bs), 6.62 (2H, q), 8.44 (3H, s), 8.58 (3H, s), 8.91 (3H, t)

The thus obtained monohydrate was neutralized with an aqueous sodium hydrogencarbonate solution, and then subjected to filtration and freeze-drying to obtain a sodium salt of 6-[D(—)-α-(4-ethyl-2,3-dioxo-1-piperazinocarbonylamino)phenylacetamido]-penicillanic acid.

Further, a solution in 10 ml of nitromethane of 2 g of the aforesaid dihydrate of 6-[D(—)-α-(4-methyl-2,3-dioxo-1-piperazinocarbonylamino)phenylacetamido]-penicillanic acid was allowed to stand overnight to deposit crystals, which were then collected by filtration to obtain 2 g of a monohydrate of a nitromethane addition product of 6-[D(—)-α-(4-methyl-2,3-dioxo-1-piperazinocarbonylamino)phenylacetamido]penicillanic acid, m.p. 128°–130° C. (decomp.), yield 92.2%.

Elementary analysis (for C₂₂H₂₅N₅O₇S.CH₃NO₂.-H₂O): Calculated (%) C: 47.42 H: 5.19 N: 14.43 Found (%) C: 47.94 H: 5.13 N: 14.53

IR (KBr) cm⁻¹: — $\nu_{C=O}$ 1770, 1735, 1700, 1680
NMR (d₆-DMSO) τ values:
0.22 (1H, d), 0.80 (1H, d), 2.69 (5H, s), 3.30 (3H, br), 4.30 (1H, d), 4.46–4.70 (2H), 5.67 (3H, s), 5.81 (1H, s), 6.13 (2H, bs), 6.46 (2H, bs), 7.07 (3H, s), 8.45 (3H, s), 8.58 (3H, s)

EXAMPLE 24

To a suspension of 1.6 g of a trihydrate of D(—)-α-aminobenzyl penicillin in 20 ml of water was added at 2° to 3° C. 0.54 g of potassium carbonate, and the resulting mixture was stirred for 3 minutes. To the mixture was gradually added 0.81 g of 4-ethyl-2,3-dioxo-1-piperazinocarbonyl chloride at said temperature over a period of 10 minutes, and the mixture was reacted for 15 minutes. After the reaction, slight amounts of insolubles formed were separated by filtration, and the filtrate was charged into 10 ml of methyl n-propyl ketone. Into the resulting mixture was dropped 1.98 ml of 2N HCl at 15° to 20° C. over a period of 2 minutes, and the mixture was stirred at said temperature for 1 hour to deposit crystals. The deposited crystals were collected by filtration, washed two times with 2 ml of water, further washed two times with 2 ml of methyl n-propyl ketone, and then dried to obtain 1.7 g of a monohydrate of D(−)-α-(4-ethyl-2,3-dioxo-1-piperazinocarbonylamino)benzylpenicillin, m.p. 152°–154° C. (decomp.), yield 80.2%.

The thus obtained product was neutralized with an aqueous sodium hydrogencarbonate solution, and then subjected to filtration and freeze-drying to obtain a sodium salt of the said product.

ous layer was separated off. The thus obtained aqueous layer was washed with 30 ml of ethyl acetate, cooled to 0° to 5° C., and then adjusted to a pH of 1.5 by addition of dilute hydrochloric acid to deposit white crystals. The deposited crystals were collected by filtration, sufficiently washed with water and then dried to obtain 4.7 g of white crystals of 7-[D(−)-α-(4-methyl-2,3-dioxo-1-piperazinocarbonylamino)-phenylacetamido]-3-methyl-$\Delta^3$-cephem-4-carboxylic acid, m.p. 185°–186° C. (decomp.), yield 86%.

IR (KBr) cm$^{-1}$: — $\nu_{C=O}$ 1770–1760 (lactam), 1720–1660 (—CON<, —COOH)

NMR (d$_6$-DMSO) τ values:
0.1 (1H, d), 0.56 (1H, d), 2.62 (5H, s), 4.26–4.37 (2H, dd), 5.05 (1H, d), 6.1 (2H, bs), 6.47 (2H, bs), 6.63 (2H, s), 7.05 (3H, s), 8.02 (3H, s)

The above-mentioned operation was repeated, except that the 4-methyl-2,3-dioxo-1-piperazinocarbonyl chloride was replaced by each of the reactive derivatives of compounds of formula (III) shown in Table 21, to obtain respective objective compounds as shown in Table 21. The structure of each objective compound was confirmed by IR and NMR.

Table 21

| Reactive derivative of compound of formula (III) | Objective commpound |
|---|---|
| CH$_3$CH$_2$—N(piperazine-2,3-dione)—COCl | D(−)— CH$_3$CH$_2$—N(piperazine-2,3-dione)—CONHCHCONH—(phenyl)—cephem-S-CH$_3$-COOH m.p. (decomp.) 168° C, yield 80 % |
| CH$_3$CH$_2$CH$_2$—N(piperazine-2,3-dione)—COCl | D(−)— CH$_3$CH$_2$CH$_2$—N(piperazine-2,3-dione)—CONHCHCONH—(phenyl)—cephem-S-CH$_3$-COOH m.p. (decomp.) 160° C, yield 80.5 % |
| CH$_3$(CH$_2$)$_2$CH$_2$—N(piperazine-2,3-dione)—COCl | CH$_3$(CH$_2$)$_2$CH$_2$—N(piperazine-2,3-dione)—CONHCHCONH—(phenyl)—cephem-S-CH$_3$-COOH m.p. (decomp.) 150° C, yield 76 % |

EXAMPLE 25

A suspension of 4.0 g of a monohydrate of 7-[D(−)-α-aminophenylacetamido]-3-methyl-$\Delta^3$-cephem-4-carboxylic acid in 60 ml of tetrahydrofuran containing 20% by volume of water was adjusted to a pH of 8.0 to 8.5 by gradual addition of triethylamine with stirring to form a solution, which was then cooled to 0° C. To this solution were gradually added 2.5 g of crystals of 4-methyl-2,3-dioxo-1-piperazinocarbonyl chloride over a period of 10 minutes. During this period, the pH of the reaction solution was maintained at 7.5 to 8.0 by gradual addition of triethylamine. Subsequently, the resulting mixture was reacted at 0° to 5° C. for 15 minutes while maintaining the pH thereof at 7.5 to 8.0. After the reaction, the reaction liquid was stirred together with 60 ml of diethyl ether and 70 ml of water, and then the aque-

EXAMPLE 26

(1) — To a solution of 0.92 g of 1-n-pentyl-2,3-dioxopiperazine in 15 ml of anhydrous dioxane were added 1.1 ml of triethylamine and 1.08 g of trimethylsilyl chloride. The resulting mixture was stirred at room temperature for 20 hours to form triethylamine hydrochloride. This hydrochloride was separated by filtration, and the filtrate was dropped at 0° to 5° C. into a solution of 0.6 g of phosgene in 10 ml of anhydrous tetrahydrofuran. Subsequently, the resulting mixture was reacted at 5° to 10° C. for 30 minutes and then at room temperature for 2 hours. Thereafter, the solvent was removed by distillation under reduced pressure to obtain 1.21 g of pale yellow, oily 4-n-pentyl-2,3-dioxo-1-piperazinocarbonyl chloride.

IR (film) cm$^{-1}$: — $v_{C=O}$ 1790, 1720–1665

(2) — A suspension of 1.70 g of a monohydrate of 7-[D(−)-α-aminophenylacetamido]-3-methyl-Δ$^3$-cephem-4-carboxylic acid in 50 ml of tetrahydrofuran containing 20% by volume of water was adjusted to a pH of 8.0 to 8.5 by addition of triethylamine with stirring to form a solution. This solution was cooled to 0° to 5° C., and 7 ml of an anhydrous tetrahydrofuran solution containing 1.21 g of the 4-n-pentyl-2,3-dioxo-1-piperazinocarbonyl chloride obtained in (1) was dropped into the solution. During this period, the pH of the solution was maintained at a pH of 7.5 to 8.0 by addition of triethylamine. Subsequently, the resulting mixed solution was reacted at 0° to 5° C. for 1 hour and then at 5° to 10° C. for 2 hours while maintaining the pH thereof at 7.5 to 8.0. After the reaction, the tetrahydrofuran was removed by distillation under reduced pressure, and the residue was dissolved in 20 ml of water and then washed two times with 20 ml of ethyl acetate. The aqueous layer was again charged with 40 ml of ethyl acetate, and then adjusted to a pH of 1.5 by gradual addition of dilute hydrochloric acid with ice-cooling. Subsequently, the ethyl acetate layer was separated off, washed with water, and then dried over anhydrous magnesium sulfate. Thereafter, 10 ml of an ethyl acetate solution containing 0.75 g of sodium 2-ethylhexanoate was dropped into the layer at 0° to 5° C. to deposit white crystals. The deposited crystals were collected by filtration, and washed with ethyl acetate and then with diethyl ether to obtain 1.95 g of a sodium salt of 7-[D(−)-α-(4-n-pentyl-2,3-dioxo-1-piperazinocarbonylamino)phenylacetamido]-3-methyl-Δ$^3$-cephem-4-carboxylic acid, m.p. 164°–166° C. (decomp.), yield 75%.

IR (KBr) cm$^{-1}$: — $v_{C=O}$ 1750 (lactam), 1720–1660 (—CON<), 1590 (—COO$^\ominus$)

NMR (d$_6$-DMSO + D$_2$O) $\tau$ values:
2.58 (5H, s), 4.33 (1H, s), 4.49 (1H, d), 5.17 (1H, d), 6.10 (2H, bs), 6.42–6.87 (6H, m), 8.09 (3H, s), 8.60–8.90 (6H, bs), 9.12 (3H, t)

The above-mentioned operation was repeated, except that the 4-n-pentyl-2,3-dioxo-1-piperazinocarbonyl chloride was replaced by each of the reactive derivatives of compounds of formula (III) shown in Table 22, to obtain respective objective compounds as shown in Table 22. The structure of each objective compound was confirmed by IR and NMR.

Table 22

| Reactive derivative of compound of formula (III) | Objective compound |
|---|---|
| 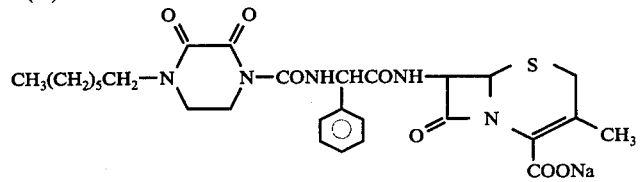 | | m.p. (decomp.) 160° C, yield 77.7 %

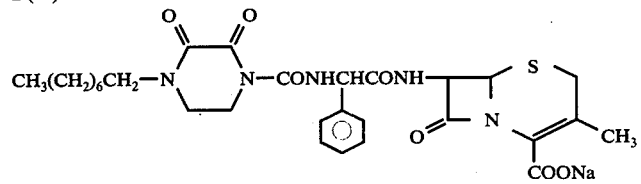

m.p. (decomp.) 158° C, yield 78 %

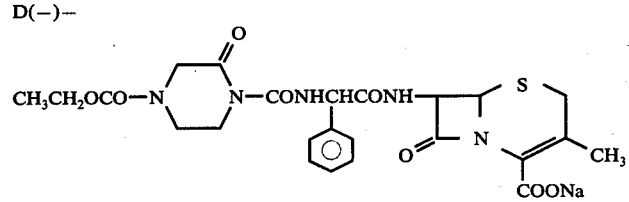

m.p. (decomp.) 154° C, yield 78 % m.p. (decomp.) 185 – 188° C, yield 77 %

Table 22-continued

| Reactive derivative of compound of formula (III) | Objective compound |
|---|---|
| 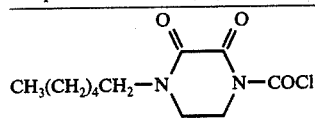 | 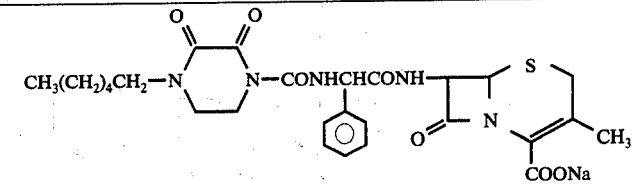 |
| | m.p. (decomp.) 135 – 137° C, yield 79.2 % |

EXAMPLE 27

Using 1.5 g of a hydrochloride of methoxymethyl ester of 7-[D(—)-α-aminophenylacetamido]-3-methyl-Δ³-cephem-4-carboxylic acid and 0.65 g of 4-methyl-2,3-dioxo-1-piperazinocarbonyl chloride, the same operation as in Example 25 repeated to obtain 1.6 g of a methoxymethyl ester of 7-[D(— )-α-(4-methyl-2,3-dioxo-1-piperazinocarbonylamino)phenylacetamido]-3-methyl-Δ³-cephem-4-carboxylic acid, m.p. 146°–148° C. (decomp.), yield 86%.

IR (KBr) cm$^{-1}$: — $\nu_{C=O}$ 1770 (lactam), 1710 (ester), 1680–1600 (—CON<)

EXAMPLE 28

To a suspension of 0.20 g of 7-[D(—)-α-aminophenylacetamido]-3-acetoxymethyl-Δ³-cephem-4-carboxylic acid in 15 ml of anhydrous chloroform was added 0.17 ml of triethylamine with stirring to form a solution, which was then cooled to 0° C. To this solution was added 0.11 g of 4-methyl-2,3-dioxo-1-piperazinocarbonyl chloride, and the resulting mixture was reacted at room temperature for 2 hours. After the reaction, the reaction liquid was evaporated under reduced pressure, and the residue was dissolved in 15 ml of water. The resulting solution was washed with 10 ml of ethyl acetate. The aqueous layer was again charged with 20 ml of ethyl acetate, and then adjusted to a pH of 1.5 by addition of 2N hydrochloric acid with ice-cooling. Subsequently, the ethyl acetate layer was separated off, successively washed with water and a saturated aqueous sodium chloride solution, and then dried over magnesium sulfate. Thereafter, the solvent was removed by distillation under reduced pressure to obtain 0.22 g of white crystals of 7-[D(—)-α-(4-methyl-2,3-dioxo-1-piperazinocarbonylamino)phenylacetamido]-3-acetoxymethyl-Δ³-cephem-4-carboxylic acid, m.p. 175° C. (decomp.), yield 76%.

IR (KBr) cm$^{-1}$: — $\nu_{C=O}$ 1770 (lactam), 1720–1650 (—CON<, —COOH)

NMR (d$_6$-DMSO) τ values:
0.23 (1H, d), 0.63 (1H, d), 2.66 (5H, s), 4.32 (1H, q), 4.43 (1H, d), 5.05 (1H, d), 5.21 (2H, q), 6.15 (2H, bs), 6.40 (2H, bs), 6.57 (2H, bs), 7.0 (3H, s), 8.0 (3H, s)

The above-mentioned operation was repeated, except that the 4-methyl-2,3-dioxo-1-piperazinocarbonyl chloride was replaced by each of the reactive derivatives of compounds of formula (III) shown in Table 23, to obtain respective objective compounds as shown in Table 23. The structure of each objective compound was confirmed by IR and NMR.

Table 23

| Reactive derivative of compound of formula (III) | Objective compound |
|---|---|
| 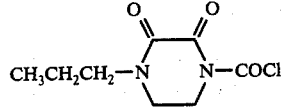 | 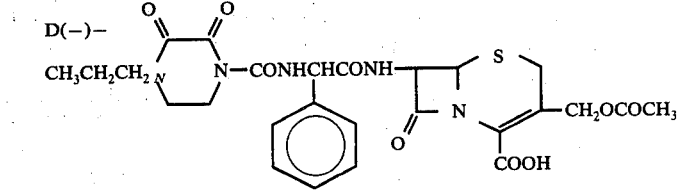 |
| | m.p. (decomp.) 150° C, yield 83.4 % |
| 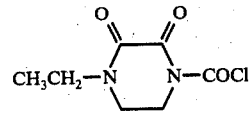 | 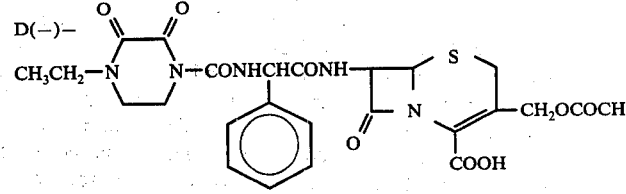 |
| | m.p. (decomp.) 165° C, yield 83 % |
| 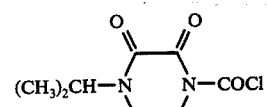 | 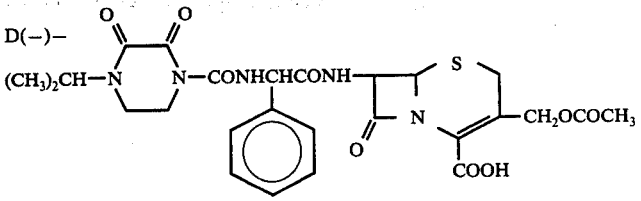 |
| | m.p. (decomp.) 146° C, yield 82 % |

Table 23-continued

| Reactive derivative of compound of formula (III) | Objective compound |
|---|---|
| 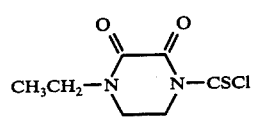 | 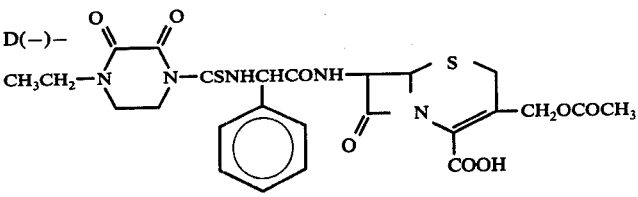<br>m.p. (decomp.) 112° C, yield 95 % |
| 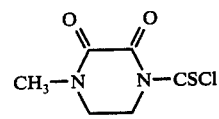 | 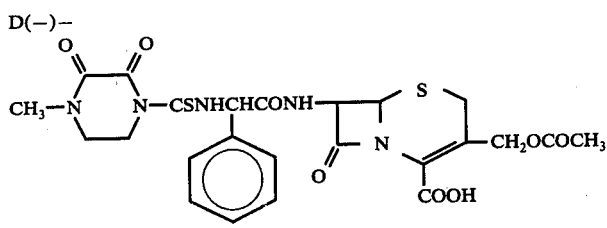<br>m.p. (decomp.) 134° C, yield 90.2 % |

The aforesaid 7-[D(−)-α-(4-methyl-2,3-dioxo-1-piperazinocarbonylamino)phenylacetamido]-3-acetoxymethyl-Δ³-cephem-4-carboxylic acid, m.p. 175° C. (decomp.), was recrystallized from hydrous acetone to obtain white crystals showing a melting point of 198° to 200° C. (decomp.)

EXAMPLE 29

(1) — To a solution of 28.2 g of a sodium salt of D(−)-phenylglycine in 150 ml of water were added 200 ml of ethyl acetate and 18.2 g of triethylamine, and the resulting mixture was cooled to 0° C. To this mixture was added 34.3 g of 4-methyl-2,3-dioxo-1-piperazinocarbonyl chloride over a period of 15 minutes, and the mixture was reacted at 5° to 10° C. for 15 minutes. Thereafter, the aqueous layer was separated off and adjusted to a pH of 0.5 by addition of 2N hydrochloric acid with ice-cooling to deposit crystals. The deposited crystals were collected by filtration and then dried to obtain 42 g of white crystals of D(−)-α-(4-methyl-2,3-dioxo-1-piperazinocarbonylamino)phenylacetic acid, m.p. 195° C. (decomp.).

IR (KBr) cm⁻¹: — $\nu_{C=O}$ 1700, 1600
NMR (d₆-DMSO) τ values:
0.1 (1H, d), 2.65 (5H, s), 4.60 (1H, d), 6.10 (2H, bs), 6.50 (2H, bs), 7.0 (3H, s)

(2) — To a suspension in 15 ml of anhydrous methylene chloride of 0.31 g of the D(−)-α-(4-methyl-2,3-dioxo-1-piperazinocarbonylamino)phenylacetic acid obtained in the above-mentioned item (1) was added 0.11 g of N-methylmorpholine with stirring to form a solution, which was then cooled to −20° C. To this solution was added 3 ml of an anhydrous methylene chloride solution containing 0.13 g of ethyl chlorocarbonate, and the resulting mixture was reacted at −10° to 20° C. for 60 minutes to form a mixed acid anhydride. Into the thus formed acid anhydride was dropped a solution formed by adding 0.50 ml of triethylamine to a suspension in 5 ml of methanol of 0.41 g of 7-amino-3-[2-(5-methyl-1,3,4-thiadiazolyl)-thiomethyl]-Δ³-cephem-4-carboxylic acid. After the dropping, the resulting mixture was reacted at −50° to −30° C. for 30 minutes, at −30° to −20° C. for 30 minutes, at −20° to 0° C. for 60 minutes, and then at room temperature for 30 minutes. Thereafter, the reaction liquid was concentrated under reduced pressure, and the concentrate was dissolved in 10 ml of water, washed with 5 ml of ethyl acetate, again charged with 15 ml of ethyl acetate, and then adjusted to a pH of 1.5 by addition of 2N hydrochloric acid with ice-cooling. Subsequently, insolubles were separated by filtration, and the ethyl acetate layer was separated off, successively washed with water and a saturated sodium chloride solution, dried over magnesium sulfate, and then freed from the solvent by distillation under reduced pressure to obtain 0.58 g of pale yellow crystals of 7-[D(−)-α-(4-methyl-2,3-dioxo-1-piperazinocarbonylamino)phenylacetamido]-3-[2-(5-methyl-1,3,4-thiadiazolyl)-thiomethyl]-Δ³-cephem-4-carboxylic acid, m.p. 160° C. (decomp.), yield 91%.

IR (KBr) cm⁻¹: — $\nu_{C=O}$ 1780 (lactam), 1650–1720 (—CON<, —COOH)
NMR (d₆-DMSO) τ values:
0.2 (1H, d), 0.6 (1H, d), 2.60 (5H, s), 4.35 (1H, q), 4.40 (1H, d), 5.0 (1H, d), 5.70 (2H, q), 6.10 (2H, bs), 6.25–6.55 (2H, 2H, bs), 7.0 (3H, s), 7.30 (3H, s)

The above-mentioned operation was repeated, except that the D(−)-α-(4-methyl-2,3-dioxo-1-piperazinocarbonylamino)phenylacetic acid was replaced by each of the compounds of formula (V) shown in Table 24, to obtain respective objective compounds as shown in Table 24. The structure of each objective compound was confirmed by IR and NMR.

Table 24
| Compound of formula (V) | Objective compound |
|---|---|
| D(−)− 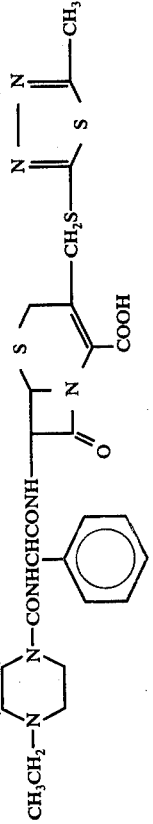 | D(−)− 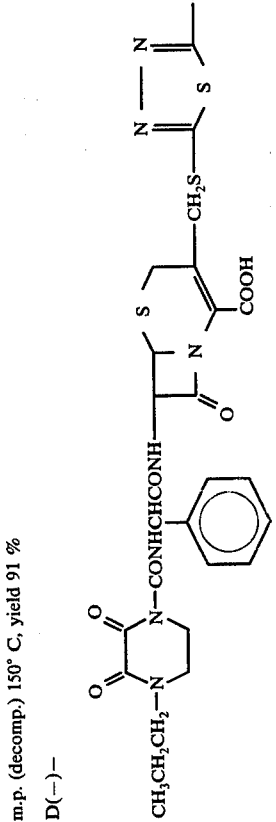<br>m.p. (decomp.) 150° C, yield 91 % |
| D(−)− 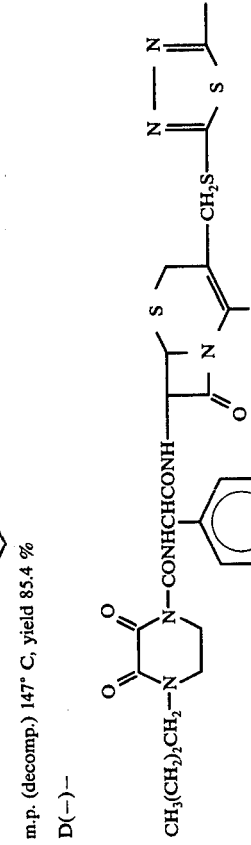 | D(−)− 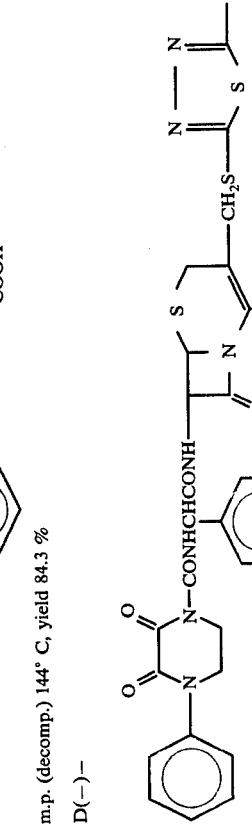<br>m.p. (decomp.) 147° C, yield 85.4 % |
| D(−)−  | D(−)− 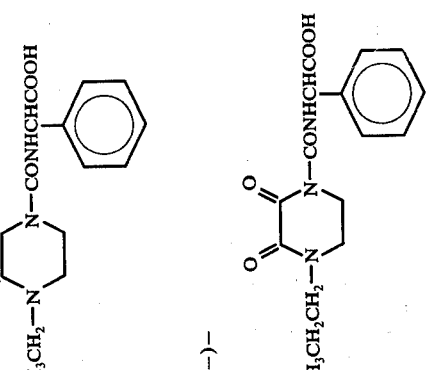<br>m.p. (decomp.) 144° C, yield 84.3 % |
| D(−)− 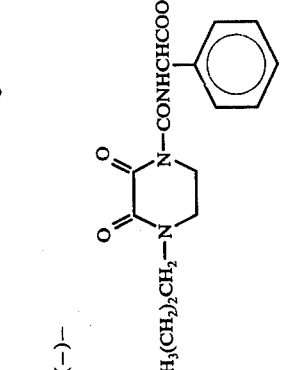 | D(−)− 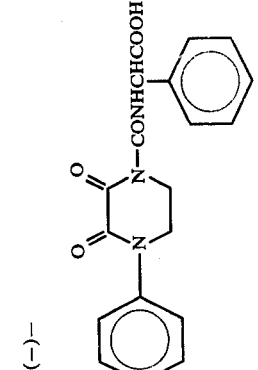<br>m.p. (decomp.) 167° C, yield 93 % |

EXAMPLE 30

Using 0.3 g of D(—)-α-(4-methyl-2,3-dioxo-1-piperazinocarbonylamino)phenylacetic acid and 0.33 g of 7-amino-3-[5-(1-methyl-1,2,3,4-tetrazolyl)-thiomethyl]-Δ³-cephem-4-carboxylic acid, the same operation as in Example 29 was repeated, to obtain 0.5 g of 7-[D(—)-α-(4-methyl-2,3-dioxo-1-piperazinocarbonylamino)phenylacetamido]-3-[5-(1-methyl-1,2,3,4-tetrazolyl)-thiomethyl]-Δ³-cephem-4-carboxylic acid, m.p. 161°–163° C. (decomp.), yield 76%.

IR (nujol) cm⁻¹: — $\nu_{C=O}$ 1775 (lactam), 1720–1660 (—CON<, —COOH)

NMR (d₆-DMSO) τ values:
0.02 (1H, d), 0.34 (1H, d), 2.48 (5H, s), 4.17 (1H, q), 4.26 (1H, d), 4.92 (1H, d), 5.66 (2H, s), 6.01 (5H, s), 6.35 (4H, s), 7.0 (3H, s)

The above-mentioned operation was repeated, except that the D(—)-α-(4-methyl-2,3-dioxo-1-piperazinocarbonylamino)phenylacetic acid was replaced by each of the compounds of formula (V) shown in Table 25, to obtain respective objective compounds as shown in Table 25. The structure of each objective compound was confirmed by IR and NMR.

Δ³-cephem-4-carboxylic acid, m.p. 158°–159° C. (decomp.), yield 71.5%.

IR (nujol) cm⁻¹: — $\nu_{C=O}$ 1775 (lactam), 1720–1660 (—CON<, —COOH)

The above-mentioned operation was repeated, except that the D(—)-α-(4-methyl-2,3-dioxo-1-piperazinocarbonylamino)phenylacetic acid was replaced by D(—)-α-(4-ethyl-2,3-dioxo-1-piperazinocarbonylamino)phenylacetic acid, to obtain 7-[D(—)-α-(4-ethyl-2,3-dioxo-1-piperazinocarbonylamino)phenylacetamido]-3-[5-(1,3,4-thiadiazolyl)-thiomethyl]-Δ³-cephem-4-carboxylic acid, m.p. 123° C. (decomp.), yield 64.5%.

EXAMPLE 32

Using 0.31 g of D(—)-α-(4-methyl-2,3-dioxo-1-piperazinocarbonylamino)phenylacetic acid and 0.39 g of 7-amino-3-[2-(1-methyl-1,3,4-triazolyl)-thiomethyl]-Δ³-cephem-4-carboxylic acid, the same operation as in Example 29 was repeated, except that the methanol was replaced by anhydrous methylene chloride, to obtain 0.43 g of 7-[D(—)-α-(4-methyl-2,3-dioxo-1-piperazinocarbonylamino)phenylacetamido]-3-[2-(1-methyl-1,3,4-triazolyl)-thiomethyl]-Δ³-cephem-4-carboxylic acid, yield 70%.

Table 25

| Compound of formula (V) | Objective compound |
|---|---|
| D(—)— 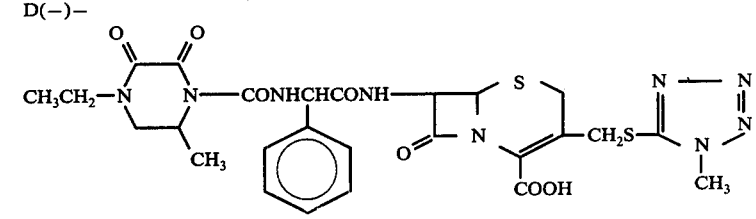 | D(—)— <br> m.p. (decomp.) 170° C, yield 63.6 % * |
| D(—)— 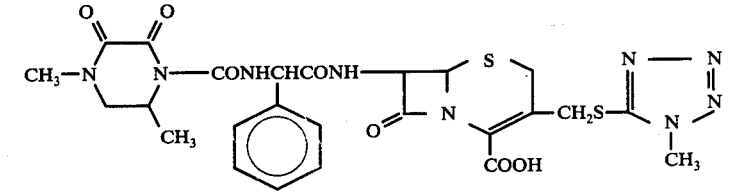 | D(—)— <br> m.p. (decomp.) 173° C, yield 68 % |
| D(—)— 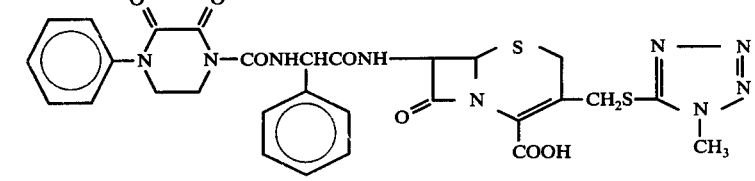 | D(—)— <br> m.p. (decomp.) 163° C, yield 74.8 % |

* Anhydrous methylene chloride was substituted for the methanol used in Example 29.

EXAMPLE 31

Using 0.30 g of D(—)-α-(4-methyl-2,3-dioxo-1-piperazinocarbonylamino)phenylacetic acid and 0.34 g of 7-amino-3-[5-(1,3,4-thiadiazolyl)-thiomethyl]-Δ³-cephem-4-carboxylic acid, the same operation as in Example 29 was repeated, to obtain 0.47 g of 7-[D(—)-α-(4-methyl-2,3-dioxo-1-piperazinocarbonylamino)-phenylacetamido]-3-[5-(1,3,4-thiadiazolyl)-thiomethyl]-

IR (nujol) cm⁻¹: — $\nu_{C=O}$ 1780 (lactam), 1720–1650 (—CON<, —COOH)

The above-mentioned operation was repeated, except that the D(—)-α-(4-methyl-2,3-dioxo-1-piperazinocarbonylamino)phenylacetic acid was replaced by each of the compounds of formula (V) shown in Table 26, to obtain respective objective compounds as shown in Table 26. The structure of each objective compound was confirmed by IR and NMR.

bonylamino)phenylacetic acid was replaced by each of the compounds of formula (V) shown in Table 27, to Table 26

| Compound of formula (V) | Objective compound |
|---|---|
| D(−)− ethyl-dioxopiperazine-CONHCHCOOH with phenyl | D(−)− same with cephalosporin-thiadiazole-methyl; m.p. (decomp.) 147° C, yield 68.5 % |
| D(−)− phenyl-dioxopiperazine-CONHCHCOOH with phenyl | D(−)− same with cephalosporin-thiadiazole-methyl; m.p. (decomp.) 158° C, yield 74.5 % |

EXAMPLE 33

The procedure of Example 29 was repeated, except that the D(−)-α-(4-methyl-2,3-dioxo-1-piperazinocarbonylamino)phenylacetic acid was replaced by each of the compounds of formula (V) shown in Table 27, to obtain respective objective compounds shown in Table 27. The structure of each objective compound was confirmed by IR and NMR.

Table 27

| Compound of formula (V) | Objective compound |
|---|---|
| D(−)− CH₃CO−N(oxopiperazine)−CONHCHCOOH−phenyl | D(−)− same with cephalosporin-thiadiazole-CH₃ |
| D(−)− CH₃SO₂−N(oxopiperazine)−CONHCHCOOH−phenyl | D(−)− same with cephalosporin-thiadiazole-CH₃ |
| D(−)− CH₃−N(oxopiperazine)−CONHCHCOOH−phenyl | D(−)− same with cephalosporin-thiadiazole-CH₃ |
| D(−)− CH₃CH₂−N(oxopiperazine)−CONHCHCOOH−phenyl | D(−)− same with cephalosporin-thiadiazole-CH₃ |
| D(−)− | D(−)− |

Table 27-continued

| Compound of formula (V) | Objective compound |
|---|---|
| CH₃CONHCO—N(piperazinone)—CONHCHCOOH(phenyl) | CH₃CONHCO—N(piperazinone)—CONHCHCONH—(β-lactam-S-CH₂-thiadiazole-CH₃)(phenyl) |
| D(−)− CH₃—N(piperazinone)—CONHCHCOOH(phenyl) | D(−)− CH₃—N(piperazinone)—CONHCHCONH—(β-lactam-S-CH₂-thiadiazole-CH₃)(phenyl) |
| D(−)− CH₃CH₂—N(piperazinone)—CONHCHCOOH(phenyl) | D(−)− CH₃CH₂—N(piperazinone)—CONHCHCONH—(β-lactam-S-CH₂-thiadiazole-CH₃)(phenyl) |
| D(−)− HN(dioxopiperazine)—CONHCHCOOH(phenyl) | D(−)− HN(dioxopiperazine)—CONHCHCONH—(β-lactam-S-CH₂-thiadiazole-CH₃)(phenyl) |
| D(−)− CH₃CO—N(dioxopiperazine)—CONHCHCOOH(phenyl) | D(−)− CH₃CO—N(dioxopiperazine)—CONHCHCONH—(β-lactam-S-CH₂-thiadiazole-CH₃)(phenyl) |

EXAMPLE 34

The procedure of Example 30 was repeated, except that the D(−)-α-(4-methyl-2,3-dioxo-1-piperazinocarbonylamino)phenylacetic acid was replaced by each of the compounds of formula (V) shown in Table 28, to obtain respective objective compounds shown in Table 28. The structure of each objective compound was confirmed by IR and NMR.

Table 28

| Compound of formula (V) | Objective compound |
|---|---|
| D(−)− CH₃CO—N(piperazinone)—CONHCHCOOH(phenyl) | C(−)− CH₃CO—N(piperazinone)—CONHCHCONH—(β-lactam-S-CH₂-tetrazole-N-CH₃)(phenyl) |
| D(−)− CH₃SO₂—N(piperazinone)—CONHCHCOOH(phenyl) | D(−)− CH₃SO₂—N(piperazinone)—CONHCHCONH—(β-lactam-S-CH₂-tetrazole-N-CH₃)(phenyl) |
| D(−)− | D(−)− |

Table 28-continued

| Compound of formula (V) | Objective compound |
|---|---|
| [structure: CH₃-N(piperazinone)-CONHCHCOOH with phenyl] | [structure: same acyl + cephem with tetrazolylthiomethyl, N-CH₃] |
| D(−)− [CH₃CH₂-N(piperazinone)-CONHCHCOOH, phenyl] | D(−)− [same acyl + cephem-tetrazole] |
| D(−)− [CH₃CONHCO-N(piperazinone)-CONHCHCOOH, phenyl] | D(−)− [same acyl + cephem-tetrazole] |
| D(−)− [CH₃-N(3-oxopiperazine)-CONHCHCOOH, phenyl] | D(−)− [same acyl + cephem-tetrazole] |
| D(−)− [CH₃CH₂-N(3-oxopiperazine)-CONHCHCOOH, phenyl] | D(−)− [same acyl + cephem-tetrazole] |
| D(−)− [HN(2,6-dioxopiperazine)-CONHCHCOOH, phenyl] | D(−)− [same acyl + cephem-tetrazole] |
| D(−)− [CH₃CO-N(2,6-dioxopiperazine)-CONHCHCOOH, phenyl] | D(−)− [same acyl + cephem-tetrazole] |

EXAMPLE 35

(1) — To a suspension of 0.9 g of D(−)-α-alanine in 15 ml of water was added 2.05 g of triethylamine to dissolve D(−)-α-alanine in water, and the resulting solution was cooled to 0° C. To the solution was added 2.3 g of 4-methyl-2,3-dioxo-1-piperazinocarbonyl chloride over 15 minutes, after which reaction was effected for 30 minutes with ice-cooling. Dilute hydrochloric acid was then added to the reaction product to adjust the pH thereof to 2.0. The water was removed by distillation under reduced pressure, and 30 ml of acetone was added to the residue, after which insolubles were filtered off. To the resulting acetone solution was added 10 ml of an acetone solution of 1.6 g of a sodium salt of 2-ethylhexanoic acid, and the deposited crystals were collected by filtration, and dried to obtain 2.1 g of a sodium salt of D(—)-α-(4-methyl-2,3-dioxo-1-piperazinocarbonylamino)-propionic acid having a melting point of 115°-8° C. (decomp.), yield 78.5%.

IR (KBr) cm$^{-1}$: $\nu_{C=O}$ 1700, 1680, 1600 (—CON<, —COO$^{\ominus}$)

(2) — In the same manner as in Example 32, 7-[D(—)-α-(4-methyl-2,3-dioxo-1-piperazinocarbonylamino)propionamido]-3-acetoxymethyl-Δ$^3$-cephem-4-carboxylic acid was obtained from a sodium salt of D(—)-α-(4-methyl-2,3-dioxo-1-piperazinocarbonylamino)propionic acid and 7-amino-3-acetoxymethyl-Δ$^3$-cephem-4-carboxylic acid. The thus obtained product was dissolved in 20 ml of acetone, and a solution of 0.65 g of a sodium salt of 2-ethylhexanoic acid in 5 ml of acetone was added to the resulting solution. The deposited crystals were collected by filtration and dried to obtain 1.2 g of sodium salt of 7-[D(—)-α-(4-methyl-2,3-dioxo-1-piperazinocarbonylamino)propionamido]-3-acetoxymethyl-Δ$^3$-cephem-4-carboxylic acid having a melting point of 195° C. (decomp.), yield 67.7%.

IR (KBr) cm$^{-1}$: $\nu C=O$ 1780 (lactam), 1710-1660 (—CON<), 1600 (—COO$^{\ominus}$)

EXAMPLE 36

In the same manner as in Example 32, 7-[D(—)-α-(4-methyl-2,3-dioxo-1-piperazinocarbonylamino)-p-hydroxyphenylacetamido]-3-[5-(1-methyl-1,2,3,4-tetrazolyl)-thiomethyl]-Δ$^3$-cephem-4-carboxylic acid was obtained from 7-amino-3-[5-(1-methyl-1,2,3,4-tetrazolyl)-thiomethyl]-Δ$^3$-cephem-4-carboxylic acid and D(—)-α-(4-methyl-2,3-dioxo-1-piperazinocarbonylamino)-p-hydroxyphenylacetic acid.

Melting point (decomp.), 147-9° C.; yield, 62.0%

IR (KBr) cm$^{-1}$: $\nu C=O$ 1765 (lactam), 1720-1660 (—CON<, —COOH)

In the same manner as above, 7-[D(—)-α-(4-ethyl-2,3-dioxo-1-piperazinocarbonylamino)-p-hydroxyphenylacetamido]-3-[5-(1-methyl-1,2,3,4-tetrazolyl)thiomethyl]-Δ$^3$-cephem-4-carboxylic acid, yield 80.7%, was obtained from 7-amino-3-[5-(1-methyl-1,2,3,4-tetrazolyl)thiomethyl]-Δ$^3$-cephem-4-carboxylic acid and D(—)-α-(4-ethyl-2,3-dioxo-1-piperazinocarbonylamino)-p-hydroxyphenylacetic acid.

The product obtained by recrystallization of the above obtained product from acetonitrile-water (4:7 volume ratio) decomposed at 170°-171° C. and melted at 188°-190° C. to result in a dark brown tar.

EXAMPLE 37

In the same manner as in Example 29, 7-[D(—)-α-(4-methyl-2,3-dioxo-1-piperazinocarbonylamino)-phenylacetamido]-3-azidomethyl-Δ$^3$-cephem-4-carboxylic acid was obtained from D(—)-α-(4-methyl-2,3-dioxo-1-piperazinocarbonylamino)phenylacetic acid and 7-amino-3-azidomethyl-Δ$^3$-cephem-4-carboxylic acid.

Melting point (decomp.), 185°-8° C.; yield, 68.0%

IR (KBr) cm$^{-1}$: $\nu C=O$ 1775 (lactam), 1720-1660 (—CON<, —COOH) $\nu N_3$ 2090

EXAMPLE 38

In 10 ml of a phosphoric acid buffer solution of a pH of 6.3 was suspended 0.57 g of 7-[D(—)-α-(4-ethyl-2,3-dioxo-1-piperazinocarbonylamino)phenylacetamido]-3-acetoxymethyl-Δ$^3$-cephem-4-carboxylic acid, and 0.07 g of sodium hydrogencarbonate was dissolved therein. To the solution was then added 0.12 g of 1-methyl-5-mercapto-1,2,3,4-tetrazole to dissolve the latter in the former, and the solution was subjected to reaction for 24 hours while maintaining the pH of the solution at 6.5-6.7 by using dilute hydrochloric acid and sodium hydrogencarbonate. After the reaction, the reaction liquid was cooled, and then adjusted to a pH of 5.0 by adding dilute hydrochloric acid. The reaction liquid was sufficiently washed with ethyl acetate, after which the aqueous layer was separated off and then adjusted to a pH of 1.5 by adding dilute hydrochloric acid thereto. The deposited crystals were collected by filtration and dried, after which the dried crystals were washed with ethyl acetate to obtain 0.40 g of 7-[D(—)-α-(4-ethyl-2,3-dioxo-1-piperazinocarbonylamino)phenylacetamido]-3-[5-(1-methyl-1,2,3,4-tetrazolyl)thiomethyl]-Δ$^3$-cephem-4-carboxylic acid, m.p. 163°-165° C. (decomp.), yield 74.5%.

IR (KBr) cm$^{-1}$: $\nu C=O$ 1775 (lactam), 1720-1660 (—CON<, —COOH)

NMR (d$_6$-DMSO) τ values: 0.18 (1H, $d$), 0.55 (1H, $d$), 2.64 (5H, $s$), 4.3 (1H, $q$), 4.4 (1H, $d$), 5.0 (1H, $d$), 5.75 (2H, $s$), 6.05 (5H, $s$), 6.3-6.8 (6H), 8.92 (3H, $t$)

In the same manner as above, the objective compounds shown in Table 29 were obtained from 7-[D(—)-α-(4-methyl-2,3-dioxo-1-piperazinocarbonyl)-phenylacetamido]-3-acetoxymethyl-Δ$^3$-cephem-4-carboxylic acid or 7-[D(—)-α-(4-ethyl-2,3-dioxo-1-piperazinocarbonylamino)phenylacetamido]-3-acetoxymethyl-Δ$^3$-cephem-4-carboxylic acid and the compounds of formula (VII) shown in Table 29. All the objective compounds were D(—) isomers, and the structure of each objective compound was confirmed by IR and NMR.

Table 29

| Compound of formula (VII) | Objective compound |
|---|---|
| [structure: 1-methyl-1,2,3,4-tetrazole-5-thiol] | [structure of cephem product] m.p. (decomp.) 168-170° C, yield 83 % |

Table 29-continued

| Compound of formula (VII) | Objective compound |
|---|---|
| 5-methyl-2-mercapto-1,3,4-thiadiazole | (structure with ethyl-piperazinedione, phenyl, β-lactam, $CH_2S$-(5-methyl-1,3,4-thiadiazol-2-yl)) m.p. (decomp.) 150° C, yield 73.4 % |
| 2-mercapto-1,3,4-thiadiazole | (structure with methyl-piperazinedione, phenyl, β-lactam, $CH_2S$-(1,3,4-thiadiazol-2-yl)) m.p. (decomp.) 158–159° C, yield 78.5 % |
| 3-mercapto-1,2,4-triazole | (structure with methyl-piperazinedione, phenyl, β-lactam, $CH_2S$-(1,2,4-triazol-3-yl)) m.p. (decomp.) 175–180° C, yield 73.4 % |
| 5-mercaptotetrazole | (structure with methyl-piperazinedione, phenyl, β-lactam, $CH_2S$-tetrazolyl) m.p. (decomp.) 163–165° C, yield 72.5 % |
| 5-mercaptotetrazole | (structure with ethyl-piperazinedione, phenyl, β-lactam, $CH_2S$-tetrazolyl) m.p. (decomp.) 159–160° C, yield 66 % |
| 5-methyl-2-mercapto-1,3,4-oxadiazole | (structure with methyl-piperazinedione, phenyl, β-lactam, $CH_2S$-(5-methyl-1,3,4-oxadiazol-2-yl)) m.p. (decomp.) 128–129° C, yield 67.7 % |
| 3-mercapto-2-methyl-6-oxo-1,2,4-triazine | (structure with methyl-piperazinedione, phenyl, β-lactam, $CH_2S$-(2-methyl-6-oxo-1,2,4-triazin-3-yl)) m.p. (decomp.) 95–98° C, yield 66.6 % |

Table 29-continued
| Compound of formula (VII) | Objective compound |
|---|---|
| 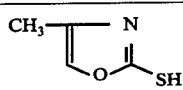 | 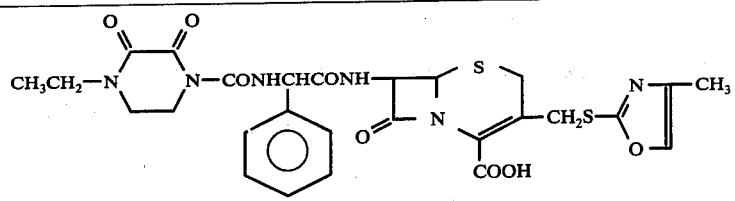<br>m.p. (decomp.) 175–180° C, yield 78.0 % |
| 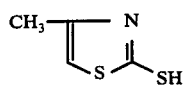 | 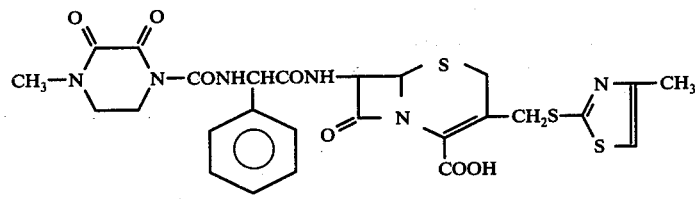<br>m.p. (decomp.) 156–157° C, yield 67.0 % |
| 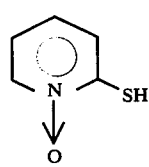 | 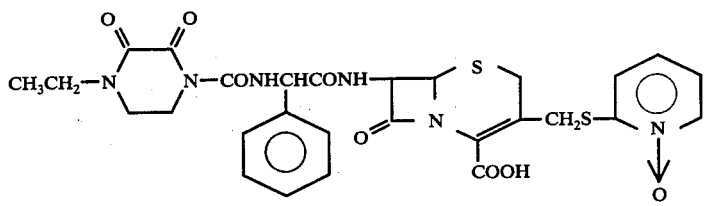<br>m.p. (decomp.) 177–180° C, yield 70.3 % |
| 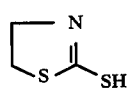 | 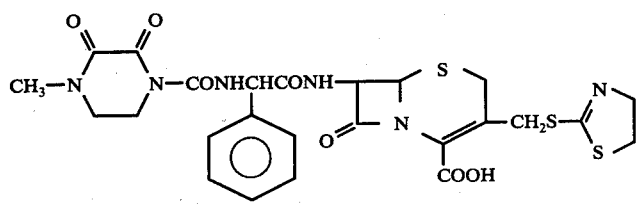<br>m.p. (decomp.) 180–182° C, yield 68.7 % |
| 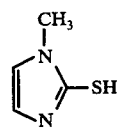 | 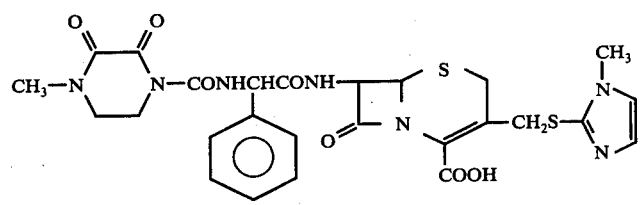<br>m.p. (decomp.) 182–184° C, yield 68 % |
| 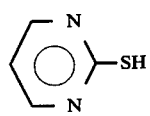 | 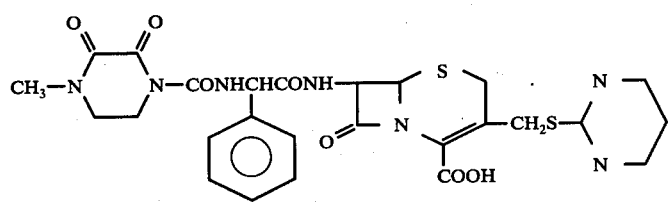<br>m.p. (decomp.) 192–194° C, yield 72.3 % |
| 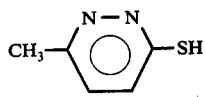 | 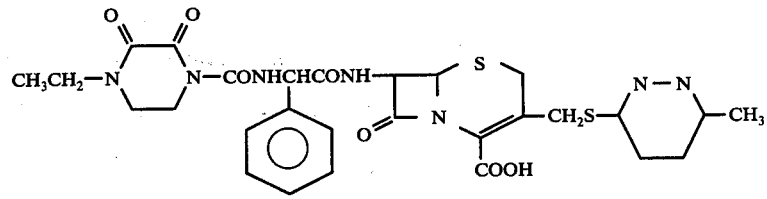<br>m.p. (decomp.) 175–178° C, yield 63.0 % |

Table 29-continued

| Compound of formula (VII) | Objective compound |
|---|---|
| NaN₃ | 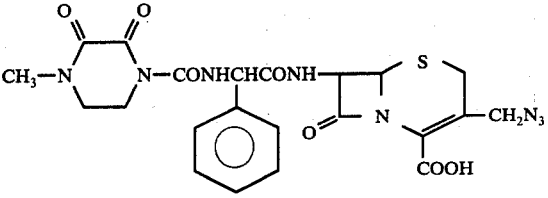 m.p. (decomp.) 185–188° C, yield 78 % |
| CH₃—N(piperazine)N—C(=S)—SNa | m.p. (decomp.) 189° C, yield 64.6 % |
| (4-methylisoxazol-5-yl)—C(=O)—SNa | m.p. (decomp.) 183° C, yield 69.1 % |
| CH₃CH₂OC(=S)—SNa | 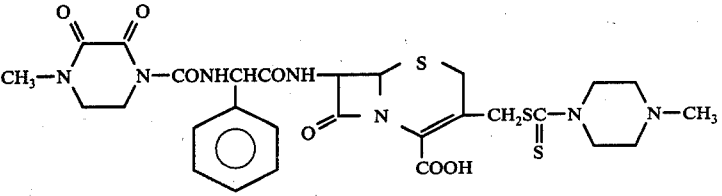 m.p. (decomp.) 181–183° C, yield 64.3 % |

EXAMPLE 39

In 10 ml of water was suspended 1.15 g of 7-[D(—)-α-(4-ethyl-2,3-dioxo-1-piperazinocarbonylamino)-phenylacetamido]-3-acetoxymethyl-Δ³-cephem-4-carboxylic acid, and 0.17 g of sodium hydrogencarbonate was then dissolved therein, after which 0.48 g of pyridine and 4.1 g of potassium thiocyanate were added thereto. The resulting mixture was subjected to reaction at 60° C. for 5 hours while maintaining the pH of the mixture at 6.0 to 6.5 by adding dilute hydrochloric acid or sodium hydrogencarbonate. After the reaction, 20 ml of water was added to dilute the reaction mixture, which was then sufficiently washed with chloroform. The aqueous layer was then separated off and then adjusted to a pH of 1.5 by adding dilute hydrochloric acid. The deposited crystals were collected by filtration, dried, and then washed with acetone to obtain 1.04 g (yield, 79.6%) of a thiocyanic acid salt of 7-[D(—)-α-(4-ethyl-2,3-dioxo-1-piperazinocarbonylamino)-phenylacetamido]-3-pyridinomethyl-Δ³-cephem-4-carboxylic acid betaine having a melting point (decomp.) of 155°–160° C., said product having the formula,

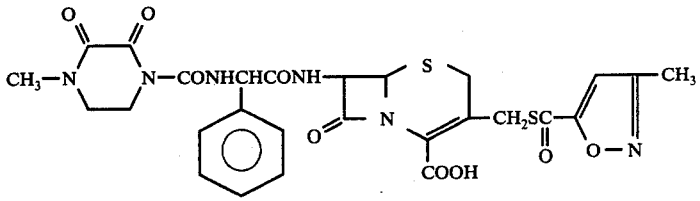

IR (KBr) cm⁻¹: νC=O 1780 (lactam), 1720–1660 (—CON<) νSCN 2040

In the same manner as above, a thiocyanic acid salt of 7-[D(—)-α-(4-methyl-2,3-dioxo-1-piperazinocarbonylamino)phenylacetamido]-3-pyridinomethyl-Δ³-cephem-4-carboxylic acid betaine was obtained from 7-[D(—)-α-(4-methyl-2,3-dioxo-1-piperazinocarbonylamino)phenylacetamido]-3-acetoxymethyl-Δ³-cephem-4-carboxylic acid and pyridine, said product having the formula,

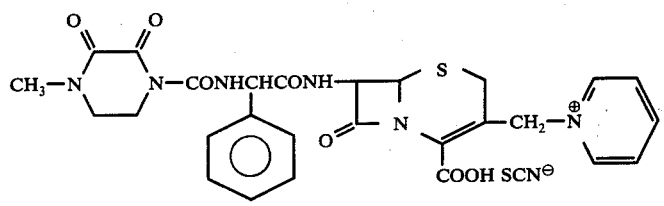

Melting point (decomp.), 180°–185° C.; yield, 82.0%

In a conventional manner, the above two products were treated with an ion exchange resin to obtain the desired 7-[D(−)-α-(4-ethyl-2,3-dioxo-1-piperazinocarbonylamino)phenylacetamido]-3-pyridinomethyl-Δ³-cephem-4-carboxylic acid betaine and 7-[D(−)-α-(4-methyl-2,3-dioxo-1-piperazinocarbonylamino)-phenylacetamido]-3-pyridinomethyl-Δ³-cephem-4-carboxylic acid betaine.

EXAMPLE 40

In 85 ml of anhydrous methanol was dissolved 1.5 g of a sodium salt of 7-[D(−)-α-(4-ethyl-2,3-dioxo-1-piperazinocarbonylamino)phenylacetamido]-3-[2-(pyridyl-1-oxide)thiomethyl]-Δ³-cephem-4-carboxylic acid. To the resulting solution was added 0.65 g of anhydrous cupric chloride, and the resulting mixture was stirred at room temperature for 15 minutes and then subjected to reaction at 50° C. for 14 hours. After the reaction, hydrogen sulfide gas was passed through the reaction solution with ice-cooling for 20 minutes. The resulting insolubles were filtered off, and the filtrate was concentrated under reduced pressure. To the residue was added 20 ml of a 5% aqueous sodium hydrogencarbonate solution, and the insolubles were filtered off, after which dilute hydrochloric acid was added to the filtrate to adjust the pH to 6.5. The filtrate was then washed with 10-ml portions of ethyl acetate three times, after which the aqueous layer was separated off and then adjusted to a pH of 1.8 by adding dilute hydrochloric acid thereto. The thus deposited crystals were collected by filtration and then dried under reduced pressure and washed with 20 ml of an ethyl acetate-chloroform mixed solvent (1:1 by volume) to obtain 0.40 g of 7-[D(−)-α-(4-ethyl-2,3-dioxo-1-piperazinocarbonylamino)phenylacetamido]-3-methoxymethyl-Δ³-cephem-4-carboxylic acid, m.p. 162°–6° C. (decomp.), yield 30.5%.

IR (KBr) cm⁻¹: νC=O 1770 (lactam), 1700 (—COOH), 1666 (—CON<)

NMR (d₆-DMSO) τ values: 0.13 (1H, d), 0.53 (1H, d), 2.61 (5H, s), 4.31 (1H, q), 4.41 (1H, d), 4.96 (1H, d), 5.82 (2H, s), 6.10 (2H, bs), 6.33 (2H, 2H, 2H, bs), 6.79 (3H, s), 8.89 (3H, t)

EXAMPLE 41

To a solution of 3.2 g of D(−)-α-(4-ethyl-2,3-dioxo-1-piperazinocarbonylamino)phenylacetic acid in 20 ml of anhydrous methylene chloride and 5 ml of dimethylformamide was added 1.33 g of N,N-dimethylaniline. The resulting mixture was cooled to −15° to −10° C., and a solution of 1.14 g of ethyl chlorocarbonate in 5 ml of anhydrous methylene chloride was dropped into said mixture over a period of 5 minutes. The mixture was reacted at said temperature for 60 minutes.

On the other hand, to a suspension of 3.28 g of 7-amino-3-[5-(1-methyl-1,2,3,4-tetrazolyl)thiomethyl]-Δ³-cephem-4-carboxylic acid in 65 ml of anhydrous acetonitrile was added 3.04 g of N,O-bis(trimethylsilyl)acetamide to obtain a solution. The solution was cooled to −20° C. and poured into the aforesaid reaction mixture. Subsequently, the mixture was reacted at −10° C. to −5° C. for 60 minutes, and at 5° to 10° C. for 60 minutes. After the reaction, to the reaction mixture 5 ml of methanol was added and the mixture was freed from insolubles by filtration. Thereafter the solvent was removed by distillation under reduced pressure. The residue was dissolved in a mixed solvent comprising 100 ml of water and 50 ml of ethyl acetate, and the resulting solution was adjusted to a pH of 7.5 to 8.0 by addition of sodium hydrogencarbonate, after which the aqueous layer was added 80 ml of ethyl acetate and 20 ml of acetone, and the resulting solution was adjusted to a pH of 1.5 by addition of dilute hydrochloric acid. Subsequently, the organic layer was separated off, sufficiently washed with water and then the solvent was removed from ethyl acetate layer by distillation under reduced pressure. The residue was dissolved in 15 ml of acetone, and to this solution was added 60 ml of 2-propanol with stirring to deposit white crystals. The deposited crystals were collected by filtration, sufficiently washed with 2-propanol and then dried to obtain 5.26 g of 7-[D(−)-α-(4-ethyl-2,3-dioxo-1-piperazinocarbonylamino)-phenylacetamido]-3-[5-(1-methyl-1,2,3,4-tetrazolyl)thiomethyl]-Δ³-cephem-4-carboxylic acid, m.p. 163°–165° C. (decomp.), yield 83.6%. The structure of this compound was confirmed by IR and NMR.

The above-mentioned operation was repeated except that the sodium salt of D(−)-α-(4-ethyl-2,3-dioxo-1-piperazinocarbonylamino)phenylacetic acid was replaced by each of the reactive derivatives of compounds of formula (III) shown in Table 30, to obtain the respective objective compounds as shown in Table 30. The structure of each objective compound was confirmed by IR and NMR.

Table 30

| Reactive derivative of compound of formula (III) | Objective compound |
|---|---|
| D(−)— | D(−)— |

Table 30-continued

| Reactive derivative of compound of formula (III) | Objective compound |
|---|---|
| (structure: CH₃N-piperazine-2,3-dione-NCONHCHCOOH with phenyl) | (structure with cephem, S, N-N tetrazole-CH₃) m.p. (decomp.) 161–163° C, yield 85.8 % |
| D(−)− (structure: CH₃CH₂N-piperazine-2,3-dione-NCONHCHCOOH with p-hydroxyphenyl) | D(−)− (structure with cephem, S, tetrazole-CH₃) m.p. (decomp.) 170–171° C (from acetonitrile-water), yield 68 % |
| D(−)− (structure: CH₃(CH₂)₂CH₂N-piperazine-2,3-dione-NCONHCHCOOH with phenyl) | D(−)− (structure with cephem, S, tetrazole-CH₃) m.p. (decomp.) 162–165° C, yield 74.0 % |
| D(−)− (structure: CH₃(CH₂)₆CH₂N-piperazine-2,3-dione-NCONHCHCOOH with phenyl) | D(−)− (structure with cephem, S, tetrazole-CH₃) m.p. (decomp.) 124–128° C, yield 75.3 % |

EXAMPLE 42

Using 3.1 g of D(−)-α-α-(4-ethyl-2,3-dioxo-1-piperazinocarbonylamino)phenylacetic acid and 3.0 g of 7-amino-3-[5-(1,2,3-triazolyl)thiomethyl]-Δ³-cephem-4-carboxylic acid, the same operation as in Example 41 was repeated to obtain 4.5 g of 7-[D(−)-α-(4-ethyl-2,3-dioxo-1-piperazinocarbonylamino)phenylacetamido]-3-[5-(1,2,3-triazolyl)thiomethyl]-Δ³-cephem-4-carboxylic acid, m.p. 177°–180° C. (decomp.), yield 76.7%.

IR (KBr) cm$^{-1}$: $\nu$C=O 1770 (lactam), 1703 (—COOH), 1680, 1667 (—CON<)

EXAMPLE 43

Using 1.5 g of D(−)-α-(4-ethyl-2,3-dioxo-1-piperazinocarbonylamino)-p-hydroxyphenylacetic acid and 1.5 g of 7-amino-3-[5-(2-methyl-1,3,4-thiadiazolyl)-thiomethyl]-Δ³-cephem-4-carboxylic acid, the same operation as in Example 41 was repeated to obtain 2.3 g of 7-[D(−)-α-(4-ethyl-2,3-dioxo-1-piperazinocarbonylamino)-p-hydroxyphenylacetamido]-3-[5-(2-methyl-1,3,4-thiadiazolyl)thiomethyl]-Δ³-cephem-4-carboxylic acid, m.p. 172°–177° C. (decomp.), yield 77.7%.

IR (KBr) cm$^{-1}$: $\nu$C=O 1780 (lactam), 1710 (—COOH), 1685, 1672 (—CON<)

In the same manner as above, the objective compounds shown in Table 31 were obtained from D(−)-α-(4-ethyl-2,3-dioxo-1-piperazinocarbonylamino)phenylacetic acid or D(−)-α-(4-ethyl-2,3-dioxo-1-piperazinocarbonylamino)-p-hydroxyphenylacetic acid and the compounds of formula (IV) shown in Table 31. The structure of each objective compound was confirmed by IR and NMR.

Table 31

| Compound of formula (IV) | Objective compound |
|---|---|
| | D(−)- |

Table 31-continued

| Compound of formula (IV) | Objective compound |
|---|---|
| (structure with tetrazole, N-CH₂CH₃) | (structure) m.p. (decomp.) 171–175° C, yield 72.5 % |
| (structure with tetrazole, N-CH₂(CH₂)₂CH₃) | D(−)- (structure) m.p. (decomp.) 156–160° C, yield 73.1 % |
| (structure with tetrazole, N-CH₂CH₃) | D(−)- (structure with p-OH phenyl) m.p. (decomp.) 163–165° C, yield 67.4 % |
| (structure with tetrazole, N-CH₂(CH₂)₂CH₃) | D(−)- (structure with p-OH phenyl) m.p. (decomp.) 159–161° C, yield 68.0 % |
| (structure with thiadiazole) | D(−)- (structure with p-OH phenyl, thiadiazole) m.p. (decomp.) 183–185° C, yield 77.7 % |
| (structure with CH₂OCH₃) | D(−)- (structure with CH₂OCH₃) m.p. (decomp.) 167° C, yield 82.0 % |
| | D(−)- |

Table 31-continued

| Compound of formula (IV) | Objective compound |
|---|---|
| [structure: H₂N-cephem with CH₂OCOCH₃ and COOH] | [structure: CH₃CH₂N-piperazinedione-CONHCHCONH-phenyl(OH)-cephem with CH₂OCOCH₃, COOH]  m.p. (decomp.) 168–174° C, yield 65.0 % |

EXAMPLE 44

In a mixed solvent comprising 80 ml of water and 40 ml of ethyl acetate was suspended 4.0 g of 7-[D(—)-α-aminophenylacetamido]-3-acetoxymethyl-Δ³-cephem-4-carboxylic acid, and 1.65 g of anhydrous potassium carbonate was then dissolved therein with ice-cooling.

To this solution was added 7.3 g of 4-(α-hydroxyethyl)-2,3-dioxo-1-piperazinocarbonyl chloride at 0° to 5° C. over a period of 15 minutes, and the resulting mixture was reacted at 10° to 15° C. for 30 minutes. After the reaction, the aqueous layer was separated off, 100 ml of acetonitrile was added to the aqueous layer, and the resulting solution was adjusted to a pH of 1.5 by addition of dilute hydrochloric acid, and was saturated by sodium chloride. Subsequently, the acetonitrile layer was separated off, successively washed two times with 30 ml of saturated solution of sodium chloride and then dried by reduced pressure. The residue was dissolved in a mixed solvent comprising 50 ml of acetone and 10 ml of ethanol, and insolubles were separated off. Subsequently, 100 ml of isopropyl alcohol was added to the resulting solution, and then concentrated to a liquid amount of about two-thirds under reduced pressure.

The deposited crystals were collected by filtration, washed with iso-propyl alcohol and then dried to obtain 4.5 g of 7-[D(—)-α-4-(β-hydroxyethyl)-2,3-dioxo-1-piperazinocarbonylaminophenylacetamido]-3-acetoxymethyl-:66 ³-cephem-4-carboxylic acid, m.p. 142°–144° C. (decomp.), yield 76.3%.

IR (KBr) cm⁻¹: $\nu_{C=O}$ 1770 (lactam), 1708 (—COOH), 1680, 1665 (—CON<)

The above-mentioned procedure was repeated, except that the 7-[D(—)-α-aminophenylacetamido]-3-acetoxymethyl-Δ³-cephem-4-carboxylic acid was replaced by each of the compounds of formula (II) shown in Table 32, to obtain the respective objective compounds as shown in Table 32. The structure of each objective compound was confirmed by IR and NMR.

Table 32

| Compound of formula (II) | Objective compound |
|---|---|
| [structure: H₂NCHCONH-phenyl(OH)-cephem-CH₂OCOCH₃, COOH] | D(—)— [structure: HOCH₂CH₂N-piperazinedione-NCONHCHCONH-phenyl(OH)-cephem-CH₂OCOCH₃, COOH]  m.p. (decomp.) 153 – 157° C, yield 62.0 % |
| [structure: H₂NCHCONH-phenyl-cephem-CH₂S-tetrazole-CH₃, COOH] | D(—)— [structure: HOCH₂CH₂N-piperazinedione-NCONHCHCONH-phenyl-cephem-CH₂S-tetrazole-CH₃, COOH]  m.p. (decomp.) 141 – 145° C, yield 64.6 % |
| [structure: H₂NCHCONH-phenyl(OH)-cephem-CH₂S-tetrazole-CH₃, COOH] | D(—)— [structure: HOCH₂CH₂N-piperazinedione-NCONHCHCONH-phenyl(OH)-cephem-CH₂S-tetrazole-CH₃, COOH]  m.p. (decomp.) 170 – 173° C, yield 58.0 % |

EXAMPLE 45

(1) To a solution of 0.63 g of D(—)-α-(4-ethyl-2,3-dioxo-1-piperazinocarbonylamino)phenylacetic acid in 10 ml of anhydrous methylene chloride were added 0.5 g of oxalyl chloride and a drop of N,N-dimethylformamide, and the resulting mixture was reacted at room temperature for 30 minutes. After the reaction, the solvent was removed by distillation under reduced pressure. The residue was washed with anhydrous benzene to obtain 0.6 g of D(−)-α-(4-ethyl-2,3-dioxo-1-piperazinocarbonylamino)phenylacetyl chloride, m.p. 112°–116° C. (decomp.), yield 88.8%.

IR (KBr) cm⁻¹: νNH 3280, νC=O 1790, 1695

To a suspension of 0.27 g of 7-aminocephalosporanic acid in 6 ml of anhydrous methanol was added 0.24 g of triethylamine. The resulting solution was cooled to −40° C., and to the solution was added a solution of 5 ml of anhydrous methylene chloride containing 0.34 g of D(−)-α-(4-ethyl-2,3-dioxo-1-piperazinocarbonylamino)phenylacetyl chloride, and then the temperature of the reaction liquid was gradually elevated to room temperature over a period of 1 hour. After the reaction, the solvent was removed by distillation under reduced pressure. The residue was added to 20 ml of water, and the resulting solution was washed two times with 5 ml of ethyl acetate. To the aqueous layer was added 20 ml of ethyl acetate, and the solution was adjusted to a pH of 1.5 by addition of 2N hydrochloric acid with stirring. Subsequently, the organic layer was separated off, washed with saturated aqueous sodium chloride, dried over anhydrous magnesium sulfate, and then the solvent was removed by distillation under reduced pressure to obtain 453 mg of 7-[D(−)-α-(4-ethyl-2,3-dioxo-1-piperazinocarbonylamino)-phenylacetamido]-3-acetoxymethyl-Δ³-cephem-4-carboxylic acid, m.p. 165°–166° C. (decomp.), yield 79.0%.

In the same manner as above, 7-[D(−)-α-(4-ethyl-2,3-dioxo-1-piperazinocarbonylamino)-p-hydroxyphenylacetamido]-3-acetoxymethyl-Δ³-cephem-4-carboxylic acid, m.p. 168°–174° C. (decomp.), yield 72.3%, was obtained from D(−)-α-(4-ethyl-2,3-dioxo-1-piperazinocarbonaylamino)-p-hydroxyphenylacetyl chloride and 7-aminocephalosporanic acid.

EXAMPLE 46

To a suspension of 2.16 g of 6-aminopenicillanic acid in 20 ml of methylene chloride was added 2.02 g of triethylamine. Into the resulting solution was added 3.4 g of D(−)-α-(4-ethyl-2,3-dioxo-1-piperazinocarbonylamino)phenylacetyl chloride at 10° to 15° C., and the resulting mixture was reacted at 10° to 15° C. for 2 hours. After the reaction, the solvent was removed by distillation under reduced pressure. The residue was added to 20 ml of water, and to the resulting solution was added 30 ml of ethyl acetate. The solution was adjusted to a pH of 2.5 by addition of 2N hydrochloric acid and was stirred over a period of 4 hours to deposit crystals. The deposited crystals were collected by filtration to obtain 4.4 g of 6-[D(−)-α-(4-ethyl-2,3-dioxo-1-piperazinocarbonylamino)phenylacetamido]penicillanic acid, m.p. 154°–156° C. (decomp.), yield 82.2%.

In the same manner as above, 6-[D(−)-α-(4-ethyl-2,3-dioxo-1-piperazinocarbonylamino)-p-hydroxyphenylacetamido]penicillanic acid m.p. 160°–161° C. (decomp.), yield 70.5%, was obtained from 6-aminopenicillanic acid and D(−)-α-(4-ethyl-2,3-dioxo-1-piperazinocarbonylamino)-p-hydroxyphenylacetyl chloride.

EXAMPLE 47

Using D(−)-α-(4-ethyl-2,3-dioxo-1-piperazinocarbonylamino)phenylacetic acid and 7-amino-3-carbamoyloxymethyl-Δ³-cephem-4-carboxylic acid, the same procedure as in Example 41 was repeated, to obtain 7-[D(−)-α-(4-ethyl-2,3-dioxo-1-piperazinocarbonylamino)phenylacetamido]-3-carbamoyloxymethyl-Δ³-cephem-4-carboxylic acid, m.p. 175°–180° C. (decomp.), yield 68.0%.

IR (KBr) cm⁻¹: νNH₂ 3450, 3350, νCONH 3300, νC=O 1778, 1710, 1670

In the same manner as above, 7-[D(−)-α-(4-ethyl-2,3-dioxo-1-piperazinocarbonylamino)-p-hydroxyphenylacetamido]-3-carbamoyloxymethyl-Δ³-cephem-4-carboxylic acid, m.p. 178°–182° C. (decomp.), yield 65.0%, was obtained from D(−)-α-(4-ethyl-2,3-dioxo-1-piperazinocarbonylamino)-p-hydroxyphenylacetic acid and 7-amino-3-carbamoyloxymethyl-Δ³-cephem-4-carboxylic acid.

EXAMPLE 48

(1) To a solution of 0.32 g of D(−)-α-(4-ethyl-2,3-dioxo-1-piperazinocarbonylamino)phenylacetic acid in 15 ml of methylene chloride was added 0.1 g of N-methylmorpholine. The resulting solution was cooled to −20° C., and to the solution was added a solution of 0.11 g of ethyl chlorocarbonate in 2 ml of methylene chloride, and then the resulting solution was subjected to reaction at −10° to −20° C. for 1 hour. Subsequently, into the reaction liquid was dropped a solution of 0.44 g of a benzhydryl ester of 7-amino-3-carbamoyloxymethyl-Δ³-cephem-4-carboxylic acid in 5 ml of methylene chloride at −20° C. After the dropping, the resulting solution was subjected to reaction at −10° to −20° C. for 1.5 hours, and the temperature was then elevated to room temperature. Thereafter, the solvent was removed by distillation under reduced pressure, and the residue was dissolved in 15 ml of ethyl acetate. Subsequently, the resulting solution was successively washed with 10 ml of water, with 5% (weight/weight) aqueous sodium hydrogencarbonate, and saturated aqueous sodium chloride, and then dried over anhydrous magnesium sulfate. The solvent was removed by distillation under reduced pressure. Subsequently, the residue was purified, by column chromatography (silica gel - chloroform), to obtain 0.53 g of benzhydryl ester of 7-[D(−)-α-(4-ethyl-2,3-dioxo-1-piperazinocarbonylamino)phenylacetamido]-3-carbamoyloxymethyl-Δ³-cephem-4-carboxylic acid, m.p. 120°–125° C. (decomp.), yield 71.6%.

IR (KBr) cm⁻¹: νNH₂ 3480, 3380, νCONH 3300, νC=O 1780, 1718, 1680

NMR (CDCl₃) τ values: −0.1 (1H, d), 2.05 (1H, d), 2.64 (15H, bs), 3.19 (1H, s), 4.20 (2H, m), 4.86 (1H, d), 5.20 (2H, s), 5.25 (2H, bs), 6.1 (2H, m), 6.3 - 6.9 (6H, m), 8.9 (3H, t)

(2) — To a solution of 0.2 g of a benzhydryl ester of 7-[D(−)-α-(4-ethyl-2,3-dioxo-1-piperazinocarbonylamino)phenylacetamido]-3-carbamoyloxymethyl-Δ³-cephem-4-carboxylic acid in 5 ml of anisole was added 5 ml of trifluoroacetic acid while ice-cooling, and the resulting mixed solution was reacted for 30 minutes while ice-cooling. After the reaction, the solvent was removed by distillation under reduced pressure. Subsequently, the residue was dissolved in 15 ml of ethyl acetate, and to the resulting solution was added 10 ml of water, and then the resulting solution was adjusted to a pH of 7.5 by addition of sodium hydrogencarbonate while stirring. Thereafter, the aqueous layer was separated off, added to 20 ml of ethyl acetate, and then adjusted to a pH of 2.0 by addition of 2N hydrochloric acid. Subsequently, the organic layer was separated off, successively washed with water and saturated aqueous sodium chloride, and then dried over anhydrous magnesium sulfate. The solvent was removed by distillation under reduced pressure to deposit crylstals. Subsequently, the deposited crystals were collected by filtration to obtain 0.13 g of 7-[D(—)-α-(4-ethyl-2,3-dioxo-1-piperazinocarbonylamino)phenylacetamido]-3-carbamoyloxymethyl-Δ³-cephem-4-carboxylic acid, m.p. 175°-180° C. (decomp.), yield 83.8%.

IR (KBr) cm⁻¹: νNH₂ 3450, 3350 νCONH₂ 3300, νC═O 1778, 1710, 1670

NMR (d₆-DNSO) τ values: 0.15 (1H, d), 0.55 (1H, d), 2.60 (5H, b), 3.47 (2H, s), 4.28 (2H, m), 4.95 (1H, d), 5.25 (2H, q), 6.10 (2H, m), 6.25–6.90 (6H, m), 8.9 (3H, t)

EXAMPLE 49

(1) — To a solution of 0.32 g of D(—)-α-(4-ethyl-2,3-dioxo-1-piperazinocarbonylamino)phenylacetic acid in 15 ml of anhydrous methylene chloride was added 0.1 g of N-methylmorpholine. The resulting solution was cooled to −20° C., and to the solution was added a solution of 0.11 g of ethyl chlorocarbonate in 1 ml of methylene chloride, and then the resulting mixed solution was reacted at −10° to −20° C. for 1 hour. Subsequently, into the reaction solution was dropped a solution of 0.46 g of β,β,β-trichloroethyl ester of 7-amino-3-[5-(1-methyl-1,2,3,4-tetrazolyl)-thiomethyl]-Δ³-cephem-4-carboxylic acid in 5 ml of methylene chloride at −20° C. After the dropping, the resulting mixed solution was reacted at −10° to −20° C. for 1 hour, and at room temperature for 30 minutes. After the reaction, the solvent was removed by distillation under reduced pressure, and the residue was successively washed with 5% (weight/weight) aqueous sodium hydrogencarbonate, and with saturated aqueous sodium chloride, and then dried over anhydrous magnesium sulfate. Subsequently, the solvent was removed by distillation under reduced pressure, the residue was purified by column chromatography (silica gel - benzene-ethyl acetate) to obtain 0.53 g of β,β,β-trichloroethyl ester of 7-[D(—)-α-(4-ethyl-2,3-dioxo-1-piperazinocarbonylamino)-phenylacetamido]-3-[5-(1-methyl-1,2,3,4-tetrazolyl)thiomethyl]-Δ³-cephem-4-carboxylic acid, m.p. 125°–135° C. (decomp.), yield 69.6%.

IR (KBr) cm⁻¹: νC═O 1780, 1715, 1680

(2) — To a solution of 0.5 g of β,β,β-trichloroethyl ester of 7-[D(—)-α-(4-ethyl-2,3-dioxo-1-piperazinocarbonylamino)phenylacetamido]-3-[5-(1-methyl-1,2,3,4-tetrazolyl)thiomethyl]-Δ³-cephem-4-carboxylic acid were added 0.5 g of zinc dust and 0.5 ml of acetic acid, and then the resulting mixture was reacted for 1.5 hours. After the reaction, the reaction liquid was subjected to sellaite filtration, and the filtrate was freed from the solvent by distillation under reduced pressure. Thereafter, the residue was dissolved in 15 ml of water, and the resulting solution was adjusted to a pH of 1.5 by addition of 2N hydrochloric acid to deposit crystals. Subsequently, the deposited crystals were collected by filtration, dried and then washed with ethyl acetate to obtain 7-[D(—)-α-(4-ethyl-2,3-dioxo-1-piperazinocarbonylamino)phenylacetamido]-3-[5-(1-methyl-1,2,3,4-tetrazolyl)thiomethyl]-Δ³-cephem-4-carboxylic acid, m.p. 163°–165° C. (decomp.), yield 82.1%.

What is claimed as new and desired to be secured by letters patent of the United States is:

1. An antibacterial compound of the formula (I),

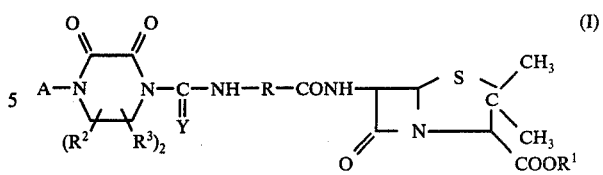

wherein R is a group represented by the formula

wherein $R^5$ represents a conventional penicillin substituent selected from alkyl, cycloalkyl, cycloalkenyl, cycloalkadienyl, aryl, aralkyl, aryloxy, alkylthioalkyl, furyl, thienyl, oxazolyl, thiazolyl, isoxazolyl, isothiazolyl, imidazolyl, pyrazolyl, pyridyl, pyrazyl, pyrimidyl, pyridazyl, quinolyl, isoquinolyl, quinazolyl, indolyl, indazolyl, 1,3,4-oxadiazolyl, 1,2,4-oxadiazolyl, 1,3,4-thiadiazolyl or 1,2,4-thiadiazolyl, each of which may be substituted by halogen, hydroxy, nitro, alkyl, alkoxy, alkylthio, acyl or alkylsulfonylamino; $R^6$ represents a hydrogen atom; and $R^5$ and $R^6$ together with a common carbon atom may form a conventional penicillin substituent selected from cycloalkyl, cycloalkenyl or cycloalkadienyl ring;

$R^1$ represents a hydrogen atom, a conventional penicillin blocking group of a conventional penicillin or a conventional salt-forming cation of a conventional penicillin;

each pair of $R^2$ and $R^3$ are linked to the same carbon atom, and each $R^2$ and $R^3$ in each pair of $R^2$ and $R^3$, which may be the same or different, represent individually a conventional penicillin substituent selected from the group consisting of hydrogen, halogen, carboxyl, or alkyl, cycloalkyl, aryl, acyl, aralkyl, alkoxycarbonylalkyl, acyloxyalkyl, alkoxy, alkoxycarbonyl, cycloalkyloxycarbonyl, aralkoxycarbonyl, aryloxycarbonyl, amino or carbamoyl; any of which may be substituted by halogen, alkyl, alkoxy, alkylthio, acyl or nitro; and any pair of $R^2$ and $R^3$ together with a common carbon atom may form a conventional penicillin substituent which is a cycloalkyl ring;

A represents a conventional penicillin substituent selected from hydrogen, hydroxy, nitro or cyano, or alkyl, alkenyl, alkynyl, alkadienyl, cycloalkyl, cycloalkenyl, cycloalkadienyl, aryl, acyl aralkyl, acyloxyalkyl, alkoxy, cycloalkyloxy, alkoxycarbonyl, aryloxy, cycloalkyloxycarbonyl, aryloxycarbonyl, aralkoxycarbonyl, alkylsulfonyl, cycloalkylsulfonyl, arylsulfonyl, carbamoyl, thiocarbamoyl, acylcarbamoyl, acylthiocarbamoyl, alkylsulfonylcarbamoyl, arylsulfonylcarbamoyl, alkylsulfonylthiocarbamoyl, arylsulfonlthiocarbamoyl, sulfamoyl, alkoxycarbonylthioalkyl, alkoxythiocarbonylthioalkyl, amino, thiazolyl, pyridyl, pyridazyl, pyrazyl, thiadiazolyl, triazolyl, tetrazolyl or quinolyl, each of which may be substituted by a conventional penicillin substituent selected from the group consisting of halogen, hydroxyl, alkyl, alkoxy, alkylthio, nitro, cyano, amino, carboxyl or acyl; and Y represents an oxygen or sulfur atom.

2. An antibacterial compound of claim 1 of the formula

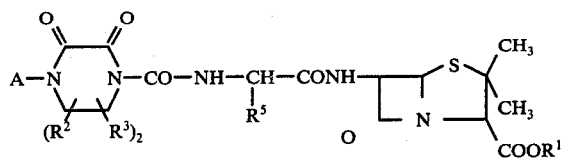

wherein $R^5$ represents a conventional penicillin substituent selected from alkyl, cycloalkyl, cycloalkenyl, cycloalkadienyl, aryl, aralkyl, aryloxy, alkylthioalkyl, furyl, thienyl, oxazolyl, thiazolyl, isoxazolyl, isothiazolyl, imidazolyl, pyrazolyl, pyridyl, pyrazyl, pyrimidyl, pyridazyl, quinolyl, isoquinolyl, quinazolyl, indolyl, indazolyl, 1,3,4-oxadiazolyl, 1,3,4-thiadiazolyl or 1,2,4-thiadiazolyl, each of which may be substituted by halogen, hydroxy, nitro, alkyl, or alkoxy;

$R^1$ represents a hydrogen atom, a conventional penicillin blocking group of a conventional penicillin or a conventional salt-forming cation of a conventional penicillin;

each pair of $R^2$ and $R^3$ are linked to the same carbon atom and each $R^2$ and $R^3$ in each pair of $R^2$ and $R^3$, which may be the same or different, represent individually a conventinal penicillin substituent selected from hydrogen, halogen, carboxyl, or alkyl, cycloalkyl, aryl, acyl, aralkyl, acyloxyalkyl, alkoxy, alkoxycarbonyl, cycloalkyloxycarbonyl, aralkoxycarbonyl, aryloxycarbonyl, amino or carbamoyl; any of which may be substituted by halogen, alkyl, alkoxy or acyl;

A represents a conventional penicillin substituent selected from hydrogen, hydroxy, nitro or cyano, or alkyl, alkenyl, alkynyl, alkadienyl, cycloalkyl, cycloalkenyl, cycloalkadienyl, aryl, acyl, aralkyl, acyloxyalkyl, alkoxy, cycloalkyloxy, alkoxycarbonyl, aryloxy, cycloalkyloxycarbonyl, aryloxycarbonyl, aralkoxycarbonyl, alkylsulfonyl, cycloalkylsulfonyl, arylsulfonyl, carbamoyl, thiocarbamoyl, acetyl carbamoyl, acetylthiocarbamoyl, methanesulfonylcarbamoyl, methanesulfonylthiocarbamoyl, sulfamoyl, amino, thiazolyl, pyridyl, pyridazyl or pyrazyl, each of which may be substituted by a conventional penicillin substituent selected from halogen, alkyl, alkoxy, nitro, cyano, amino, carboxyl or acyl.

3. An antibacterial compound of claim 2, wherein
A is a conventional penicillin substituent selected from hydrogen, alkyl, alkenyl, aryl or aralkyl, any of which may be substituted by halogen, alkyl, alkoxy, nitro, cyano amino, carboxyl or acyl; and $R^2$ and $R^3$ are individually hydrogen or alkyl.

4. An antibacterial compound of claim 1, wherein $R^1$ is selected from the group consisting of ester-forming groups capable of being removed by catalytic reduction, chemical reduction or hydrolysis under mild conditions and ester-forming groups capable of being easily removed by enzymes in a living body.

5. An antibacterial compound of claim 1, wherein $R^1$ is a cation capable of forming a non-toxic salt.

6. An antibacterial compound of claim 1, wherein R is

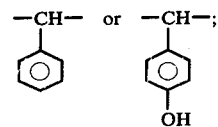

each $R^2$ and $R^3$ of each pair of $R^2$ and $R^3$, which may be the same or different, are individually a hydrogen atom or a methyl group; A is a methyl or ethyl group; and $R^1$ is a hydrogen atom or a conventional penicillin cation capable of forming a non-toxic salt.

7. A compound of the formula (I),

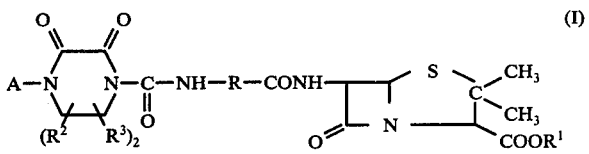

wherein R represents an α-amino acid residue represented by the formula,

wherein $R^5$ represents $C_{1-8}$alkyl, $C_{5-7}$cycloalkyl, $C_{5-6}$cycloalkenyl, $C_{5-6}$cycloalkadienyl, naphthyl, benzyl, phenoxy, naphthoxy, $C_{1-2}$alkylthio$C_{1-2}$alkyl, furyl, thienyl, oxazolyl, thiazolyl, isoxazolyl, isothiazolyl, imidazolyl, pyrazolyl, pyridyl, pyrazyl, pyrimidyl, pyridazyl, quinolyl, isoquinolyl, quinazolyl, indolyl, indazolyl, 1,3,4-oxadiazolyl, 1,3,4-thiadiazolyl, 1,2,4-thiadiazolyl or phenyl, any of which may be optionally substituted by halogen, hydroxy or nitro; $R^6$ represents a hydrogen atom; $R^5$ and $R^6$ together with a common carbon atom may form a $C_{6-7}$cycloalkyl, $C_{5-6}$cycloalkenyl or $C_{5-6}$cycloalkadienyl ring;

$R^1$ represents a hydrogen atom, a conventional penicillin blocking group of a conventional penicillin or a conventional penicillin salt-forming cation of a conventional penicillin;

each pair of $R^2$ and $R^3$ are linked to the same carbon atom, and each $R^2$ and $R^3$ in each pair of $R^2$ and $R^3$, which may be the same or different, represent individually, hydrogen, halogen or carboxyl, or $C_{1-8}$alkyl, $C_{5-7}$cycloalkyl, phenyl, naphthyl, acetyl, benzolyl, benzyl, acetyloxymethyl, pivaloyloxymethyl, $C_{1-4}$alkoxy, $C_{1-3}$-alkoxycarbonyl, $C_{5-7}$cycloalkyloxycarbonyl, benzyloxycarbonyl, phenoxycarbonyl, amino, N-$C_{1-4}$alkylamino, N,N-di-$C_{1-4}$-alkylamino, N-acetylamino, or carbamoyl, any of which may be optionally substituted by halogen;

A represents hydrogen, hydroxy, nitro or cyano, or $C_{1-12}$alkyl, $C_{2-4}$alkenyl, propargyl, $C_{4-5}$alkadienyl, $C_{5-7}$cycloalkyl, $C_{5-6}$cycloalkenyl, $C_{5-6}$cycloalkadienyl, phenyl, naphthyl, formyl, acetyl, propionyl, benzoyl, furoyl, thenoyl, benzyl, acetyloxyethyl, pivaoyloxymethyl, $C_{1-4}$-alkoxy, $C_{5-7}$cycloalkyloxyl, phenoxy, naphthoxy, $C_{1-4}$alkoxycarbonyl, $C_{5-7}$cycloalkyloxycarbonyl, phenoxycarbonyl, benzyloxycarbonyl, $C_{1-4}$alkylsulfonyl, $C_{5-6}$cycloalkylsulfonyl, benzenesulfonyl, carbamoyl, N-$C_{1-4}$alkylaminocarbonyl, N-phenylaminocarbonyl, N,N- di-$C_{1-2}$alkylaminocarbonyl, pyrrolidinocarbonyl, piperidinocarbonyl, thiocarbamoyl, N-$C_{1-3}$alkylaminothiocarbonyl, N-phenylaminothiocarbonyl, N,N-di-$C_{1-2}$alkylaminothiocarbonyl, pyrrolidinothiocarbonyl, piperidinothiocarbonyl, N-acetylcarbamoyl, N-acetylthiocarbamoyl, $C_{1-4}$alkylsurfonylcarbamoyl, $C_{1-4}$alkylsulfonylthiocarbamoyl, sulfamoyl, N-methylsulfamoyl, N-ethylsulfamoyl, N,N-dimethylsulfamoyl, N-phenylsulfamoyl, N-cyclohexylsulfamoyl, amino, $C_{1-4}$alkylamino, N,N-di-$C_{1-4}$alkylamino,N-acetylamino, thiazolyl, pyridyl, pyridazyl or pyrazyl, any of which may be optionally substituted by halogen, nitro, cyano, carboxyl.

8. A compound of the formula (I),

wherein R represents an α-amino acid residue represented by the formula,

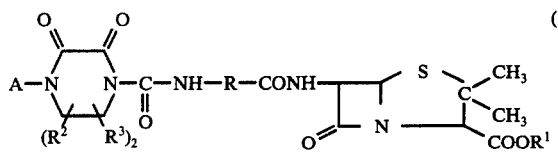

wherein $R^5$ represents $C_{1-8}$alkyl, $C_{5-7}$cycloalkyl, $C_{5-6}$cycloalkenyl, $C_{5-6}$cycloalkadienyl, naphthyl, benzyl, phenoxy, naphthoxy, furyl, thienyl, oxazolyl, thiazolyl, isoxazolyl, isothiazolyl, imidazolyl, pyrazolyl, pyridyl, pyrazyl, pyrimidyl, pyridazyl, quinolyl, isoquinolyl, quinazolyl, indolyl, indazolyl, 1,3,4-oxadiazolyl, 1,3,4-thiadiazolyl, 1,2,4-thiadiazolyl or phenyl, any of which may be optionally substituted by halogen, hydroxy or nitro; $R^6$ represents a hydrogen atom; $R^5$ and $R^6$ together with a common carbon atom may form a $C_{6-7}$cycloalkyl, $C_{5-6}$cycloalkenyl or $C_{5-6}$cycloalkadienyl ring;

$R^1$ represents a hydrogen atom, a conventional penicillin blocking group of a conventional penicillin or a conventional penicillin salt-forming cation of a conventional penicillin;

each pair of $R^2$ and $R^3$ are linked to the same carbon atom, and each $R^2$ and $R^3$ in each pair of $R^2$ and $R^3$, which may be the same or different, represent individually, hydrogen, halogen or carboxyl, or $C_{1-8}$alkyl, phenyl, naphthyl, benzyl, $C_{1-3}$alkoxycarbonyl, benzyloxycarbonyl, phenoxycarbonyl or carbamoyl, any of which may be optionally substituted by halogen;

A represents hydrogen or $C_{1-12}$alkyl, $C_{2-4}$alkenyl, propargyl, $C_{5-7}$cycloalkyl, phenyl, naphthyl, formyl, acetyl, propionyl, benzoyl, furoyl, thenoyl, benzyl, pivaloyloxymethyl, $C_{1-4}$alkoxycarbonyl, $C_{5-7}$cyclo alkyloxycarbonyl, phenoxycarbony, benzyloxycarbonyl, $C_{1-4}$alkylsufonyl, $C_{5-6}$-cycloalkylsulfonyl, benzenesulfonyl, carbamoyl, N-$C_{1-4}$alkylaminocarbonyl, N-phenylaminocarbonyl, N,N-di-$C_{1-2}$alkyaminocarbonyl, pyrrolidinocarbonyl, piperidinocarbonyl, thiocarbamoyl, N-$C_{1-3}$alkylaminothiocarbonyl, pyrrolidinothiocarbonyl, piperidinothiocarbonyl, N-acetylcarbamoyl, N-acetylthiocarbamoyl, $C_{1-4}$alkylsulfonylcarbamoyl, $C_{1-4}$alkylsulfonylthiocarbamoyl, sulfamoyl, N-methylsulfamoyl, N-ethylsulfamoyl, N,N-dimethylsulfamoyl, N-phenylsulfamoyl, N-cyclohexylsulfamoyl, thiazolyl, pyridyl, pyridazyl, pyrazyl, any of which may be optionally substituted by halogen or nitro.

9. A compound of claim 7 wherein $R^5$ represents $C_{1-8}$alkyl, $C_{5-6}$cycloalkadienyl, 2-thienyl or phenyl each of which may be optionally substituted by halogen, hydroxy or nitro; $R^6$ represents a hydrogen atom; each pair of $R^2$ and $R^3$ are linked to the same carbon atom, and each $R^2$ and $R^3$ in each pair of $R^2$ and $R^3$, which may be the same or different, represent individually hydrogen, $C_{1-8}$alkyl or phenyl; and A represents hydrogen or $C_{1-12}$alkyl, $C_{2-4}$alkenyl, $C_{5-7}$cycloalkyl, phenyl, formyl, acetyl, propionyl, benzoyl, benzyl, acetyloxyethyl, pivaloyloxymethyl, $C_{1-4}$alkylsulfonyl, carbamoyl, N-acetylcarbamoyl, N-phenylaminocarbonyl or $C_{1-4}$alkoxycarbonyl any of which may be optionally substituted by a halogen atom.

10. A compound of claim 7 wherein $R^5$ represents a $C_{1-8}$alkyl, $C_{5-6}$cycloalkadienyl, thienyl or phenyl any of which may be optionally substituted by halogen, hydroxy or nitro; $R^6$ represnets a hydrogen atom; A is hydrogen or $C_{1-12}$alkyl, $C_{2-4}$alkenyl, phenyl or benzyl each of which may be optionally substituted by halogen; each pair of $R^2$ and $R^3$ are linked to the same carbon atom, each $R^2$ and $R^3$ in the two pairs of $R^2$ and $R^3$, which may be the same or different, are individually hydrogen or $C_{1-8}$alkyl; and $R^1$ is a hydrogen atom, a conventional penicillin cation capable of forming a non-toxic salt or a conventional penicillin ester-forming group capable of being easily removed by enzymes in a living body.

11. A compound of claim 7, wherein $R^5$ represents phenyl or 4-hydroxyphenyl; $R^6$ represents hydrogen; each pair of $R^2$ and $R^3$ are linked to the same carbon atom, and each $R^2$ and $R^3$ in the two pairs of $R^2$ and $R^3$, which may be the same of different, are individually hydrogen or methyl; A is methyl or ethyl; and $R^1$ is hydrogen or a conventional penicillin cation capable of forming a non-toxic salt.

12. A compound selected from the group consisting of phthalidyl 6-[D(—)-α-(4-methyl-2,3-dioxo-1-piperazinocarbonylamino)phenylacetamido]-penicillanate, phthalidyl 6-[D(—)-α-(4-ethyl-2,3-dioxo-1-piperazinocarbonylamino)phenylacetamido]-penicillanate, phthalidyl 6-[D(—)-α-(4-iso-propyl-2,3-dioxo-1-piperazinocarbonylamino)phenylacetamido]-penicillanate, phthalidyl 6-[D(—)-α-(4-n-butyl-2,3-dioxo-1-piperazinocarbonylamino)phenylacetamido]-penicillanate, methoxymethyl 6-[D(—)-α-(4-methyl-2,3-dioxo-1-piperazinocarbonylamino)phenylacetamido]-penicillanate, methoxymethyl 6-[D(—)-α-(4-ethyl-2,3-dioxo-1-piperazinocarbonylamino)phenylacetamido]-penicillanate, methoxymethyl 6-[D(—)-α-(4-n-butyl-2,3-dioxo-1-piperazinocarbonylamino)phenylacetamido]-penicillanate, methoxymethyl 6-[D(—)-α-(4-iso-propyl-2,3-dioxo-1-piperazinocarbonylamino)phenylacetamido]-penicillanate, methoxymethyl 6-[D(—)-α-(4-n-octyl-2,3-dioxo-1-piperazinocarbonylamino)phenylacetamido]-penicillanate, pivaloyloxymethyl 6-[D(—)-α-(4-methyl-2,3-dioxo-1-piperazinocarbonylamino)phenylacetamido]-penicillanate, pivaloyloxymethyl 6-[D(—)-α-(4-ethyl-2,3-dioxo-1-piperazinocarbonylamino)phenylacetamido]-penicillanate, pivaloyloxymethyl 6-[D(—)-α-(4-n-octyl-2,3-dioxo-1-piperazinocarbonylamino)phenylacetamido]-penicillanate, β-piperidinoethyl 6-[D(—)-α-(4-methyl-2,3-dioxo-1-piperazinocarbonylamino)phenylacetamido]-penicillanate, β-piperidinoethyl 6-[D(—)-α-(4-n-octyl-2,3-dioxo-1-piperazinocarbonylamino)phenylacetamido]-penicillanate, β-morpholinoethyl 6-[D(—)-α-(4-methyl-2,3-dioxo-1-piperazinocarbonylamino)phenylacetamido]-penicillanate, and β-morpholinoethyl 6-[D(—)-α-(4-n-octyl-2,3-dioxo-1-piperazinocarbonylamino)phenylacetamido]-penicillanate.

13. The compound of claim 7, which is 6-[D(—)-α-(4-ethyl-2,3-dioxo-1-piperazinocarbonylamino)-phenylacetamido]penicillanic acid of the formula

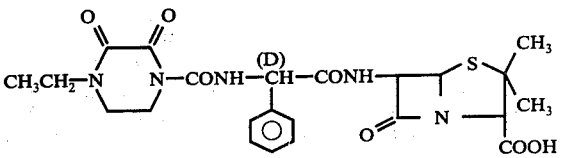

or a non-toxic salt thereof.

14. The compound of claim 7 which is 6-[D(—)-α-(4-methyl-2,3-dioxo-1-piperazinocarbonylamino)-phenylacetamido]penicillanic acid of the formula

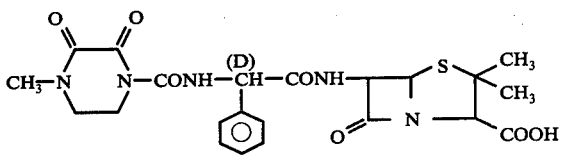

or a non-toxic salt thereof.

15. The compound of claim 7 which is 6-[D(—)-α-(4-n-propyl-2,3-dioxo-1-piperazinocarbonylamino)-phenylacetamido]penicillanic acid of the formula

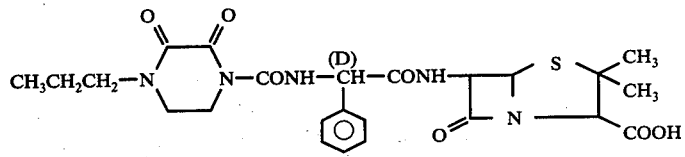

or a non-toxic salt thereof.

16. The compound of claim 7 which is 6-[D(—)-α-(4-n-butyl-2,3-dioxo-1-piperazinocarbonylamino)-phenylacetamido]pencillanic acid of the formula

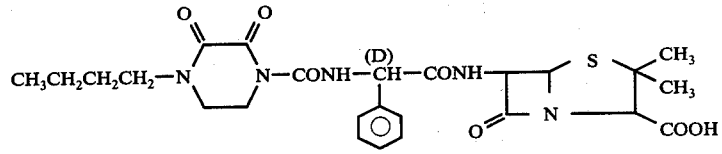

or a non-toxic salt thereof.

17. The compound of claim 7 which is 6-[D(—)-α-(4-iso-propyl-2,3-dioxo-1-piperazinocarbonylamino)-phenylacetamido]penicillanic acid of the formula

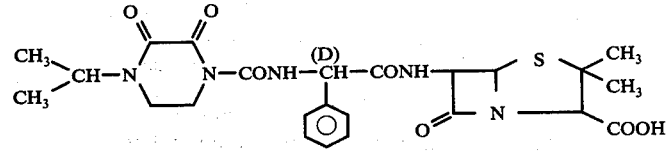

or a non-toxic salt thereof.

18. The compound of claim 7 which is 6-[D(—)-α-(4-acetoxyethyl-2,3-dioxo-1-piperazinocarbonylamino)-phenylacetamido]penicillanic acid of the formula

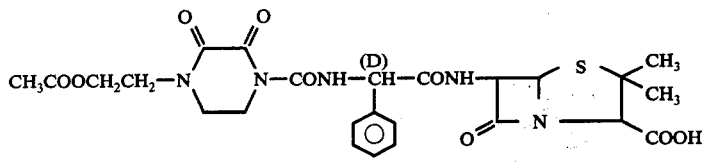

or a non-toxic salt thereof.

19. The compound of claim 7 which is 6-[D(—)-α-(4-allyl-2,3-dioxo-1-piperazinocarbonylamino)-phenylacetamido]penicillanic acid of the formula

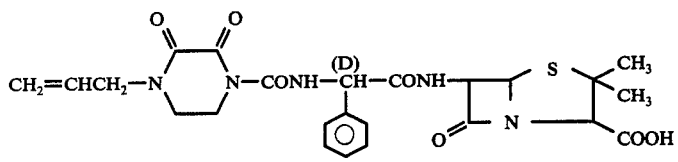

or a non-toxic salt thereof.

20. The compound of claim 7 which is 6-[D(—)-α-(4-phenyl-2,3-dioxo-1-piperazinocarbonylamino)-phenylacetamido]penicillanic acid of the formula

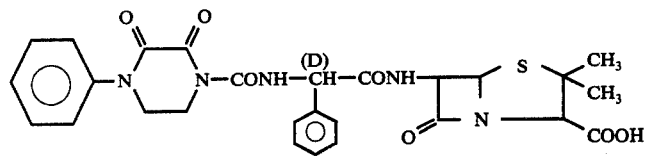

or a non-toxic salt thereof.

21. The compound of claim 7 which is 6-[D(—)-α-(4-β-chloroethyl-2,3-dioxo-1-piperazinocarbonylamino)-phenylacetamido]penicillanic acid of the formula

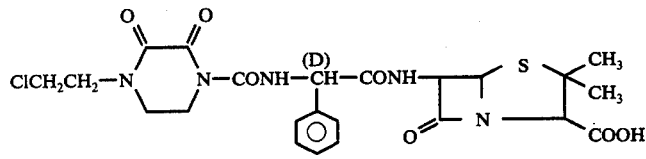

or a non-toxic salt thereof.

22. The compound of claim 7 which is 6-[D(—)-α-(6-methyl-4-ethyl-2,3-dioxo-1-piperazinocarbonylamino)-phenylacetamido]penicillanic acid of the formula

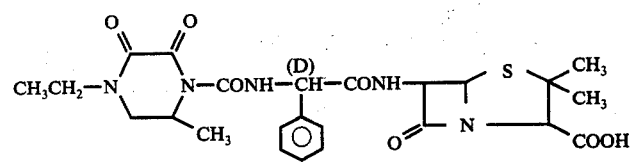

or a non-toxic salt thereof.

23. The compound of claim 7 which is 6-[D(—)-α-(4,6-dimethyl-2,3-dioxo-1-piperazinocarbonylamino)-phenylacetamido]penicillanic acid of the formula

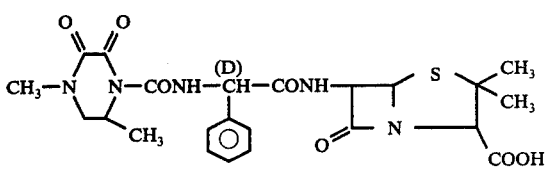

or a non-toxic salt thereof.

24. The compound of claim 7 which is 6-[D(—)-α-(4-n-pentyl-2,3-dioxo-1-piperazinocarbonylamino)-phenylacetamido]penicillanic acid of the formula

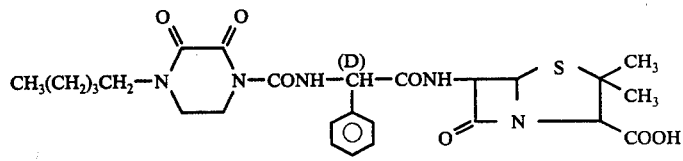

or a non-toxic salt thereof.

25. The compound of claim 7 which is 6-[D(—)-α-(4-n-hexyl-2,3-dioxo-1-piperazinocarbonylamino)-phenylacetamido]penicillanic acid of the formula

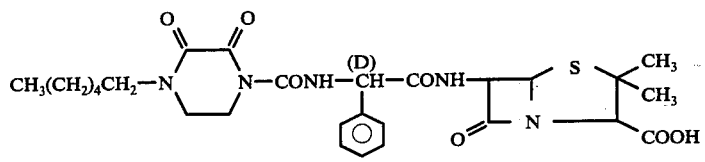

or a non-toxic salt thereof.

26. The compound of claim 7 which is 6-[D(—)-α-(4-n-heptyl-2,3-dioxo-1-piperazinocarbonylamino)-phenylacetamido]penicillanic acid of the formula

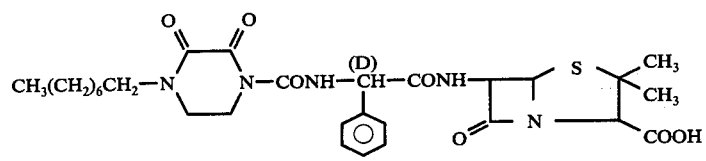

or a non-toxic salt thereof.

27. The compound of claim 7 which is 6-[D(—)-α-(4-n-octyl-2,3-dioxo-1-piperazinocarbonylamino)-phenylacetamido]penicillanic acid of the formula

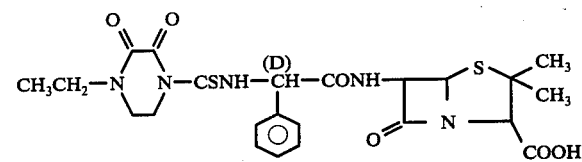

or a non-toxic salt thereof.

28. The compound of claim 1 which is 6-[D(—)-α-(4-ethyl-2,3-dioxo-1-piperazinothiocarbonylamino)-phenylacetamido]penicillanic acid of the formula

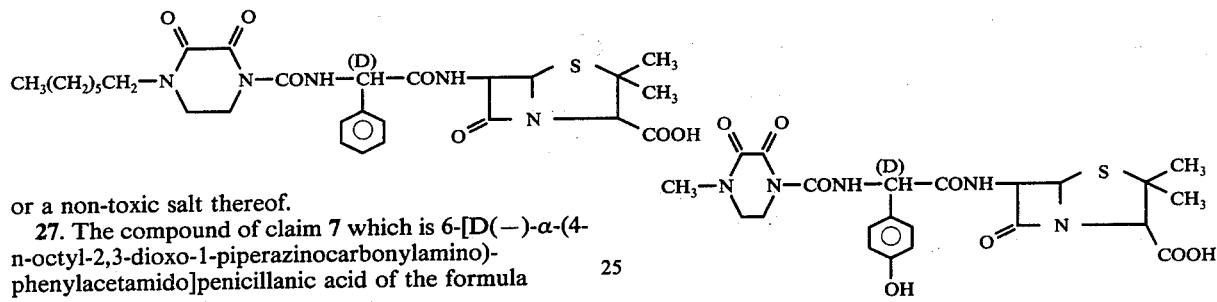

or a non-toxic salt thereof.

30. The compound of claim 7 which is 6-[D(—)-α-(4-ethyl-2,3-dioxo-1-piperazinocarbonylamino)-p-hydroxyphenylacetamido]penicillanic acid of the formula

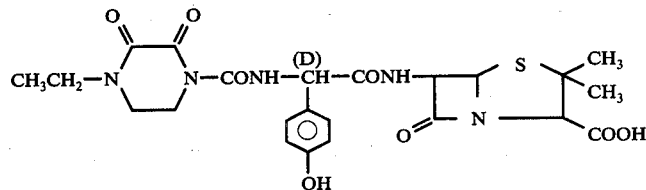

or a non-toxic salt thereof.

31. The compound of claim 7 which is 6-[D(—)-α-(4-methyl-2,3-dioxo-1-piperazinocarbonylamino)-1,4-cyclohexadienylacetamido]penicillanic acid of the formula or a non-toxic salt thereof.

29. The compound of claim 7 which is 6-[D(—)-α-(4-methyl-2,3-dioxo-1-piperazinocarbonylamino)-p-hydroxyphenylacetamido]penicillanic acid of the formula or a non-toxic salt thereof.

32. The compound of claim 7 which is 6-[D(—)-α-(4-ethyl-2,3-dioxo-1-piperazinocarbonylamino)-1,4-cyclohexadienylacetamido]penicillanic acid of the formula

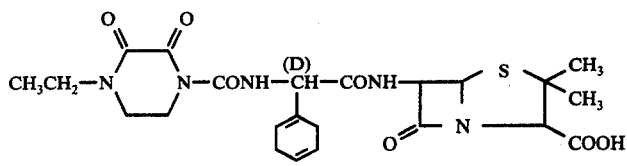

or a non-toxic salt thereof.

33. The compound of claim 7 which is 6-[D(—)-α-(4-n-propyl-2,3-dioxo-1-piperazinocarbonylamino)-1,4-cyclohexadienylacetamido]penicillanic acid of the formula

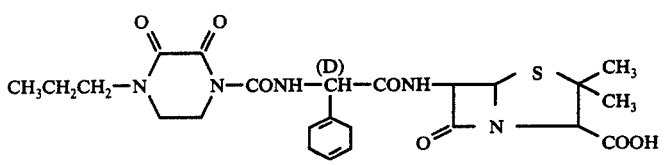

or a non-toxic salt thereof.

34. The compound of claim 7 which is 6-[D(—)-α-(4-n-butyl-2,3-dioxo-1-piperazinocarbonylamino)-1,4-cyclohexadienylacetamido]penicillanic acid of the formula

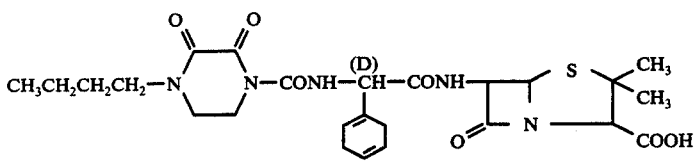

or a non-toxic salt thereof.

35. The compound of claim 7 which is 6-[DL-α-(4-methyl-2,3-dioxo-1-piperazinocarbonylamino)-2-thienylacetamido]penicillanic acid of the formula

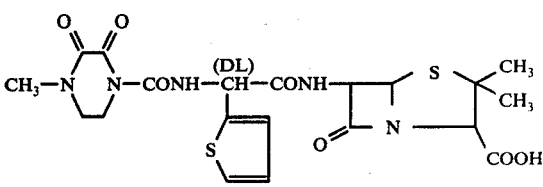

or a non-toxic salt thereof.

36. The compound of claim 7 which is 6-[DL-α-(4-ethyl-2,3-dioxo-1-piperazinocarbonylamino)-2-thienylacetamido]penicillanic acid of the formula

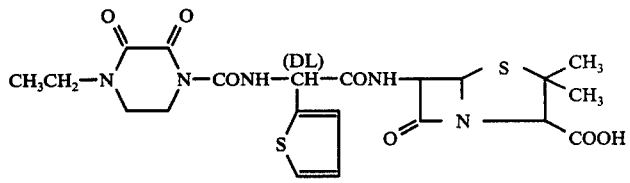

or a non-toxic salt thereof.

37. The compound of claim 7 which is 6-[DL-α-(4-n-propyl-2,3-dioxo-1-piperazinocarbonylamino)-2-thienylacetamido]penicillanic acid of the formula

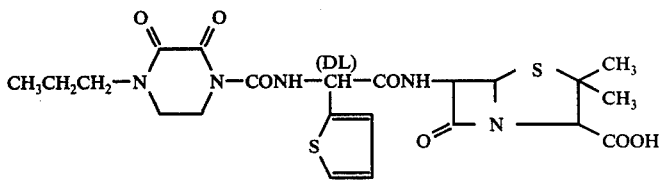

or a non-toxic salt thereof.

38. The compound of claim 7 which is 6-[DL-α-(4-n-butyl-2,3-dioxo-1-piperazinocarbonylamino)-2-thienylacetamido]penicillanic acid of the formula

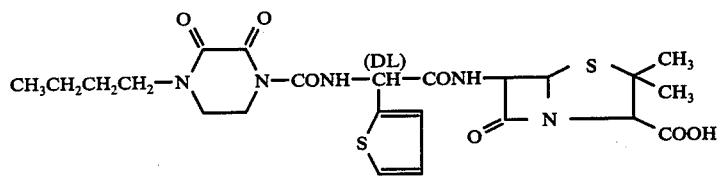
or a non-toxic salt thereof.
39. A pharmaceutical composition comprising an antibacterially effective amount of a compound of claim 1 and a pharmaceutically acceptable carrier.
40. A method of combatting bacteria in mammals which comprises administering to said mammal an antibacterially effective amount of a compound of claim 1.
* * * * *

UNITED STATES PATENT AND TRADEMARK OFFICE
CERTIFICATE OF CORRECTION

PATENT NO. : 4,112,090
DATED : September 5, 1978
INVENTOR(S) : Saikawa et al

It is certified that error appears in the above—identified patent and that said Letters Patent is hereby corrected as shown below:

Front page, right column, between lines 1 and 2: Insert the following statement: --Mar. 27, 1975 [JP] Japan ----- 50-37207--

Column 1, line 12, Delete "1" and start line at regular paragraph indentation

Column 1, line 62; delete "pencillins" and insert --penicillins--

Column 2, lines 12, 15 and 19; correct spelling of "pencillins" to --penicillins--

Column 2, line 8, delete "the" and insert --this--

UNITED STATES PATENT AND TRADEMARK OFFICE
CERTIFICATE OF CORRECTION

PATENT NO. : 4,112,090
DATED : September 5, 1978
INVENTOR(S) : Saikawa et al

It is certified that error appears in the above—identified patent and that said Letters Patent is hereby corrected as shown below:

Column 2, lines 22 to 30; delete structural formula

" 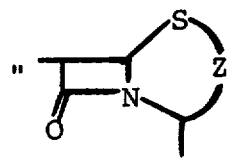 " and insert -- 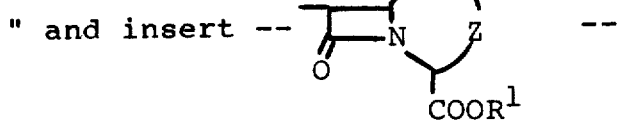 --

Column 6, line 59; delete "thylaminocarboxyloxy" and insert --thylaminocarbonyloxy--.

Column 7, line 65; delete part of the structural formula:

" 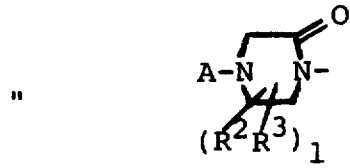 " and insert --  --

UNITED STATES PATENT AND TRADEMARK OFFICE
CERTIFICATE OF CORRECTION

PATENT NO. : 4,112,090
DATED : September 5, 1978
INVENTOR(S) : Saikawa et al

It is certified that error appears in the above—identified patent and that said Letters Patent is hereby corrected as shown below:

Column 8, line 5 delete part of the first structural formula:

" 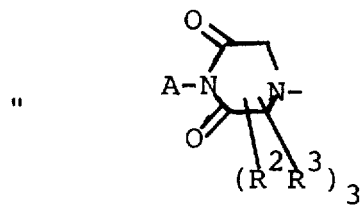 " and insert -- 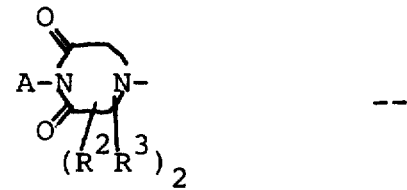 --

Column 9, line 45; insert a --,-- between the words "groups" and "alkyl"

Column 10, line 37; delete "J. An." and insert --J. Am.--

Column 11, under the Compound heading delete the third structural formula

UNITED STATES PATENT AND TRADEMARK OFFICE
CERTIFICATE OF CORRECTION

PATENT NO. : 4,112,090
DATED : September 5, 1978
INVENTOR(S) : Saikawa et al

It is certified that error appears in the above—identified patent and that said Letters Patent is hereby corrected as shown below:

" 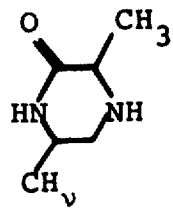  " and insert -- 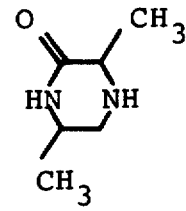 --

Column 12, under the IR heading, delete in the fourth set of frequencies "3380" and insert --3300--.

Column 12, under the IR heading, delete in the fifth set of frequencies "3190" and insert --3220--.

UNITED STATES PATENT AND TRADEMARK OFFICE
CERTIFICATE OF CORRECTION

PATENT NO. : 4,112,090
DATED : September 5, 1978
INVENTOR(S) : Saikawa et al

It is certified that error appears in the above—identified patent and that said Letters Patent is hereby corrected as shown below:

Column 17 to 18, under the IR heading delete in the twelfth set of frequencies "3300" and insert --3350--.

Columns 35 to 36, under the compound heading delete the first structural formula

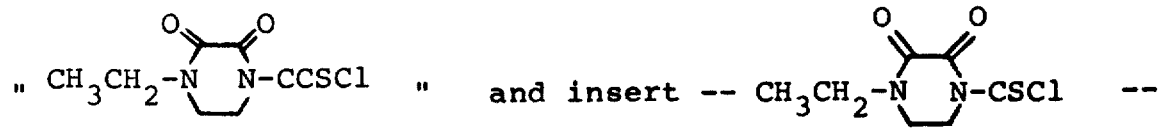

UNITED STATES PATENT AND TRADEMARK OFFICE
CERTIFICATE OF CORRECTION

PATENT NO. : 4,112,090
DATED : September 5, 1978
INVENTOR(S) : Saikawa et al

It is certified that error appears in the above—identified patent and that said Letters Patent is hereby corrected as shown below:

Columns 35 to 36; delete the last structural formula

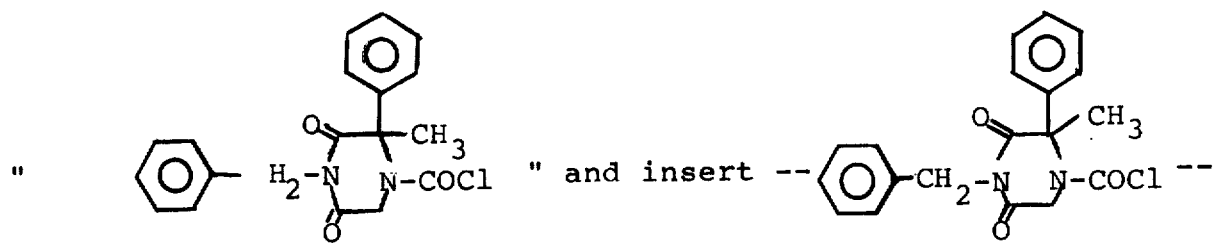

Column 41, line 40; delete "anyone" and insert --any one--.

Column 47, line 58; delete "("

UNITED STATES PATENT AND TRADEMARK OFFICE
CERTIFICATE OF CORRECTION

PATENT NO. : 4,112,090
DATED : September 5, 1978
INVENTOR(S) : Saikawa et al

It is certified that error appears in the above—identified patent and that said Letters Patent is hereby corrected as shown below:

Columns 51 to 76; delete in the headings "coil" and insert --coli--

Column 65 to 66; delete part of the first structural formula

" 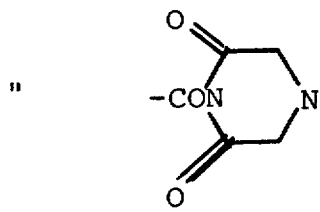 " and insert -- 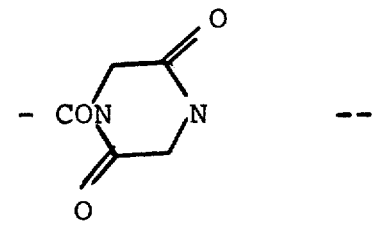 --

Column 75, under the heading Escherichia Coli NIHJ delete

UNITED STATES PATENT AND TRADEMARK OFFICE
CERTIFICATE OF CORRECTION

PATENT NO. : 4,112,090
DATED : September 5, 1978
INVENTOR(S) : Saikawa et al

It is certified that error appears in the above—identified patent and that said Letters Patent is hereby corrected as shown below:

the value "<1/57" and insert --<1.57--

Column 87 to 88, table 5.5; delete the line that extends across the page immediately above the word "compound" and insert a new line extending across the page immediately above the word "control", but immediately below "2136"

Columns 87 through 89 delete in Tables 6-1 to 6-4 "Cephalorizine" and insert --Cephaloridine-- throughout.

Column 89, line 68; delete "aerugionsa" and insert --aeruginosa--.

Column 91, line 45, delete "Cephalorigine" and insert --Cephaloridine--.

UNITED STATES PATENT AND TRADEMARK OFFICE
CERTIFICATE OF CORRECTION

PATENT NO. : 4,112,090
DATED : September 5, 1978
INVENTOR(S) : Saikawa et al

It is certified that error appears in the above—identified patent and that said Letters Patent is hereby corrected as shown below:

Column 91, Table 7-2; delete "Cephalorigine" and insert --Cephaloridine--.

Column 91, Table 7-2; delete "Cephazoline" and insert --Cephazolin--.

Column 92, line 63; delete "4-acetyl-2-oxo" and insert ---4-acetyl-2-oxo-1- --.

Columns 93 to 94, Table 8, the "Objective compound" column; Under the third structural formula, delete "yield 87.5%" and insert --yield 87.7%--.

Column 93 to 94, Table 8, the "Objective compound" column delete part of the forth structural formula:

UNITED STATES PATENT AND TRADEMARK OFFICE
CERTIFICATE OF CORRECTION

PATENT NO. : 4,112,090
DATED : September 5, 1978
INVENTOR(S) : Saikawa et al

It is certified that error appears in the above—identified patent and that said Letters Patent is hereby corrected as shown below:

" 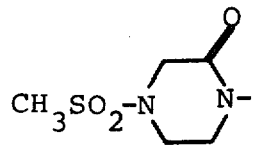 " and insert -- 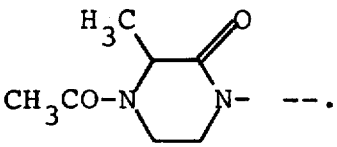 --.

Column 96, line 53; column 97, line 37; column 98, line 31; column 101, line 45; column 102, line 39; column 106, line 63; column 107, line 34; column 108, lines 5 and 33; column 109, line 67; column 110, line 67; column 114, line 53; column 115, line

UNITED STATES PATENT AND TRADEMARK OFFICE
CERTIFICATE OF CORRECTION

PATENT NO. : 4,112,090
DATED : September 5, 1978
INVENTOR(S) : Saikawa et al

It is certified that error appears in the above-identified patent and that said Letters Patent are hereby corrected as shown below:

20; column 116 line 1; column 120, line 6; column 121, line 9; column 122, line 18; column 123, line 65; column 125, lines 4 and 26; column 126, line 4; column 128, line 39; column 129, line 36; column 130, line 38; column 132, line 22; column 135, line 3; column 136, line 12; column 137, line 24; column 138, line 25; column 139, line 47; column 140, line 48; column 143, line 12; and column 144, lines 3 and 62: delete "$-\nu_{C=O}$" and insert --$\nu_{C=O}$--

Column 96, line 54; column 97, lines 22 and 38; column 101, lines 15, 36 and 46; column 105, line 51; column 106, line 64; column 107, line 38; column 108, line 6; column 111, lines 3 and

UNITED STATES PATENT AND TRADEMARK OFFICE
CERTIFICATE OF CORRECTION

PATENT NO. : 4,112,090  
DATED : September 5, 1978  
INVENTOR(S) : Saikawa et al It is certified that error appears in the above-identified patent and that said Letters Patent are hereby corrected as shown below:

19; column 113, line 46; column 114, line 54; column 115, lines 24 and 32; column 116, line 2; column 125, line 40; column 126, lines 5 and 15; column 127, lines 21 and 47; column 129, lines 22 and 37 and 47; column 134, line 57; column 135, line 4; column 139, lines 33 and 51; column 149, line 62; column 151, line 7; column 168, line 52 and column 169, lines 17 and 47: Delete "-" following "(1)", "(2)", or "(3)" at the beginning of a paragraph.

Column 98, line 4; delete "palmitoyl-2-" and insert --4-palmitoyl-2- --.

Column 108, line 6, delete "6[D(-)- " and insert -- 6-[D(-)- --.

UNITED STATES PATENT AND TRADEMARK OFFICE
CERTIFICATE OF CORRECTION

PATENT NO. : 4,112,090

DATED : September 5, 1978

INVENTOR(S) : Saikawa et al

It is certified that error appears in the above—identified patent and that said Letters Patent is hereby corrected as shown below:

Column 111, line 22, delete --or-- and insert -of--.

Column 115, line 27, delete "an" and insert --and--.

Columns 117 to 118, Table 13-continued, the "Objective compound" column, under the fifth structural formula, delete "86%" and insert --88%--.

Column 117 to 118, Table 13-continued, the "Objective compound" column, under the penultimate structural forumla, delete "86%" and insert --76%--.

Column 118, line 64, delete "4-npentyl-" and insert --4-n-pentyl- --.

Column 120, line 26, insert --,-- after "reaction".

UNITED STATES PATENT AND TRADEMARK OFFICE
CERTIFICATE OF CORRECTION

PATENT NO. : 4,112,090
DATED : September 5, 1978
INVENTOR(S) : Saikawa et al

It is certified that error appears in the above—identified patent and that said Letters Patent is hereby corrected as shown below:

Column 121, line 6, delete "4methyl-2,3-dioxo-1-piperazinocarbonyl)-" and insert --4-methyl-2,3-dioxo-1-piperazinocarbonyl-amino)- --.

Column 121, line 9, delete "(lactam," and insert --(lactam),--.

Column 121, line 14, delete "repeated except" and insert --repeated, except--.

Columns 123 to 124, Table 16-continued, in the "Reactive derivative of compound of formula (III)" column delete the third structural formula

UNITED STATES PATENT AND TRADEMARK OFFICE
CERTIFICATE OF CORRECTION

PATENT NO. : 4,112,090
DATED : September 5, 1978
INVENTOR(S) : Saikawa et al

It is certified that error appears in the above—identified patent and that said Letters Patent is hereby corrected as shown below:

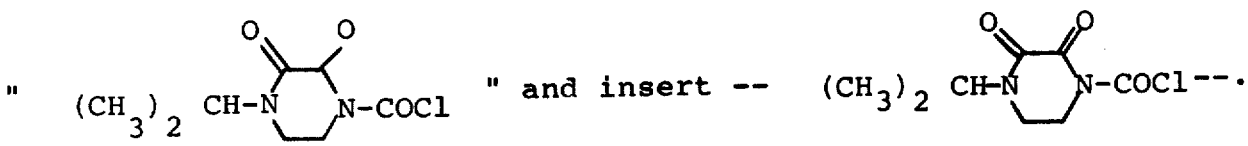

Column 126, line 9, delete "hexonic" and insert -- hexanoic--.

Columns 127, line 42, delete "$-\nu_{NH}$" and insert --$\nu_{NH}$--.

Columns 137 to 138, Table 22-continued, the "Reactive derivative of compound of formula (III)" column and the

UNITED STATES PATENT AND TRADEMARK OFFICE
CERTIFICATE OF CORRECTION

PATENT NO. : 4,112,090
DATED : September 5, 1978
INVENTOR(S) : Saikawa et al

It is certified that error appears in the above—identified patent and that said Letters Patent is hereby corrected as shown below:

"Objective compound" compound delete part of the structural formula:

" 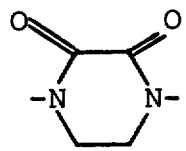 " and insert -- 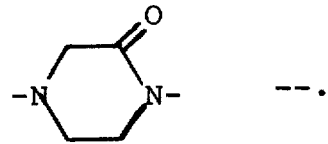 --.

Columns 137 to 138, Table 23 the "Objective compound" column delete part of the first structural formula

UNITED STATES PATENT AND TRADEMARK OFFICE
CERTIFICATE OF CORRECTION

PATENT NO. : 4,112,090
DATED : September 5, 1978
INVENTOR(S) : Saikawa et al

It is certified that error appears in the above—identified patent and that said Letters Patent is hereby corrected as shown below:

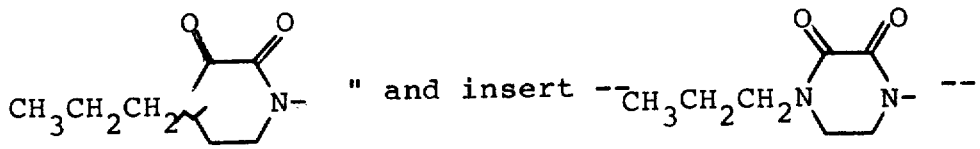

Columns 137 to 138, Table 23, the "Objective compound" column delete the second structural formula "-CH$_2$OCOCH$_2$" and insert -- -CH$_2$OCOCH$_3$".

UNITED STATES PATENT AND TRADEMARK OFFICE
CERTIFICATE OF CORRECTION

PATENT NO. : 4,112,090

DATED : September 5, 1978

INVENTOR(S) : Saikawa et al

It is certified that error appears in the above—identified patent and that said Letters Patent is hereby corrected as shown below:

Column 139, line 47, delete "1600" and insert --1660--.

Column 151, line 6, delete "-COO$^{63}$)" and insert -- -COO$^{\ominus}$ )--

Column 151, line 39, delete "-tetrazolyl]" and insert --

-tetrazolyl)--.

Columns 155 to 156, Table 29-continued, the "Objective compound" column, delete part of the penultimate structural formula " 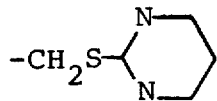 " and insert -- 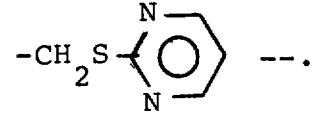 --.

UNITED STATES PATENT AND TRADEMARK OFFICE
CERTIFICATE OF CORRECTION

PATENT NO. : 4,112,090
DATED : September 5, 1978
INVENTOR(S) : Saikawa et al

It is certified that error appears in the above—identified patent and that said Letters Patent is hereby corrected as shown below:

Columns 155 to 156, Table 29-continued, the "Objective compound" column, delete part of the ultimate structural formula

UNITED STATES PATENT AND TRADEMARK OFFICE
CERTIFICATE OF CORRECTION

PATENT NO. : 4,112,090
DATED : September 5, 1978
INVENTOR(S) : Saikawa et al

It is certified that error appears in the above—identified patent and that said Letters Patent is hereby corrected as shown below:

Columns 159 and 161, Table 30, the heading of the column on each, column delete "(III)" and insert --(V)--.

Column 161, line 49, delete "α-" (second occurrence).

Columns 163 to 164, Table 31-continued, the "Objective compound" column, delete part of the third structural formula " 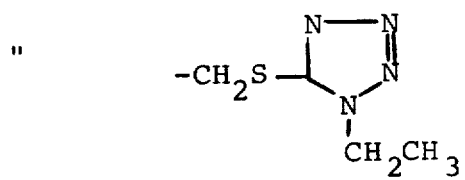 " and insert -- 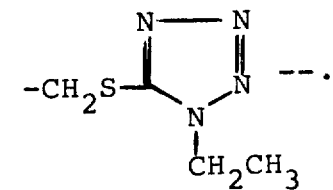 --.

UNITED STATES PATENT AND TRADEMARK OFFICE
CERTIFICATE OF CORRECTION

PATENT NO. : 4,112,090
DATED : September 5, 1978
INVENTOR(S) : Saikawa et al

It is certified that error appears in the above—identified patent and that said Letters Patent is hereby corrected as shown below:

Column 165, line 22, delete "$\alpha$" and insert --$\beta$--

Column 166, line 19, delete "-:66 $\frac{3}{-}$" and insert --$\Delta^3$--.

Column 167, line 8, insert --(2)-- before "To".

Column 169, line 11, delete "($d_6$-DNSO) and insert --($d_6$-DMSO)--.

Column 170, lines 1 to 8, delete part of the structural formula

UNITED STATES PATENT AND TRADEMARK OFFICE
CERTIFICATE OF CORRECTION

PATENT NO. : 4,112,090

DATED : September 5, 1978

INVENTOR(S) : Saikawa et al

It is certified that error appears in the above—identified patent and that said Letters Patent is hereby corrected as shown below:

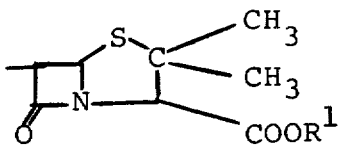

Column 170, line 52; delete "acyl aralkyl" and insert -- acyl, aralkyl,--.

Column 170, line 59; delete "arylsulfonlthiocarbamoyl" and insert --arylsulfonylthiocarbamoyl --.

Column 171, Claim 2, line 3; delete part of the second structural formula

UNITED STATES PATENT AND TRADEMARK OFFICE
CERTIFICATE OF CORRECTION

PATENT NO. : 4,112,090
DATED : September 5, 1978
INVENTOR(S) : Saikawa et al

It is certified that error appears in the above—identified patent and that said Letters Patent is hereby corrected as shown below:

" 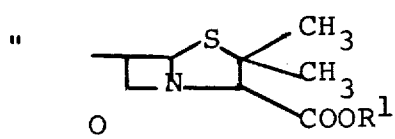 " and insert -- 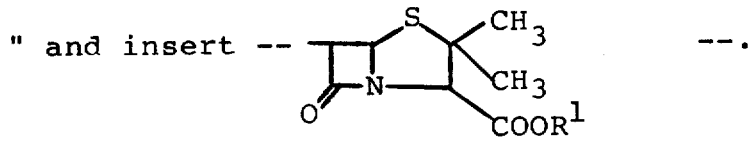 --.

Column 171, line 56; delete "cyano amino," and insert -- cyano, amino,--.

Column 172, lines 14 to 22; delete the structural formula

" 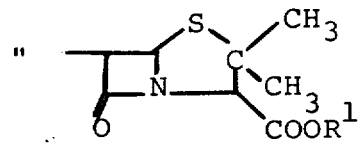 " and insert -- 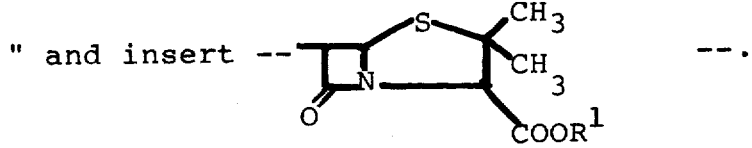 --.

UNITED STATES PATENT AND TRADEMARK OFFICE
CERTIFICATE OF CORRECTION

PATENT NO. : 4,112,090
DATED : September 5, 1978
INVENTOR(S) : Saikawa et al

It is certified that error appears in the above—identified patent and that said Letters Patent is hereby corrected as shown below:

Column 172, line 52; delete "zolyl" and insert --zoyl--.

Column 172, line 63; delete "pivaoyloxymethyl" and insert --pivaloyloxymethyl--.

Column 173, lines 15 to 21; delete "$-\underset{R^6}{\overset{R^5}{\underset{|}{\overset{|}{C}}}}-$" and insert

UNITED STATES PATENT AND TRADEMARK OFFICE
CERTIFICATE OF CORRECTION

PATENT NO. : 4,112,090

DATED : September 5, 1978

INVENTOR(S) : Saikawa et al

It is certified that error appears in the above—identified patent and that said Letters Patent is hereby corrected as shown below:

-- 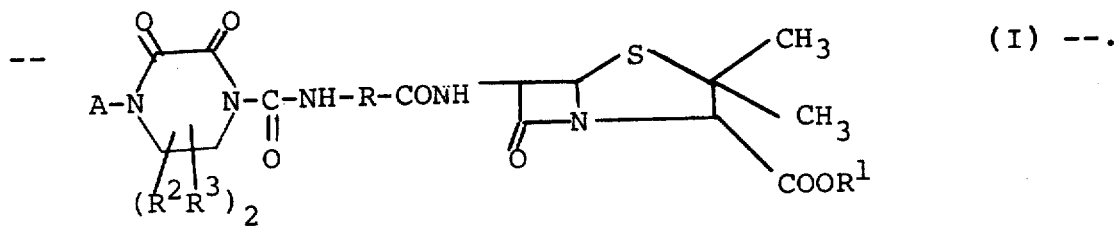 (I) --.

Column 173, line 25; delete

" 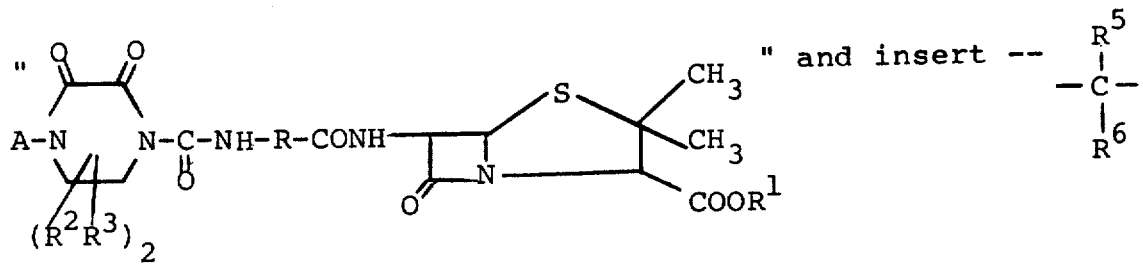 " and insert -- $-\underset{\underset{R^6}{|}}{\overset{\overset{R^5}{|}}{C}}-$ --

UNITED STATES PATENT AND TRADEMARK OFFICE
CERTIFICATE OF CORRECTION

PATENT NO. : 4,112,090
DATED : September 5, 1978
INVENTOR(S) : Saikawa et al

It is certified that error appears in the above-identified patent and that said Letters Patent are hereby corrected as shown below:

Column 173, line 63, delete "di-$C_{1-2}$alkyaminocarbonyl," and insert --di-$C_{1-2}$alkylaminocarbonyl,--.

Signed and Sealed this

Seventh Day of December 1982

[SEAL]

Attest:

GERALD J. MOSSINGHOFF

Attesting Officer      Commissioner of Patents and Trademarks